(12) United States Patent
Hoeben et al.

(10) Patent No.: US 6,238,893 B1
(45) Date of Patent: May 29, 2001

(54) METHOD FOR INTRACELLULAR DNA AMPLIFICATION

(75) Inventors: Robert Cornelis Hoeben, Leiden; Abraham Bout, Moerkapelle, both of (NL)

(73) Assignee: Introgene B.V., Leiden (NL)

( * ) Notice: Subject to any disclaimer, the term of this patent is extended or adjusted under 35 U.S.C. 154(b) by 0 days.

(21) Appl. No.: 09/334,765

(22) Filed: Jun. 16, 1999

Related U.S. Application Data

(63) Continuation of application No. 08/793,170, filed as application No. PCT/NL96/00244 on Jun. 14, 1996, now Pat. No. 5,994,128.

(30) Foreign Application Priority Data

Jun. 15, 1995 (EP) .................................. 95201611
Jun. 26, 1995 (EP) .................................. 95201728

(51) Int. Cl.[7] ............................. C12P 19/34; C12N 15/63
(52) U.S. Cl. .......................................... 435/91.1; 435/455
(58) Field of Search ................... 435/91.1, 325, 435/369, 455

(56) References Cited

U.S. PATENT DOCUMENTS

| | | |
|---|---|---|
| 4,405,712 | 9/1983 | Vande Woude et al. ................. 435/5 |
| 4,497,796 | 2/1985 | Salser et al. ........................... 514/44 |
| 4,727,028 | 2/1988 | Santerre et al. ........................ 435/356 |
| 4,740,463 | 4/1988 | Weinberg et al. ...................... 435/456 |
| 5,190,931 | 3/1993 | Inouye .............................. 435/91.32 |
| 5,208,149 | 5/1993 | Inouye ................................ 435/471 |
| 5,378,618 | 1/1995 | Sternberg et al. ................... 435/91.1 |
| 5,518,913 | 5/1996 | Massie et al. ....................... 435/235.1 |
| 5,545,522 | 8/1996 | Van Gelder et al. ..................... 435/6 |
| 5,552,309 * | 9/1996 | March ................................ 435/172.3 |
| 5,652,224 | 7/1997 | Wilson et al. .......................... 514/44 |
| 5,670,488 | 9/1997 | Gregory et al. ........................ 514/44 |
| 5,707,618 | 1/1998 | Armentano et al. ............... 424/93.21 |
| 5,753,500 | 5/1998 | Shenk et al. ........................ 435/320.1 |
| 5,837,511 | 11/1998 | Falck-Pedersen et al. ............... 435/6 |
| 5,994,106 | 11/1999 | Kovesdi et al. ...................... 435/91.4 |
| 5,994,128 | 11/1999 | Fallaux et al. .......................... 435/325 |
| 6,033,908 | 3/2000 | Bout et al. ............................. 435/325 |
| 6,040,174 | 3/2000 | Imler et al. ............................ 435/325 |

FOREIGN PATENT DOCUMENTS

| | | |
|---|---|---|
| A-28533/95 | 8/1995 | (AU) . |
| 2053187 | 4/1993 | (CA) . |
| 2117668 | 9/1995 | (CA) . |
| 95201611 | 6/1995 | (EP) . |
| 95201728 | 6/1995 | (EP) . |
| 2 707 664 | 1/1995 | (FR) . |
| WO 94/08026 | 4/1994 | (WO) . |
| WO 94/11506 | 5/1994 | (WO) . |
| WO 94/12649 | 6/1994 | (WO) . |
| WO 94/23582 | 10/1994 | (WO) . |
| WO 94/24297 | 10/1994 | (WO) . |
| WO 94/26914 | 11/1994 | (WO) . |
| WO 94/28152 | 12/1994 | (WO) . |
| WO 94/28938 | 12/1994 | (WO) . |
| WO 95/00655 | 1/1995 | (WO) . |
| WO 95/02697 | 1/1995 | (WO) . |
| WO 95/16772 | 6/1995 | (WO) . |
| WO 95/26411 | 10/1995 | (WO) . |
| WO 95/27071 | 10/1995 | (WO) . |
| WO 95/34671 | 12/1995 | (WO) . |
| WO 96/13596 | 5/1996 | (WO) . |
| WO 96/14061 | 5/1996 | (WO) . |
| WO 96/16676 | 6/1996 | (WO) . |
| WO 96/18418 | 6/1996 | (WO) . |
| WO 96/33280 | 10/1996 | (WO) . |
| WO 96/40955 | 12/1996 | (WO) . |
| WO 97/00947 | 1/1997 | (WO) . |
| WO 97/04119 | 2/1997 | (WO) . |
| WO 97/05255 | 2/1997 | (WO) . |

OTHER PUBLICATIONS

Muzyczka (1992) Use of adeno–associated virus as a general transduction vector for mammalian cells. Curr. Topics Mixrobiol. Immunol. 158:97–129.*

Amalfitano et al., "Improved adenovirus packaging cell lines to support the growth of replication–defective gene––delivery vectors", *Proc. Nat. Acad. Sci. USA*, 93:3352–3356, Apr. 1996.

Amalfitano et al., "Isolation and characterization of packaging cell lines that coexpress the adenovirus E1, DNA polymerase, and preterminal proteins: implications for gene therapy", *Gene Therapy*, 4:258–263, 1997.

Armentano et al., "Characterization of an Adenovirus Gene Transfer Containing an E4 Deletion", *Human Gene Therapy*, 6:1343–1353, Oct. 1995.

Brough et al., "A Gene Transfer Vector–Cell Line System for Complete Functional Complemention of Adenovirus Early Regions E1 and E4", *Journal of Virology*, 70(9):6497–6501, Sep. 1996.

Brough et al., "Construction, Characterization, and Utilization of Cell Lines Which Inducibly Express the Adenovirus DNA–Binding Protein", *Virology*, 190:624–634, 1992.

Brough et al., "Restricted changes in the adenovirus DNA–binding protein that lead to extended host range or temperature sensitive phenotypes", *Journal of Virology*, vol. 55, pp. 206–212.

(List continued on next page.)

Primary Examiner—Robert A. Schwartzman
(74) Attorney, Agent, or Firm—Trask Britt

(57) ABSTRACT

A method for intracellular amplification of DNA is disclosed. The method includes providing a mammalian cell with a first nucleic acid sequence encoding functional adenoviral E2A and E2B gene products and with a second nucleic acid sequence encoding a linear DNA fragment to be amplified. The second nucleic acid sequence further has at least one functional adenoviral Inverted Terminal Repeat on a terminus and, in one embodiment where there is only a single ITR, a hairpin-like structure on the other terminus. This allows the linear DNA fragment to be acted upon by the adenoviral E2A and E2B gene products, thus intracellularly amplifying the linear DNA fragment, which can be extracted.

4 Claims, 27 Drawing Sheets

OTHER PUBLICATIONS

Brough et al., Stable Cell Lines for Complementation of Adenovirus Early Regions E1, E2A and E4; *Abstract Book CSH Conference On Gene Therapy*, 42, 1996.

Carovokyri et al., "Constitutive Episomal Expression of Polypeptide IX (pIX) in a 293–Based Cell Line Complements the Deficiency of pIX Mutant Adenovirus Type 5", *Journal of Virology*, 69(11):6627–6633, Nov. 1995.

Engelhardt et al., "Ablation of E2A in recombinant adenoviruses improves transgene persistence and decreases inflammatory response in mouse liver", Proceeding of the National Sciences of USA, vol. 91, pp. 6196–6200, 1994.

Fallaux et al., "Characterization of 911: A New Helper Cell Line for the Titration and Propagation of Early Region 1–Deleted Adenoviral Vectors", *Human Gene Therapy*, 7:215–222, 1996.

Fields et al., "Fields Virology", Second Edition, pp. 28–30, 87.

Fisher et al., "Recombinant Adenovirus Deleted of All Viral Genes for Gene Therapy of Cystic Fibrosis", *Virology*, 217:11–12, 1996.

Gao et al., "Biology of Adenovirus Vectors with E1 and E4 Deletions for Liver–Directed Gene Therapy", *Journal of Virology*, 70(12):8934–8943, Dec. 1996.

Gorziglia et al., "Elimination of both E1 and E2a from Adenovirus Vectors Further Improves Prospects for In Vivo Human Gene Therapy", *Journal of Virology*, 70(6):4173–4178, Jun. 1996.

Hardy et al., "Construction of Adenovirus Vectors through Cre–lox Recombination", *Journal of Virology*, 71(3):1842–1849, Mar. 1997.

Hehir et al., "Molecular Characterization of Replication-–Competent Variants of Adenovirus Vectors and Genome Modifications To Prevent Their Occurrence", *Journal of Virology*, 70(12):8459–8467, Dec. 1996.

Imier et al., "Novel complementation cell lines derived from human lung carcinoma A549 cells support the growth of E1–deleted adenovirus vectors", *Gene Therapy*, 3:75–84, 1996.

Kornberg, Arthur, "DNA Replication", W.H. Freeman and Company, San Francisco, 8 pages.

Krougliak et al., "Development of Cell Lines Capable of Complementing E1, E4, and Protein IX Defective Adenovirus Type 5 Mutants", *Human Gene Therapy*, 6:1575–1586, Dec. 1995.

Lieber et al., "Recombinant Adenoviruses with Large Deletions Generated by Cre–Mediated Excision Exhibit Different Biological Properties Compared with First–Generation Vectors In Vitro and In Vivo", *Journal of Virology*, 70:8944–8960, Dec. 1996.

Ngo et al., "In The Protein Folding Problem and Tertiary Structure Prediction", Merz et al., (ed.), Birkhauser, Boston, MA, pp. 433 and 492–495, 1994.

Sabatie et al., "Process Development for the Production of Second Generation Adenovirus Vectors for Gene Transfer in Clinical Protocols", *Abstract Book 14th Meeting on Animal Cell Technology*, BI–3, 1996.

Schaack et al., "Adenovirus Type 5 Precursor Terminal Protein–Expressing 293 and HeLa Cell Lines", *Journal of Virology*, 69(7):4079–4085, Jul. 1995.

Vanhaesebroeck et al., *Virology*, 176(2), pp. 362–368, Jun. 1990.

Wang et al., "A packaging cell line for propagation of recombinant adenovirus vectors containing two lethal gene–region deletions", *Gene Therapy*, 2:775–783, 1995.

Yeh et al., "Efficient Dual Transcomplementation of Adenovirus E1 and E4 Regions from a 293–Derived Cell Line Expressing a Minimal E4 Functional Unit", *Journal of Virology*, 70(1):559–565, Jan. 1996.

Zhou et al., "Development of a Complementing Cell Line and a System for Construction of Adenovirus Vectors with E1 and E2a Deleted", *Journal of Virology*, 70(1):7030–7038, Oct. 1996.

Bernards, Rene, et al., *Characterization of Cells Transformed by Ad5/Ad12 Hybrid Early Region I Plasmids*, Virology 120, pp. 422–432 (1982).

Bernards, Rene, et al., *Role of Adenovirus Types 5 and 12 Early Region 1b Tumor Antigens in Oncogenic Trahsformation*, Virology 127, pp. 45–53 (1983).

Graham, F.L., et al., *Characteristics of a Human Cell Line Transformed by DNA from Human Adenovirus Type 5*, J. gen. Virol., 36, pp. 59–74, (1977).

Grodzicker, Terri, et al., *Expression of Unselected Adenovirus Genes in Human Cells Co–transformed with the HSV–1 tk Gene and Adenovirus 2 DNA*, Cell, vol. 21, pp. 453–463, Sep. 1980.

Lochmuller, H., et al., *Emergence of Early Region 1–Containing Replication–Competent Adenovirus in Stocks of Replication–Defective Adenovirus Recombinants ($\Delta E1$ = $\Delta E3$) During Multiple Passages in 293 Cells*, Human Gene Therapy 5:1485–1491 (Dec. 1994).

Louis, Nathalie, et al., *Cloning and Sequencing of the Cellular–Viral Junctions from the Human Adenovirus Type 5 Transformed 293 Cell Line*, Virology 233, pp. 423–429 (1997).

Roberts, Bryan E., et al., *Individual Adenovirus Type 5 Early Region 1A Gene Products Elicit Distinct Alterations of Cellular Morphology and Gene Expression*, Journal of Virology, pp. 404–413, Nov. 1985.

Stratford–Perricaudet, Leslie, et al., *Gene Transfer Into Animals: The Promise of Adenovirus*, Human Gene Transfer, vol. 219, pp. 51–61 (1991).

Vaessen, R.T.M.J., *Adenovirus E1A–Mediated Regulation of Class I MHC Expression*, The EMBO Journal, vol. 5, No. 2, pp. 335–341 (1986).

Vaessen, R.T.M.J., *Different Adenovirus E1A–Controlled Properties of Transformed Cells Require Different Levels of E1A Expression*, Gene, pp. 247–254 (1987).

Vanhaesebroeck, Bart, et al., *Modulation of Cellular Susceptibility to the Cytotoxic/Cytostatic Action of Tumor Necrosis Factor by Adenovirus E1 Gene Expression Is Cell Type–Dependent*, Virology 176, pp. 362–368 (1990).

Brough et al., "Multiple Functions of the Adenovirus DNA–Binding Protein Are Required for Efficient Viral DNA Synthesis", *Virology*, 196:269–281, 1993.

Lemarchand et al., "Adenovirus–mediated transfer of a recombinant human $\alpha 1$–antitrypsin cDNA to human endothelial cells", *Proc. Natl. Acad. Sci. USA*, vol. 89, pp. 6482–6486, Jul. 1992.

Orkin et al., "Reports and Recommendations of the Panel to Assess the NIH Investment in Research on Gene Therapy", 21 pages, Dec. 7, 1995.

Rosenfeld et al., "In Vivo Transfer of the Human Cystic Fibrosis Transmembrane Conductance Regulator Gene to the Airway Epithelium", *Cell*, vol. 68, pp. 143–155, Jan. 10, 1992.

Trapnell et al., "Gene therapy using adenoviral vectors", *Current Opinion in Biotechnology*, 5:617–625, 1994.

Vos et al., "Characterization of Adenovirus Type 5 Insertion and Deletion Mutants Encoding Altered DNA Binding Proteins", *Virology*, 172, pp. 634–642, 1989.

Weinberg et al., "A cell line that supports the growth of a defective early region 4 deletion mutant of human adenovirus type 2", *Proc. Natl. Sci. USA*, vol. 80, pp. 5383–5386, Sep. 1983.

Yang et al., "Cellular immunity to viral antigens limits E1–deleted adenoviruses for gene therapy", *Proc. Natl. Acad. Sci. USA*, vol. 91, pp. 4407–4411, May 1994.

* cited by examiner

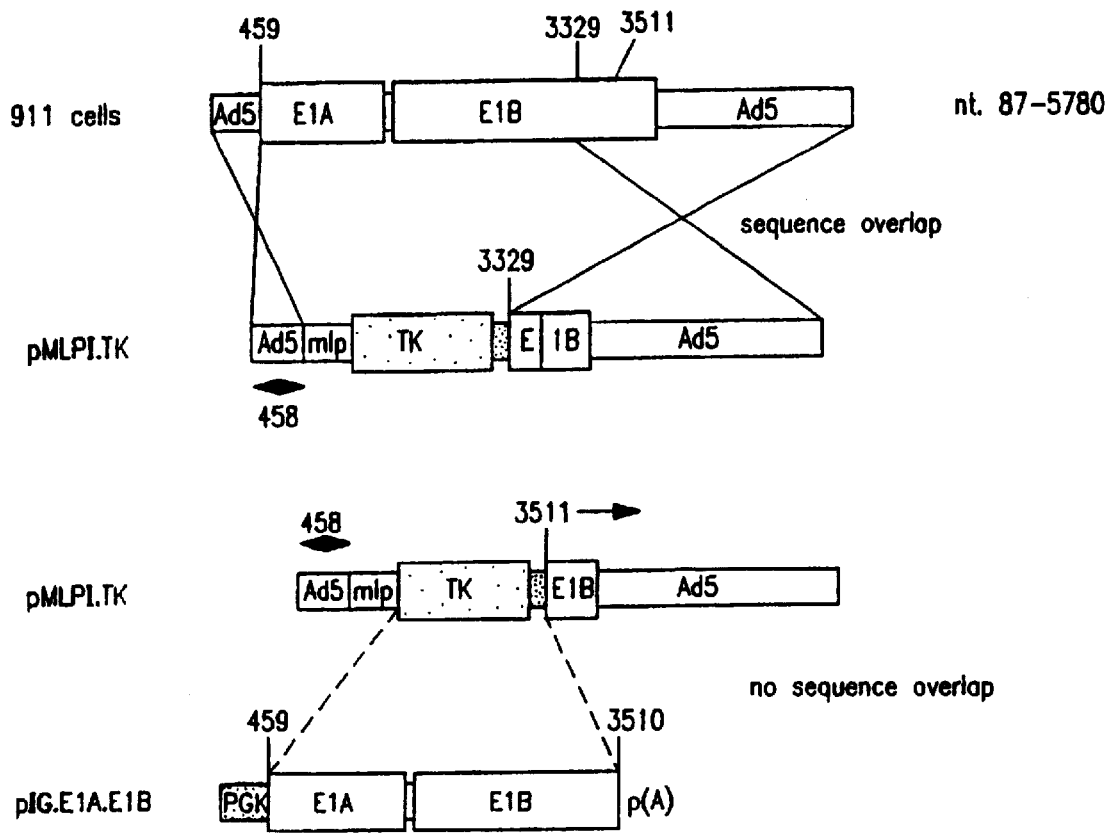
FIG. IIA
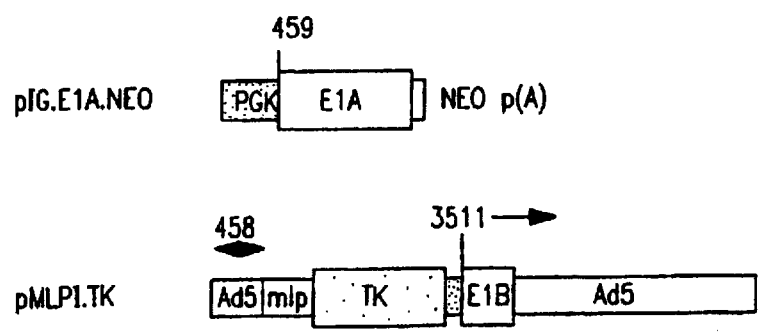
FIG. IIB

```
5'-GTACACTGACCTAGTGCCGCCCGGGCA
         |||||||||||||||| A
         GATCACGGCGGGCCCGA
```

FIG.15

```
CATCATCAAT AATATACCTT ATTTTGGATT GAAGCCAATA TGATAATGAG GGGGTGGAGT    60
TTGTGACGTG GCGCGGGGCG TGGGAACGGG GCGGGTGACG TAGTAGTGTG GCGGAAGTGT   120
GATGTTGCAA GTGTGGCGGA ACACATGTAA GCGACGGATG TGGCAAAAGT GACGTTTTTG   180
GTGTGCGCCG GTGTACACAG GAAGTGACAA TTTTCGCGCG GTTTTAGGCG GATGTTGTAG   240
TAAATTTGGG CGTAACCGAG TAAGATTTGG CCATTTTCGC GGGAAAACTG AATAAGAGGA   300
AGTGAAATCT GAATAATTTT GTGTTACTCA TAGCGCGTAA TATTTGTCTA GGGCCGCGGG   360
GACTTTGACC GTTTACGTGG AGACTCGCCC AGGTGTTTTT CTCAGGTGTT TTCCGGCGTTC  420
CGGGTCAAAG TTGGCGTTTT ATTATTATAG TCAGGGGCTG CAGGTCGTTA CATAACTTAC   480
GGTAAATGGC CCGCCTGGCT GACCGCCCAA CGACCCCCGC CCATTGACGT CAATAATGAC   540
GTATGTTCCC ATAGTAACGC CAATAGGGAC TTTCCATTGA CGTCAATGGG TGGAGTATTT   600
ACGGTAAACT GCCCACTTGG CAGTACATCA AGTGTATCAT ATGCCAAGTA CGCCCCCTAT   660
TGACGTCAAT GACGGTAAAT GGCCCGCCTG GCATTATGCC CAGTACATGA CCTTATGGGA   720
CTTTCCTACT TGGCAGTACA TCTACGTATT AGTCATCGCT ATTACCATGG TGATGCGGTT   780
TTGGCAGTAC ATCAATGGGC GTGGATAGCG GTTTGACTCA CGGGGATTTC CAAGTCTCCA   840
CCCCATTGAC GTCAATGGGA GTTTGTTTTG GCACCAAAAT CAACGGGACT TTCCAAAATG   900
TCGTAACAAC TCCGCCCAT TGACGCAAAT GGGCGGTAGG CGTGTACGGT GGGAGGTCTA   960
TATAAGCAGA GCTCGTTTAG TGAACCGTCA GATCGCCTGG AGACGCCATC CACGCTGTTT  1020
```

FIG. 20A

```
TGACCTCCAT AGAAGACACC GGGACCGATC CAGCCTCCGG ACTCTAGAGG ATCCGGTACT 1080
CGAGGAACTG AAAAACCAGA AAGTTAACTG GTAAGTTTAG TCTTTTTGTC TTTTATTTCA 1140
GGTCCCGGAT CCGGTGGTGG TGCAAATCAA AGAACTGCTC CTCAGTGGAT GTTGCCTTTA 1200
CTTCTAGTAT CAAGCTTGAA TTCCTTTGTG TTACATTCTT GAATGTCGCT CGCAGTGACA 1260
TTAGCATTCC GGTACTGTTG GTAAAATGGA AGACGCCAAA AACATAAAGA AAGGCCCGGC 1320
GCCATTCTAT CCTCTAGAGG ATGGAACCGC TGGAGAGCAA CTGCATAAGG CTATGAAGAA 1380
ATACGCCCTG GTTCCTGGAA CAATTGCTTT TACAGATGCA CATATCGAGG TGAACATCAC 1440
GTACGCGGAA TACTTCGAAA TGTCCGTTCG GTTGGCAGAA GCTATGAAAC GATATGGGCT 1500
GAATACAAAT CACAGAATCG TGAAAACTCT CTTCAATTCT TTATGCCGGT 1560
GTTGGGCGCG TTATTATCG TGCGCCCGCG AACGACATTT ATAATGAACG 1620
TGAATTGCTC AACAGTATGA ACATTTCGCA GCCTACCGTA GTGTTTGTTT CCAAAAGGG 1680
GTTGCAAAAA ATTTTGAACG TGCAAAAAAA ATTACCAATA ATCCAGAAAA TTATTATCAT 1740
GGATTCTAAA ACGGATTACC AGGGATTTCA GTCGATGTAC ACGTTCGTCA CATCTCATCT 1800
ACCTCCCGGT TTTAATGAAT ACGATTTTGT ACCAGAGTCC TTTGATCGTG ACAAAACAAT 1860
TGCACTGATA ATGAATTCCT CTGGATCTAC TGGGTTACCT AAGGGTGTGG CCCTTCCGCA 1920
TAGAACTGCC TGCGTCAGAT TCTCGCATGC CAGAGATCCT ATTTTGGCA ATCAAATCAT 1980
TCCGGATACT GCGATTTTAA GTGTTGTTCC ATTCCATCAC GGTTTTGGAA TGTTTACTAC 2040
```

FIG. 20B

```
ACTCGGATAT TTGATATGTG GATTTCGAGT CGTCTTAATG TATAGATTTG AAGAAGAGCT 2100
GTTTTTACGA TCCCTTCAGG ATTACAAAAT TCAAAGTGCG TTGCTAGTAC CAACCCTATT 2160
TTCATTCTTC GCCAAAAGCA CTCTGATTGA CAAATACGAT TTATCTAATT TACACGAAAT 2220
TGCTTCTGGG GGCGCACCTC TTTCGAAAGA AGTCGGGGAA GCGGTTGCAA AACGCTTCCA 2280
TCTTCCAGGG ATACGACAAG GATATGGGCT CACTGAGACT ACATCAGCTA TTCTGATTAC 2340
ACCCGAGGGG GATGATAAAC CGGGGCGGGT CGGTAAAGTT GTTCCATTTT TTGAAGCGAA 2400
GGTTGTGGAT CTGGATACCG GGAAAACGCT GGGCGTTAAT CAGAGAGGCG AATTATGTGT 2460
CAGAGGACCT ATGATTATGT CCGGTTATGT AAACAATCCG GAAGCGACCA ACGCCTTGAT 2520
TGACAAGGAT GGATGGCTAC ATTCTGGAGA CATAGCTTAC TGGGACGAAG ACGAACACTT 2580
CTTCATAGTT GACCGCTTGA AGTCTTTAAT TAAATACAAA GGATATCAGG TGGCCCCCGC 2640
TGAATTGGAA TCGATATTGT TACAACACCC CAACATCTTC GACGCGGGCG TGGCAGGTCT 2700
TCCCGACGAT GACGCCGGTG AACTTCCCGC CGCCGTTGTT GTTTTGGAGC ACGGAAAGAC 2760
GATGACGGAA AAAGAGATCG TGGATTACGT CGCCAGTCAA GTAACAACCG CGAAAAAGTT 2820
GCGCGGAGGA GTTGTGTTTG TGGACGAAGT ACCGAAAAGT CTTACCGGAA AACTCGACGC 2880
AAGAAAAATC AGAGAGATCC TCATAAAGGC CAAGAAGGGC GGAAAGTCCA AATTGTAAAA 2940
TGTAACTGTA TTCAGCGATG ACGAAATTCT TAGCTATTGT AATGGGGGAT CCCCAACTTG 3000
TTTATTGCAG CTTATAATGG TTACAAATAA AGCAATAGCA TCACAAATTT CACAAATAAA 3060
```

FIG. 20C

```
GCATTTTTT  CACTGCATTC  TAGTTGTGGT  TTGTCCAAAC  TCATCAATGT  ATCTTATCAT  3120
GTCTGGATCG  GATCGATCCC  CGGGTACCGA  GCTCGAATTC  GTAATCATGG  TCATAGCTGT  3180
TTCCTGTGTG  AAATTGTTAT  CCGCTCACAA  TTCCACACAA  CATACGAGCC  GGAAGCATAA  3240
AGTGTAAAGC  CTGGGGTGCC  TAATGAGTGA  GCTAACTCAC  ATTAATTGCG  TTGCGCTCAC  3300
TGCCCGCTTT  CCAGTCGGGA  AACCTGTCGT  GCCAGCTGCA  TTAATGAATC  GGCCAACGCG  3360
CGGGGAGAGG  CGGTTTGCGT  ATTGGGCGCT  CTTCCGCTTC  CTCGCTCACT  GACTCGCTGC  3420
GCTCGGTCGT  TCGGCTGCGG  CGAGCGGTAT  CAGCTCACTC  AAAGGCGGTA  ATACGGTTAT  3480
CCACAGAATC  AGGGGATAAC  GCAGGAAAGA  ACATGTGAGC  AAAAGGCCAG  CAAAAGGCCA  3540
GGAACCGTAA  AAAGGCCGCG  TTGCTGGCGT  TTTTCCATAG  GCTCCGCCCC  CCTGACGAGC  3600
ATCACAAAAA  TCGACGCTCA  AGTCAGAGGT  GGCGAAACCC  GACAGGACTA  TAAAGATACC  3660
AGGCGTTTCC  CCCTGGAAGC  TCCCTCGTGC  GCTCTCCTGT  TCCGACCCTG  CCGCTTACCG  3720
GATACCTGTC  CGCCTTTCTC  CCTTCGGGAA  GCGTGGCGCT  TTCTCATAGC  TCACGCTGTA  3780
GGTATCTCAG  TTCGGTGTAG  GTCGTTCGCT  CCAAGCTGGG  CTGTGTGCAC  GAACCCCCCG  3840
TTCAGCCCGA  CCGCTGCGCC  TTATCCGGTA  ACTATCGTCT  TGAGTCCAAC  CCGGTAAGAC  3900
ACGACTTATC  GCCACTGGCA  GCAGCCACTG  GTAACAGGAT  TAGCAGAGCG  AGGTATGTAG  3960
GCGGTGCTAC  AGAGTTCTTG  AAGTGGTGGC  CTAACTACGG  CTACACTAGA  AGGACAGTAT  4020
TTGGTATCTG  CGCTCTGCTG  AAGCCAGTTA  CCTTCGGAAA  AAGAGTTGGT  AGCTCTTGAT  4080
```

FIG. 20D

```
CCGGCAAACA AACCACCGCT GGTAGCGGGTG GTTTTTTGT TTGCAAGCAG CAGATTACGC  4140
GCAGAAAAAA AGGATCTCAA GAAGATCCTT TGATCTTTTC TACGGGTCT GACGCTCAGT  4200
GGAACGAAAA CTCACGTTAA GGGATTTTGG TCATGAGATT ATCAAAAAGG ATCTTCACCT  4260
AGATCCTTTT AAATTAAAAA TGAAGTTTTA AATCAATCTA AAGTATATAT GAGTAAACTT  4320
GGTCTGACAG TTACCAATGC TTAATCAGTG AGGCACCTAT CTCAGCGATC TGTCTATTTC  4380
GTTCATCCAT AGTTGCCTGA CTCCCCGTCG TGTAGATAAC TACGATACGG GAGGGCTTAC  4440
CATCTGGCCC CAGTGCTGCA GAGACCCACG CTCACCGGCT CCAGATTTAT CCAGTTAATA  4500
CAGCAATAAA CCAGCCAGCC GGAAGGGCCG AGCGCAGAAG TGGTCCTGCA ACTTTATCCG  4560
CCTCCATCCA GTCTATTAAT TGTTTGCCGG AAGCTAGAGT AAGTAGTTCG CCAGTTAATA  4620
GTTTGCGCAA CGTTGTTGCC ATTGCTACAG GCATCGTGGT GTCACGCTCG TCGTTTGGTA  4680
TGGCTTCATT CAGCTCCGGT TCCCAACGAT CAAGGCGAGT TACATGATCC CCCATGTTGT  4740
GCAAAAAAGC GGTTAGCTCC TTCGGTCCTC CGATCGTTGT CAGAAGTAAG TTGGCCGCAG  4800
TGTTATCACT CATGGTTATG GCAGCACTGC ATAATTCTCT TACTGTCATG CCATCCGTAA  4860
GATGCTTTTC TGTGACTGGT GAGTACTCAA CCAAGTCATT CTGAGAATAG TGTATGCGGC  4920
GACCGAGTTG CTCTTGCCCG GCGTCAATAC GGGATAAATAC CGCGCCACAT AGCAGAACTT  4980
TAAAAGTGCT CATCATTGGA AAACGTTCTT CGGGGCGAAA ACTCTCAAGG ATCTTACCGC  5040
TGTTGAGATC CAGTTCGATG TAACCCACTC GTGCACCCAA CTGATCTTCA GCATCTTTTA  5100
```

FIG. 20E

```
CTTTCACCAG CGTTTCTGGG TGAGCAAAAA CAGGAAGGCA AAATGCCGCA AAAAAGGGAA 5160
TAAGGGCGAC ACGGAAATGT TGAATACTCA TACTCTTCCT TTTTCAATAT TATTGAAGCA 5220
TTTATCAGGG TTATTGTCTC ATGAGCGGAT ACATATTTGA ATGTATTTAG AAAAATAAAC 5280
AAATAGGGGT TCCGCGCACA TTTCCCCGAA AAGTGCCACC TGACGTCTAA GAAACCATTA 5340
TTATCATGAC ATTAACCTAT AAAAATAGGC GTATCACGAG GCCCTATGCGG TGTGAAATAC 5400
CGCACAGATG CGTAAGGAGA AAATACCGCA TCAGGCGCCA TTCGCCATTC AGGCTGCGCA 5460
ACTGTTGGGA AGGGCGATCG GTGCGGGCCT CTTCGCTATT ACGCCAGCTG GCGAAAGGGG 5520
GATGTGCTGC AAGGCGATTA AGTTGGGTAA CGCCAGGGTT TTCCCAGTCA CGACGTTGTA 5580
AAACGACGGC CAGTGCCAAG CTTGCATGCC TGCAGGTCGA                      5620
```

FIG. 20F

METHOD FOR INTRACELLULAR DNA AMPLIFICATION

CROSS REFERENCE TO RELATED APPLICATION

This patent application is a continuation of Ser. No. 08/793,170 filed Mar. 25, 1997, now U.S. Pat. No. 5,994, 128, which is a 371 of International Patent Application PCT/NL96/00244 filed on Jun. 14, 1996 which itself claims priority from European patent application 95201728.3 filed on Jun. 26, 1995 and European patent application 95201611.1 filed on Jun. 15, 1995.

TECHNICAL FIELD

The invention relates to the field of recombinant DNA technology, more in particular to the field of gene therapy. In particular the invention relates to gene therapy using materials derived from adenovirus, specifically human recombinant adenovirus. It especially relates to novel virus derived vectors and novel packaging cell lines for vectors based on adenoviruses.

BACKGROUND

Gene therapy is a recently developed concept for which a wide range of applications can be and have been envisioned. In gene therapy a molecule carrying genetic information is introduced into some or all cells of a host, as a result of which the genetic information is added to the host in a functional format.

The genetic information added may be a gene or a derivative of a gene, such as a cDNA, which encodes a protein. This is a functional format in that the protein can be expressed by the machinery of the host cell.

The genetic information can also be a sequence of nucleotides complementary to a sequence of nucleotides (either DNA or RNA) present in the host cell. This is a functional format in that the added DNA (nucleic acid) molecule or copies made thereof in situ are capable of base pairing with the complementary sequence present in the host cell.

Applications include the treatment of genetic disorders by supplementing a protein or other substance which, because of the genetic disorder, is either absent or present in insufficient amounts in the host, the treatment of tumors and the treatment of other acquired diseases such as (auto)immune diseases, infections, etc.

As may be inferred from the above, there are basically three different approaches in gene therapy: the first directed towards compensating for a deficiency in a (mammalian) host, the second directed towards the removal or elimination of unwanted substances (organisms or cells) and the third towards application of a recombinant vaccine (against tumors or foreign micro-organisms).

For the purpose of gene therapy, adenoviruses carrying deletions have been proposed as suitable vehicles for genetic information. Adenoviruses are non-enveloped DNA viruses. Gene-transfer vectors derived from adenoviruses (so-called "adenoviral vectors") have a number of features that make them particularly useful for gene transfer for such purposes. For example, the biology of the adenoviruses is characterized in detail, the adenovirus is not associated with severe human pathology, the virus is extremely efficient in introducing its DNA into the host cell, the virus can infect a wide variety of cells and has a broad host-range, the virus can be produced in large quantities with relative ease, and the virus can be rendered replication defective by deletions in the early-region 1 ("E1") of the viral genome.

The adenovirus genome is a linear double-stranded DNA molecule of approximately 36000 base pairs with the 55-kDa terminal protein covalently bound to the 5' terminus of each strand. The adenoviral ("Ad") DNA contains identical Inverted Terminal Repeats ("ITR") of about 100 base pairs with the exact length depending on the serotype. The viral origins of replication are located within the ITRs exactly at the genome ends. DNA synthesis occurs in two stages. First, the replication proceeds by strand displacement, generating a daughter duplex molecule and a parental displaced strand. The displaced strand is single stranded and can form a so-called "panhandle" intermediate, which allows replication initiation and generation of a daughter duplex molecule. Alternatively, replication may proceed from both ends of the genome simultaneously, obviating the requirement to form the panhandle structure. The replication is summarized in FIG. 14 adapted from Lechner and Kelly (1977).

During the productive infection cycle, the viral genes are expressed in two phases: the early phase, which is the period up to viral DNA replication, and the late phase, which coincides with the initiation of viral DNA replication. During the early phase only the early gene products, encoded by regions E1, E2, E3 and E4, are expressed, which carry out a number of functions that prepare the cell for synthesis of viral structural proteins (Berk, 1986). During the late phase the late viral gene products are expressed in addition to the early gene products and host cell DNA and protein synthesis are shut off. Consequently, the cell becomes dedicated to the production of viral DNA and of viral structural proteins (Tooze, 1981).

The E1 region of adenovirus is the first region of adenovirus expressed after infection of the target cell. This region consists of two transcriptional units, the E1A and E1B genes, which both are required for oncogenic transformation of primary (embryonic) rodent cultures. The main functions of the E1A gene products are 1) to induce quiescent cells to enter the cell cycle and resume cellular DNA synthesis, and 2) to transcriptionally activate the E1B gene and the other early regions (E2, E3, E4). Transfection of primary cells with the E1A gene alone can induce unlimited proliferation (immortalization), but does not result in complete transformation. However, expression of E1A in most cases results in induction of programmed cell death (apoptosis), and only occasionally immortalization (Jochemsen et al., 1987). Co-expression of the E1B gene is required to prevent induction of apoptosis and for complete morphological transformation to occur. In established immortal cell lines, high level expression of E1A can cause complete transformation in the absence of E1B (Roberts et al., 1985).

The E1B encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomittantly with the onset of the late phase of infection. The E1B 21 kD protein is important for correct temporal control of the productive infection cycle, thereby preventing premature death of the host cell before the virus life cycle has been completed. Mutant viruses incapable of expressing the E1B 21 kD gene-product exhibit a shortened infection cycle that is accompanied by excessive degradation of host cell chromosomal DNA (deg-phenotype) and in an enhanced cytopathic effect (cyt-phenotype) (Telling et al., 1994). The deg and cyt phenotypes are suppressed when in addition the E1A gene is mutated, indicating that these phenotypes are a function of E1A (White et al., 1988). Furthermore, the E1B 21 kDa protein slows down the rate by which E1A switches on the other viral genes. It is not yet known through which mechanisms E1B 21 kD quenches these E1A dependent functions.

Vectors derived from human adenoviruses, in which at least the E1 region has been deleted and replaced by a gene of interest, have been used extensively for gene therapy experiments in the pre-clinical and clinical phase.

As stated before, all adenovirus vectors currently used in gene therapy are believed to have a deletion in the E1 region, where novel genetic information can be introduced. The E1 deletion renders the recombinant virus replication defective (Stratford-Perricaudet and Perricaudet, 1991). We have demonstrated that recombinant adenoviruses are able to efficiently transfer recombinant genes to the rat liver and airway epithelium of rhesus monkeys (Bout et al., 1994b; Bout et al., 1994a). In addition, we (Vincent et al., 1996a; Vincent et al., 1996b) and others (see, e.g, Haddada et al., 1993) have observed a very efficient in vivo adenovirus mediated gene transfer to a variety of tumor cells in vitro and to solid tumors in animals models (lung tumors, glioma) and human xenografts in immunodeficient mice (lung) in vivo (reviewed by Blaese et al., 1995).

In contrast to (for instance) retroviruses, adenoviruses 1) do not integrate into the host cell genome, 2) are able to infect non-dividing cells, and 3) are able to efficiently transfer recombinant genes in vivo (Brody and Crystal, 1994). Those features make adenoviruses attractive candidates for in vivo gene transfer of, for instance, suicide or cytokine genes into tumor cells.

However, a problem associated with current recombinant adenovirus technology is the possibility of unwanted generation of replication competent adenovirus ("RCA") during the production of recombinant adenovirus (Lochmüller et al., 1994; Imler et al., 1996). This is caused by homologous recombination between overlapping sequences from the recombinant vector and the adenovirus constructs present in the complementing cell line, such as the 293 cells (Graham et al., 1977). RCA in batches to be used in clinical trials is unwanted because RCA 1) will replicate in an uncontrolled fashion, 2) can complement replication defective recombinant adenovirus, causing uncontrolled multiplication of the recombinant adenovirus and 3) batches containing RCA induce significant tissue damage and hence strong pathological side effects (Lochmüller et al., 1994). Therefore, batches to be used in clinical trials should be proven free of RCA (Ostrove, 1994).

It was generally thought that E1-deleted vectors would not express any other adenovirus genes. However, recently it has been demonstrated that some cell types are able to express adenovirus genes in the absence of E1 sequences. This indicates, that some cell types possess the machinery to drive transcription of adenovirus genes. In particular, it was demonstrated that such cells synthesize E2A and late adenovirus proteins.

In a gene therapy setting, this means that transfer of the therapeutic recombinant gene to somatic cells not only results in expression of the therapeutic protein but may also result in the synthesis of viral proteins. Cells that express adenoviral proteins are recognized and killed by Cytotoxic T Lymphocytes, which thus 1) eradicates the transduced cells and 2) causes inflammations (Bout et al., 1994a; Engelhardt et al., 1993; Simon et al., 1993). As this adverse reaction is hampering gene therapy, several solutions to this problem have been suggested, such as 1) using immunosuppressive agents after treatment; 2) retainment of the adenovirus E3 region in the recombinant vector (see patent application EP 95202213) and 3) and using temperature sensitive ("ts") mutants of human adenovirus, which have a point mutation in the E2A region rendering them temperature sensitive, as has been claimed in patent WO/28938.

However, these strategies to circumvent the immune response have their limitations. The use of ts mutant recombinant adenovirus diminishes the immune response to some extent, but was less effective in preventing pathological responses in the lungs (Engelhardt et al., 1994a).

The E2A protein may induce an immune response by itself and it plays a pivotal role in the switch to the synthesis of late adenovirus proteins. Therefore, it is attractive to make temperature sensitive recombinant human adenoviruses.

A major drawback of this system is the fact that, although the E2 protein is unstable at the non-permissive temperature, the immunogenic protein is still being synthesized. In addition, it is to be expected that the unstable protein does activate late gene expression, albeit to a low extent. ts125 mutant recombinant adenoviruses have been tested, and prolonged recombinant gene expression was reported (Yang et al., 1994b; Engelhardt et al., 1994a; Engelhardt et al., 1994b; Yang et al., 1995). However, pathology in the lungs of cotton rats was still high (Engelhardt et al., 1994a), indicating that the use of ts mutants results in only a partial improvement in recombinant adenovirus technology. Others (Fang et al., 1996) did not observe prolonged gene expression in mice and dogs using ts125 recombinant adenovirus. An additional difficulty associated with the use of ts125 mutant adenoviruses is that a high frequency of reversion is observed. These revertants are either real revertants or the result of second site mutations (Kruijer et al., 1983; Nicolas et al., 1981). Both types of revertants have an E2A protein that functions at normal temperature and have therefore similar toxicity as the wild-type virus.

SUMMARY OF THE INVENTION

In one aspect of the invention, this problem in virus production is solved in that we have developed packaging cells that have no overlapping sequences with a new basic vector and thus are suited for safe large scale production of recombinant adenoviruses one of the additional problems associated with the use of recombinant adenovirus vectors is the host-defense reaction against treatment with adenovirus.

Briefly, recombinant adenoviruses are deleted for the E1 region. The adenovirus E1 products trigger the transcription of the other early genes (E2, E3, E4), which consequently activate expression of the late virus genes.

In another aspect of the present invention we therefore delete E2A coding sequences from the recombinant adenovirus genome and transfect these E2A sequences into the (packaging) cell lines containing E1 sequences to complement recombinant adenovirus vectors.

Major hurdles in this approach are 1) that E2A should be expressed to very high levels and 2) that E2A protein is very toxic to cells.

The current invention in yet another aspect therefore discloses use of the ts125 mutant E2A gene, which produces a protein that is not able to bind DNA sequences at the non permissive temperature. High levels of this protein may be maintained in the cells (because it is non-toxic at this temperature) until the switch to the permissive temperature is made. This can be combined with placing the mutant E2A gene under the direction of an inducible promoter, such as for instance tet, methallothionein, steroid inducible promoter, retinoic acid β-receptor or other inducible systems. However in yet another aspect of the invention, the use of an inducible promoter to control he moment of production of toxic wild-type E2A is disclosed.

Two salient additional advantages of E2A-deleted recombinant adenovirus are the increased capacity to harbor heterologous sequences and the permanent selection for cells that express the mutant E2A. This second advantage relates to the high frequency of reversion of ts125 mutation: when reversion occurs in a cell line harboring ts125 E2A, this will be lethal to the cell. Therefore, there is a permanent selection for those cells that express the ts125 mutant E2A protein. In addition, as we in one aspect of the invention generate E2A-deleted recombinant adenovirus, we will not have the problem of reversion in our adenoviruses.

In yet another aspect of the invention as a further improvement the use of non-human cell lines as packaging cell lines is disclosed.

For GMP production of clinical batches of recombinant viruses it is desirable to use a cell line that has been used widely for production of other biotechnology products. Most of the latter cell lines are from monkey origin, which have been used to produce, for example, vaccines.

These cells can not be used directly for the production of recombinant human adenovirus, as human adenovirus cannot replicate, or replicates only to low levels in cells of monkey origin. A block in the switch of early to late phase of adenovirus lytic cycle underlies defective replication. However, host range mutations in the human adenovirus genome are described (hr400–404) which allow replication of human viruses in monkey cells. These mutations reside in the gene encoding E2A protein (Klessig and Grodzicker, 1979; Klessig et al., 1984; Rice and Klessig, 1985)(Klessig et al., 1984). Moreover, mutant viruses have been described that harbor both the hr and temperature-sensitive ts125 phenotype (Brough et al., 1985; Rice and Klessig, 1985).

We therefore generate packaging cell lines of monkey origin (e.g., VERO, CV1) that harbor:

1) E1 sequences, to allow replication of E1/E2 defective adenoviruses, and
2) E2A sequences, containing the hr mutation and the ts125 mutation, named ts400 (Brough et al., 1985; Rice and Klessig, 1985) to prevent cell death by E2A overexpression, and/or
3) E2A sequences, just containing the hr mutation, under the control of an inducible promoter, and/or
4) E2A sequences, containing the hr mutation and the ts125 mutation (ts400), under the control of an inducible promoter Furthermore we disclose the construction of novel and improved combinations of packaging cell lines and recombinant adenovirus vectors. We provide:

1) a novel packaging cell line derived from diploid human embryonic retinoblasts ("HER") that harbors nt. 80–5788 of the Ad5 genome. This cell line, named 911, deposited under no 95062101 at the ECACC, has many characteristics that make it superior to the commonly used 293 cells (Fallaux et al., 1996).
2) novel packaging cell lines that express just E1A genes and not E1B genes. Established cell lines (and not human diploid cells of which 293 and 911 cells are derived) are able to express E1A to high levels without undergoing apoptotic cell death, as occurs in human diploid cells that express E1A in the absence of E1B. Such cell lines are able to trans-complement E1B-defective recombinant adenoviruses, because viruses mutated for E1B 21 kD protein are able to complete viral replication even faster than wild-type adenoviruses (Telling et al., 1994). The constructs are described in detail below, and graphically represented in FIGS. 1–5. The constructs are transfected into the different established cell lines and are selected for high expression of E1A. This is done by operatively linking a selectable marker gene (e.g., NEO gene) directly to the E1B promoter. The E1B promoter is transcriptionally activated by the E1A gene product and therefore resistance to the selective agent (e.g., G418 in the case NEO is used as the selection marker) results in direct selection for desired expression of the E1A gene.
3) Packaging constructs that are mutated or deleted for E1B 21 kD, but just express the 55 kD protein.
4) Packaging constructs to be used for generation of complementing packaging cell lines from diploid cells (not exclusively of human origin) without the need for selection with marker genes. These cells are immortalized by expression of E1A. However, in this particular case expression of E1B is essential to prevent apoptosis induced by E1A proteins. Selection of E1 expressing cells is achieved by selection for focus formation (immortalization), as described for 293 cells (Graham et al., 1977) and 911 cells (Fallaux et al., 1996), that are E1-transformed human embryonic kidney ("HEK") cells and human embryonic retinoblasts ("HER"), respectively.
5) After transfection of HER cells with construct pIG.E1B (FIG. 4), seven independent cell lines could be established. These cell lines were designated PER.C1, PER.C3, PER.C4, PER.C5, PER.C6, PER.C8 and PER.C9. PER denotes PGK-E1-Retinoblasts. These cell lines express E1A and E1B proteins, are stable (e.g., PER.C6 for more than 57 passages) and complement E1 defective adenovirus vectors. Yields of recombinant adenovirus obtained on PER cells are a little higher than obtained on 293 cells. One of these cell lines (PER.C6) has been deposited at the ECACC under number 96022940.
6) New adenovirus vectors with extended E1 deletions (deletion nt. 459–3510). Those viral vectors lack sequences homologous to E1 sequences in said packaging cell lines. These adenoviral vectors contain pIX promoter sequences and the pIX gene, as pIX (from its natural promoter sequences) can only be expressed from the vector and not by packaging cells (Matsui et al., 1986, Hoeben and Fallaux, pers.comm.; Imler et al., 1996).
7) E2A expressing packaging cell lines preferably based on either E1A expressing established cell lines or E1A–E1B expressing diploid cells (see under 2–4). E2A expression is either under the control of an inducible promoter or the E2A ts125 mutant is driven by either an inducible or a constitutive promoter.
8) Recombinant adenovirus vectors as described before (see 6) but carrying an additional deletion of E2A sequences.
9) Adenovirus packaging cells from monkey origin that are able to trans-complement E1-defective recombinant adenoviruses. They are preferably co-transfected with pIG.E1AE1B and pIG.NEO, and selected for NEO resistance. Such cells expressing E1A and E1B are able to transcomplement E1 defective recombinant human adenoviruses, but will do so inefficiently because of a block of the synthesis of late adenovirus proteins in cells of monkey origin (Klessig and Grodzicker, 1979). To overcome this problem, we generate recombinant adenoviruses that harbor a host-range mutation in the E2A gene, allowing human adenoviruses to replicate in monkey cells. Such viruses are generated as described in FIG. 12, except DNA from a hr-mutant is used for homologous recombination.

10) Adenovirus packaging cells from monkey origin as described under 9, except that they will also be co-transfected with E2A sequences harboring the hr mutation. This allows replication of human adenoviruses lacking E1 and E2A (see under 8). E2A in these cell lines is either under the control of an inducible promoter or the tsE2A mutant is used. In the latter case, the E2A gene will thus carry both the ts mutation and the hr mutation (derived from ts400). Replication competent human adenoviruses have been described that harbor both mutations (Brough et al., 1985; Rice and Klessig, 1985).

A further aspect of the invention provides otherwise improved adenovirus vectors, as well as novel strategies for generation and application of such vectors and a method for the intracellular amplification of linear DNA fragments in mammalian cells.

BRIEF DESCRIPTION OF THE FIGURES

The following figures and drawings may help to understand the invention:

FIGS. 11A and 11B illustrate new adenovirus packaging constructs which do not have sequence overlap with new adenovirus vectors.

FIG. 15 illustrates a potential hairpin conformation of a single-stranded DNA molecule that contains the HP/asp sequence (SEQ. I.D. NO.17).

FIGS. 20A–20F recite the nucleotide sequence (SEQ. I.D. NO. 21) of pICL 5620BPS DNA (circular).

DETAILED DESCRIPTION OF THE INVENTION

The so-called "minimal" adenovirus vectors according to the present invention retain at least a portion of the viral genome that is required for encapsidation of the genome into virus particles (the encapsidation signal), as well as at least one copy of at least a functional part or a derivative of the ITR, that is DNA sequences derived from the termini of the linear adenovirus genome. The vectors according to the present invention will also contain a transgene linked to a promoter sequence to govern expression of the transgene. Packaging of the so-called minimal adenovirus vector can be achieved by co-infection with a helper virus or, alternatively, with a packaging deficient replicating helper system as described below.

Figure 13:
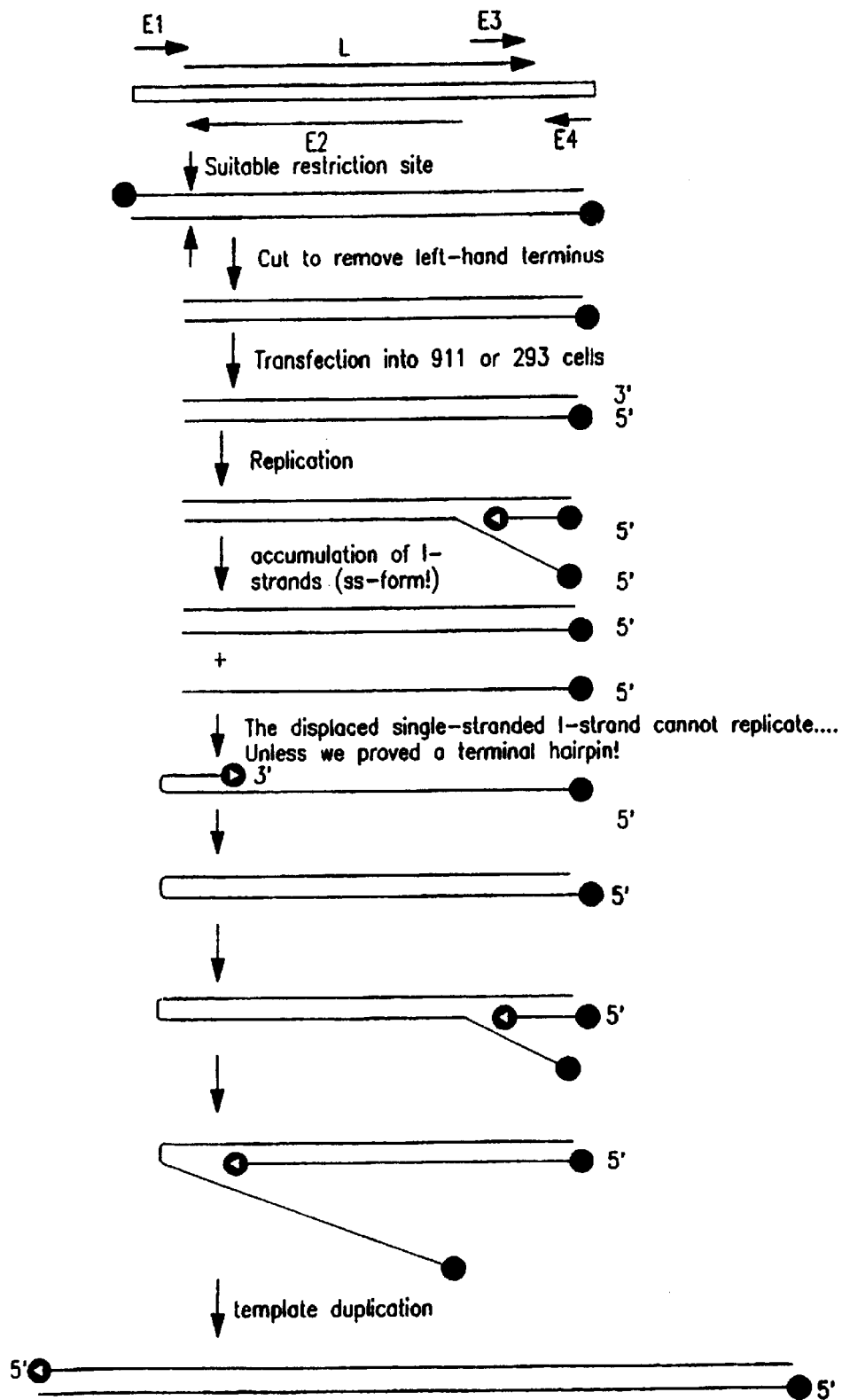
FIG. 13 illustrates the adenovirus double-stranded DNA genome indicating the approximate locations of E1, E2, E3, E4, and L regions.
Figure 14:
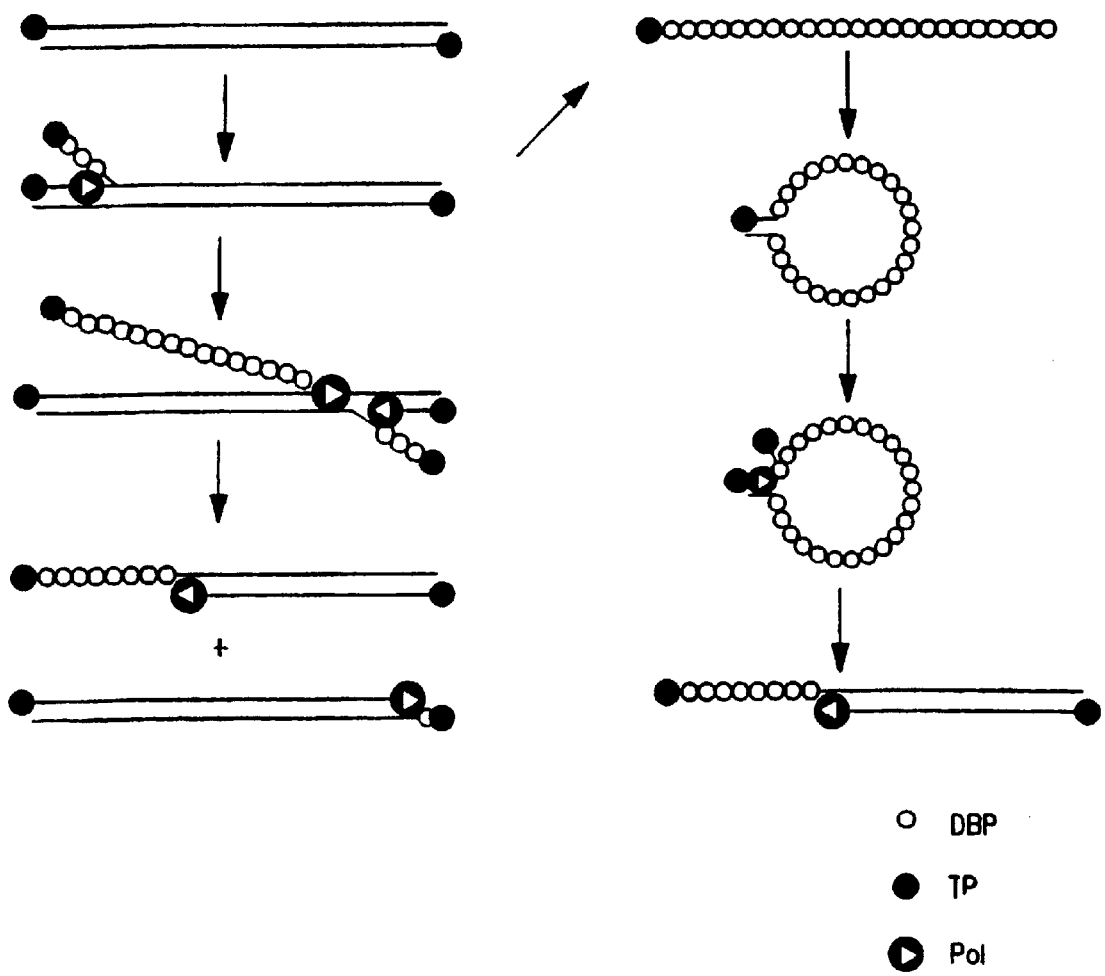
FIG. 14 illustrates the adenovirus genome is shown in the top left with the origins of replication located within the left and right ITRs at the genome ends.

Adenovirus-derived DNA fragments that can replicate in suitable cell lines and that may serve as a packaging deficient replicating helper system are generated as follows. These DNA fragments retain at least a portion of the transcribed region of the "late" transcription unit of the adenovirus genome and carry deletions in at least a portion of the E1 region and deletions in at least a portion of the encapsidation signal. In addition, these DNA fragments contain at least one copy of an ITR. At one terminus of the transfected DNA molecule an ITR is located. The other end may contain an ITR, or alternatively, a DNA sequence that is complementary to a portion of the same strand of the DNA molecule other than the ITR. If, in the latter case, the two complementary sequences anneal, the free 3'-hydroxyl group of the 3' terminal nucleotide of the hairpin-structure can serve as a primer for DNA synthesis by cellular and/or adenovirus-encoded DNA polymerases, resulting in conversion into a double-stranded form of at least a portion of the DNA molecule. Further replication initiating at the ITR will result in a linear double-stranded DNA molecule, that is flanked by two ITR's, and is larger than the original transfected DNA molecule (see FIG. 13). This molecule can replicate itself in the transfected cell by virtue of the adenovirus proteins encoded by the DNA molecule and the adenoviral and cellular proteins encoded by genes in the host-cell genome. This DNA molecule can not be encapsidated due to its large size (greater than 39000 base pairs) or due to the absence of a functional encapsidation signal. This DNA molecule is intended to serve as a helper for the production of defective adenovirus vectors in suitable cell lines.

The invention also comprises a method for amplifying linear DNA fragments of variable size in suitable mammalian cells. These DNA fragments contain at least one copy of the ITR at one of the termini of the fragment. The other end may contain an ITR, or alternatively, a DNA sequence that is complementary to a portion of the same strand of the DNA molecule other than the ITR. If, in the latter case, the two complementary sequences anneal, the free 3'-hydroxyl group of the 3' terminal nucleotide of the hairpin-structure can serve as a primer for DNA synthesis by cellular and/or adenovirus-encoded DNA polymerases, resulting in conversion of the displaced stand into a double stranded form of at least a portion of the DNA molecule. Further replication initiating at the ITR will result in a linear double-stranded DNA molecule, that is flanked by two ITR's, which is larger than the original transfected DNA molecule. A DNA molecule that contains ITR sequences at both ends can replicate itself in transfected cells by virtue of the presence of at least the adenovirus E2 proteins (viz. the DNA-binding protein ("DBP"), the adenovirus DNA polymerase ("Ad-pol"), and the pre-terminal protein ("pTP"). The required proteins may be expressed from adenovirus genes on the DNA molecule itself, from adenovirus E2 genes integrated in the host-cell genome, or from a replicating helper fragment as described above.

Several groups have shown that the presence of ITR sequences at the end of DNA molecules are sufficient to generate adenovirus minichromosomes that can replicate, if the adenovirus-proteins required for replication are provided in trans, for example, by infection with a helpervirus (Hu et al., 1992; Wang and Pearson, 1985; Hay et al., 1984). Hu et al. (1992) observed the presence and replication or symmetrical adenovirus minichromosome-dimers after transfection of plasmids containing a single ITR. The authors were able to demonstrate that these dimeric minichromosomes arise after tail-to-tail ligation of the single ITR DNA molecules. In DNA extracted from defective adenovirus type 2 particles, dimeric molecules of various sizes have also been observed using electron-microscopy (Daniell, 1976). It was suggested that the incomplete genomes were formed by illegitimate recombination between different molecules and that variations in the position of the sequence at which the illegitimate base pairing occurred were responsible for the heterogeneous nature of the incomplete genomes. Based on this mechanism it was speculated that, in theory, defective molecules with a total length of up to two times the normal genome could be generated. Such molecules could contain duplicated sequences from either end of the genome. However, no DNA molecules larger than the fill-length virus were found packaged in the defective particles (Daniell, 1976). This can be explained by the size-limitations that apply to the packaging. In addition, it was observed that in the virus particles DNA-molecules with a duplicated left-end predominated over those containing the right-end terminus (Daniell, 1976). This is fully explained by the presence of the encapsidation signal near that left-end of the genome (Gräble and Hearing, 1990; Gräble and Hearing, 1992; Hearing et al., 1987).

The major problems associated with the current adenovirus-derived vectors are:

1) The strong immunogenicity of the virus particle.
2) The expression of adenovirus genes that reside in the adenoviral vectors, resulting in a Cytotoxic T-cell response against the transduced cells.
3) The low amount of heterologous sequences that can be accommodated in the current vectors (Up to maximally approx. 8000 base pairs ("bp") of heterologous DNA).

The strong immunogenicity of the adenovirus particle results in an immunological response of the host, even after a single administration of the adenoviral vector. As a result of the development of neutralizing antibodies, a subsequent administration of the virus will be less effective or even completely ineffective. However, a prolonged or persistent expression of the transferred genes will reduce the number of administrations required and may bypass the problem.

With regard to problem 2), experiments performed by Wilson and collaborators have demonstrated that after adenovirus-mediated gene transfer into immunocompetent animals, the expression of the transgene gradually decreases and disappears approximately 2–4 weeks post-infection (Yang et al. 1994a; Yang et al., 1994b). This is caused by the development of a Cytotoxic T-Cell ("CTL") response against the transduced cells. The CTLs were directed against adenovirus proteins expressed by the viral vectors. In the transduced cells synthesis of the adenovirus DNA-binding protein (the E2A-gene product), penton and fiber proteins (late-gene products) could be established. These adenovirus proteins, encoded by the viral vector, were expressed despite deletion of the E1 region. This demonstrates that deletion of the E1 region is not sufficient to completely prevent expression of the viral genes (Engelhardt et al., 1994a).

With regard to problem 3), studies by Graham and collaborators have demonstrated that adenoviruses are capable of encapsidating DNA of up to 105% of the normal genome size (Bett et al., 1993). Larger genomes tend to be instable resulting in loss of DNA sequences during propagation of the virus. Combining deletions in the E1 and E3 regions of the virual genomes increases the maximum size of the foreign DNA that can be encapsidated to approximately 8.3 kb. In addition, some sequences of the E4 region appear to be dispensable for virus growth (adding another 1.8 kb to the maximum encapsidation capacity). Also the E2A region can be deleted from the vector, when the E2A gene product is provided in trans in the encapsidation cell line, adding another 1.6 kb. It is, however, unlikely that the maximum capacity of foreign DNA can be significantly increased further than 12 kb.

We developed a new strategy for the generation and production of helper-free-stocks of recombinant adenovirus vectors that can accommodate up to 38 kb of foreign DNA. Only two functional ITR sequences and sequences that can function as an encapsidation signal need to be part of the vector genome. Such vectors are called "minimal adenovectors." The helper functions for the minimal adenovectors are provided in trans by encapsidation defective-replication competent DNA molecules that contain all the viral genes encoding the required gene products, with the exception of those genes that are present in the host-cell genome, or genes that reside in the vector genome.

The applications of the disclosed inventions are outlined below and will be illustrated in the experimental part, which is only intended for that purpose, and should not be used to reduce the scope of the present invention as understood by the person skilled in the art.

Use of the IG packaging constructs Diploid cells.

The constructs, in particular pIG.E1A.E1B, will be used to transfect diploid human cells, such as HER, HEK, and Human Embryonic Lung cells ("HEL"). Transfected cells will be selected for transformed phenotype (focus formation) and tested for their ability to support propagation of E1-deleted recombinant adenovirus, such as IG.Ad.ML-PI.TK. Such cell lines will be used for the generation and (large-scale) production of E1-deleted recombinant adenoviruses. Such cells, infected with recombinant adenovirus are also intended to be used in vivo as a local producer of recombinant adenovirus, for example, for the treatment of solid tumors.

911 cells are used for the titration, generation and production of recombinant adenovirus vectors (Fallaux et al., 1996).

HER cells transfected with pIG.E1A.E1B have resulted in 7 independent clones (called PER cells). These clones are used for the production of E1-deleted (including non-overlapping adenovirus vectors) or E1 defective recombinant adenovirus vectors, and provide the basis for introduction of, for example, E2B or E2A constructs (e.g., ts125E2A, see below), E4 etc., that will allow propagation of adenovirus vectors that have mutations in, for example, E2A or E4.

In addition, diploid cells of other species that are permissive for human adenovirus, such as the cotton rat (*Sigmodon hispidus*) (Pacini et al., 1984), Syrian hamster (Morin et al., 1987) or chimpanzee (Levrero et al., 1991), will be immortalized with these constructs. Such cells, infected with recombinant adenovirus are also intended to be used in vivo for the local production of recombinant adenovirus, for example, for the treatment of solid tumors.

Established cells.

The constructs, in particular pIG.E1A.NEO, can be used to transfect established cells, for example, A549 (human bronchial carcinoma), KB (oral carcinoma), MRC-5 (human diploid lung cell line) or GLC cell lines (small cell lung cancer) (de Leij et al., 1985; Postmus et al., 1988) and selected for NEO resistance. Individual colonies of resistant cells are isolated and tested for their capacity to support propagation of E1-deleted recombinant adenovirus, such as IG.Ad.MLPI.TK. When propagation of E1-deleted viruses on E1A containing cells is possible, such cells can be used for the generation and production of E1-deleted recombinant adenovirus. They can also be used for the propagation of E1A deleted/E1B retained recombinant adenovirus Established cells can also be co-transfected with pIG.E1A.E1B and pIG.NEO (or another NEO containing expression vector). Clones resistant to G418 are tested for their ability to support propagation of E1-deleted recombinant adenovirus, such as IG.Ad.MLPI.TK and used for the generation and production of E1 deleted recombinant adenovirus and will be applied in vivo for local production of recombinant virus, as described for the diploid cells (see previous discussion). All cell lines, including transformed diploid cell lines or NEO-resistant established lines, can be used as the basis for the generation of 'next generation' packaging cells lines, that support propagation of E1-defective recombinant adenoviruses, that also carry deletions in other genes, such as E2A and E4. Moreover, they will provide the basis for the generation of minimal adenovirus vectors as disclosed herein.

E2 expressing cell lines

Packaging cells expressing E2A sequences are and will be used for the generation and large scale production of E2A-deleted recombinant adenovirus.

The newly generated human adenovirus packaging cell lines or cell lines derived from species permissive for human adenovirus (E2A or ts125E2A: E1A+E2A; E1A+E1B+E2A; E1A–E2A/ts125; E1A+E1B–E2A/ts125) or non-permissive cell lines such as monkey cells (hrE2A or hr+ts125E2A; E1A+hrE2A; E1A+E1B+hrE2A; E1A+hrE2A/ts125; E1A–E1B+hrE2A/ts125) are and will be used for the generation and large scale production of E2A deleted recombinant adenovirus vectors. In addition, they will be applied in vivo for local production of recombinant virus, as described for the diploid cells (see previous discussion).

Novel adenovirus vectors.

The newly developed adenovirus vectors harboring an E1 deletion of nt. 459–3510 will be used for gene transfer purposes. These vectors are also the basis for the development of further deleted adenovirus vectors that are mutated for, for example, E2A, E2B or E4. Such vectors will be generated, for example, on the newly developed packaging cell lines described above.

Minimal Adenovirus Packaging System

We disclose adenovirus packaging constructs (to be used for the packaging of minimal adenovirus vectors) which have the following characteristics:

1) the packaging construct replicates;
2) the packaging construct can not be packaged because the packaging signal is deleted;
3) the packaging construct contains an internal hairpin-forming sequence (see FIG. 15);
4) because of the internal hairpin structure, the packaging construct is duplicated, that is, the DNA of the packaging construct becomes twice as long as it was before transfection into the packaging cell (in our sample it duplicates from 35 kb to 70 kb). This duplication also prevents packaging. Note that this duplicated DNA molecule has ITR's at both termini (see, e.g., FIG. 13);
5) this duplicated packaging molecule is able to replicate like a 'normal adenovirus' DNA molecule;
6) the duplication of the genome is a prerequisite for the production of sufficient levels of adenovirus proteins, required to package the minimal adenovirus vector; and
7) the packaging construct has no overlapping sequences with the minimal vector or cellular sequences that may lead to generation of RCA by homologous recombination.

This packaging system is used to produce minimal adenovirus vectors. The advantages of minimal adenovirus vectors, for example, for gene therapy of vaccination purposes, are well known (accommodation of up to 38 kb; gutting of potentially toxic and immunogenic adenovirus genes).

Adenovirus vectors containing mutations in essential genes (including minimal adenovirus vectors) can also be propagated using this system.

Use of intracellular E2 expressing vectors.

Minimal adenovirus vectors are generated using the helper functions provided in trans by packaging-deficient replicating helper molecules. The adenovirus-derived ITR sequences serve as origins of DNA replication in the presence of at least the E2-gene products. When the E2 gene products are expressed from genes in the vector genome (the gene(s) must be driven by an E1-independent promoter), the vector genome can replicate in the target cells. This will allow a significantly increased number of template molecules in the target cells, and, as a result, an increased expression of the genes of interest encoded by the vector. This is of particular interest for application of gene therapy in cancer treatment.

Applications of intracellular amplification of linear DNA fragments.

A similar approach could also be taken if amplification of linear DNA fragments is desired. DNA fragments of known or unknown sequence could be amplified in cells containing the E2-gene products if at least one ITR sequence is located near or at its terminus. There are no apparent constraints on the size of the fragment. Even fragments much larger than the adenovirus genome (36 kb) should be amplified using this approach. It is thus possible to clone large fragments in mammalian cells without either shuttling the fragment into bacteria (such as *E. coli*) or use the polymerase chain reaction ("PCR"). At the end stage of an productive adenovirus infection a single cell can contain over 100,000 copies of the viral genome. In the optimal situation, the Linear DNA fragments can be amplified to similar levels. Thus, one should be able to extract more than 5 µg of DNA fragment per 10 million cells (for a 35-kbp fragment). This system can be used to express heterologous proteins equivalent to the Simian Virus 40-based COS-cell system) for research or for therapeutic purposes. In addition, the system can be used to identify genes in large fragments of DNA.

Random DNA fragments may be amplified (after addition of ITRs) and expressed during intracellular amplification. Election or selection of those cells with the desired phenotype can be used to enrich the fragment of interest and to isolate the gene.

EXPERIMENTAL

Generation of cell lines able to transcomplement E1 defective recombinant adenovirus vectors.

911 cell line

We have generated a cell line that harbors E1 sequences of adenovirus type 5 ("Ad5"), able to trans-complement E1 deleted recombinant adenovirus (Fallaux et al., 1996). This cell line was obtained by transfection of human diploid human embryonic retinoblasts ("HER") with pAd5XhoIC, that contains nt. 80–5788 of Ad5; one of the resulting transformants was designated 911. This cell line has been shown to be very useful in the propagation of E1 defective recombinant adenovirus. It was found to be superior to 293 cells. Unlike 293 cells, 911 cells lack a fully transformed phenotype, which most likely is the cause of its better performance as adenovirus packaging line:

1) plaque assays can be performed faster (4–5 days instead of 8–14 days on 293),
2) monolayers of 911 cells survive better under agar overlay as required for plaque assays, and
3) higher amplification of E1-deleted vectors is obtained.

In addition, unlike 293 cells that were transfected with sheared adenoviral DNA, 911 cells were transfected using a defined construct. Transfection efficiencies of 911 cells are comparable to those of 293.

New packaging constructs. Source of adenovirus sequences.

Adenovirus sequences are derived either from pAd5.SalB, containing nt. 80–9460 of human adenovirus type 5 (Bernards et al., 1983) or from wild-type Ad5 DNA. pAd5.SalB was digested with SalI and XhoI and the large fragment was religated and this new clone was named pAd5.X/S. The pTN construct (constructed bv Dr. R. Vogels, IntroGene, Leiden, The Netherlands) was used as a source for the human PGK promoter and the NEO gene.

Human PGK promoter and NEO$^R$ gene.

Transcription of E1A sequences in the new packaging constructs is driven by the human PGK promoter (Michelson et al., 1983; Singer-Sam et al., 1984), derived from plasmid pTN (gift of R. Vogels), which uses pUC119 (Vieira and Messing, 1987) as a backbone. This plasmid was also used as a source for NEO gene fused to the Hepatitis B Virus ("HBV") poly-adenylation signal.

Fusion of PGK promoter to E1 genes

Figure 1:
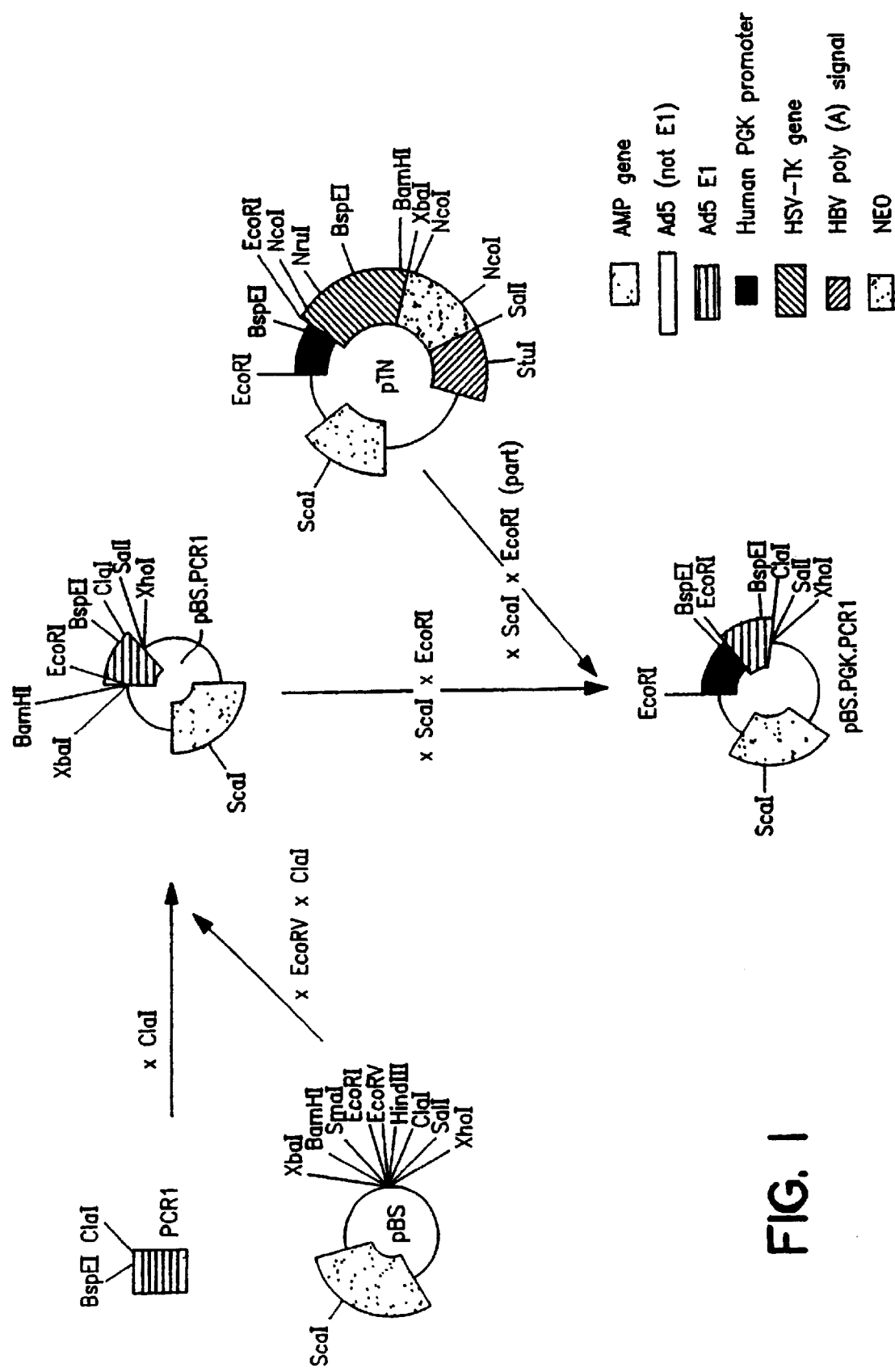
FIG. 1 illustrates the construction of pBS.PGK.PCRI.

As shown in FIG. 1, in order to replace the E1 sequences of Ad5 (ITR, origin of replication and packaging signal) by heterologous sequences we have amplified E1 sequences (nt.459 to nt. 960) of Ad5 by PCR, using primers Ea-1 (SEQ ID NO: 1) and Ea-2 (SEQ ID NO: 2) (see Table I). The resulting PCR product was digested with ClaI and ligated into Bluescript (Stratagene), predigested with ClaI and EcoRV, resulting in construct pBS.PCRI.

TABLE I

| Name (SEQ ID NO) | Sequence | Function |
| --- | --- | --- |
| Primer Ea-1 (SEQ ID NO: 1) | CGTGTAGTGT ATTTATACCC aG | PCR amplification Ad5 nt459 -> |
| Primer Ea-2 (SEQ ID NO: 2) | TCGTCACTGG GTGGAAAGCC aA | PCR amplification Ad5 nt960 <- |
| Primer Ea-3 (SEQ ID NO: 3) | TACCCGCCGT CCTAAAATGG aC | nt1284–1304 of Ad5 genome |
| Primer Ea-5 (SEQ ID NO: 4) | TGGACTTGAG CTGTAAACGC a | nt1514–1533 of Ad5 genome |
| Primer Ep-2 (SEQ ID NO: 5) | GCCT<u>CCATGG</u> AGGTCAGATG aT | nt1721–1702 of Ad5: introduction of NcoI site |
| Primer Eb-1 (SEQ ID NO: 6) | GCTTGAGCCC GAGACATGTC a | nt3269–3289 of Ad5 genome |
| Primer Eb-2 (SEQ ID NO: 7) | CCC<u>CTCGAGC</u> TCAATCTGTA aTCTT | nt3508–3496 of Ad5 genome: introduction of XhoI site |
| Primer SV40-1 (SEQ ID NO: 8) | GGG<u>GGATCCG</u> AACTTGTTTA aTTGCAGC | Introduction BamHI site (nt2182–2199 of pMLP.TK) adaption of recombinant adenoviruses |
| Primer SV40-2 (SEQ ID NO: 9) | GGG<u>AGATCTA</u> GACATGATAA aGATAC | Introduction BglII site (nt2312–2297 of pMLP.TK) |
| Primer Ad5-1 (SEQ ID NO: 10) | GGG<u>AGATCTG</u> TACTGAAATG aTGTGGGC | Introduction of BglII site (nt 2496–2514 of pMLP.TK) |

TABLE I-continued

| Name (SEQ ID NO) | Sequence | Function |
|---|---|---|
| Primer Ad5-2 (SEQ ID NO: 11) | GGAGGCTGCA GTCTCCAACG aGCGT | Rnt2779–2756 of pMLP.TK |
| Primer ITR1 (SEQ ID NO: 12) | GGGGGATCCT CAAATCGTCA aCTTCCGT | nt35737–35757 of Ad5 (introduction of BamHI site) |
| Primer ITR2 (SEQ ID NO: 13 | GGGGTCTAGA CATCATCAAT aAATATAC | nt35935–35919 of Ad5 (introduction of XbaI site) |
| PCR primer PCR/MLP1 (SEQ ID NO: 14) | GGCGAATTCG TCGACATCAT bCAATAATATA CC | (Ad5 nt. 10–18) |
| PCT primer PCR/MLP2 (SEQ ID NO: 15) | GGCGAATTCG GTACCATCAT bCAATAATATA CC | (Ad5 nt. 10–18) |
| PCT primer PCR/MLP3 (SEQ ID NO: 16) | CTGTGTACAC CGGCGCA b | (Ad5 nt. 200–184) |
| PCT primer HP/asp1 (SEQ ID NO: 17) | 5'-GTACACTGAC CTAGTGCCGC c CCGGGCAAAG CCCGGGCGGC ACTAGGTCAG | |
| PCT primer HP/asp2 (SEQ ID NO: 18) | 5'-GTACCTGACC TAGTGCCGCC c CGGGCTTTGC CCGGGCGGCA CTAGGTCAGT | |
| PCT primer HP/cla1 (SEQ ID NO: 19) | 5'-GTACATTGAC CTAGTGCCGC d CCGGGCAAAG CCCGGGCGGC ACTAGGTCAA TCGAT | |
| PCT primer HP/cla2 (SEQ ID NO: 20) | 5'-GTACATCGAT TGACCTAGTG d CCGCCCGGGC TTTGCCCGGG CGGCACTAGG TCAAT | |

Table I. Primer Sequences.
a - Primers used for PCR amplification of DNA fragments used for generation of constructs described in this patent application.
b - PCR primers sets to be used to create the SalI and Asp718 sites juxtaposed to the ITR sequences.
c - Synthetic oligonucleotide pair used to generate a synthetic hairpin, recreates an Asp718 site at one of the termini if inserted in Asp718 site.
d - Synthetic oligonucleotide pair used to generate a synthetic hairpin, contains the ClaI recognition site to be used for hairpin formation.

Figure 2:
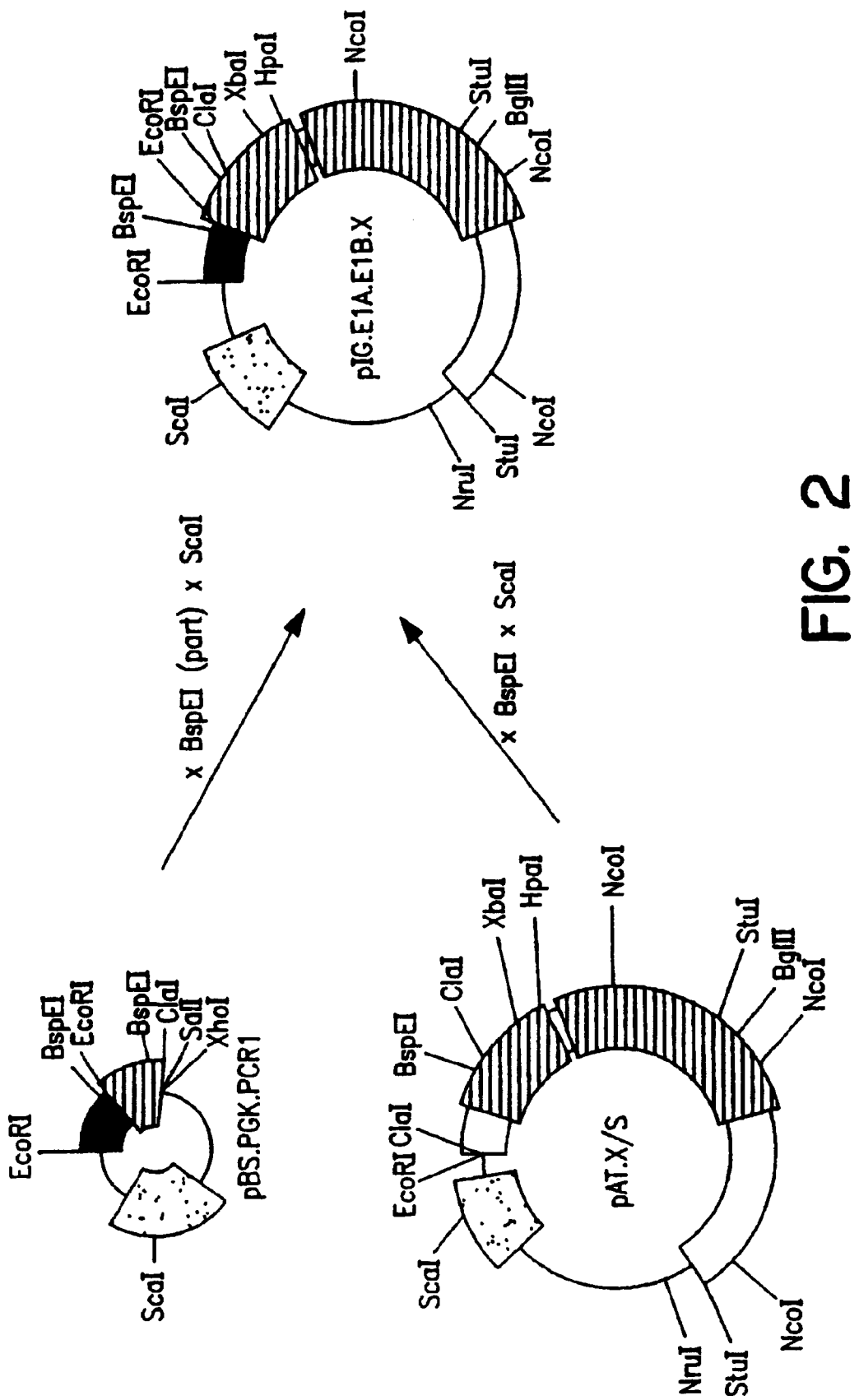
FIG. 2 illustrates the construction of pIG.E1A.E1B.X.
Figure 3A:
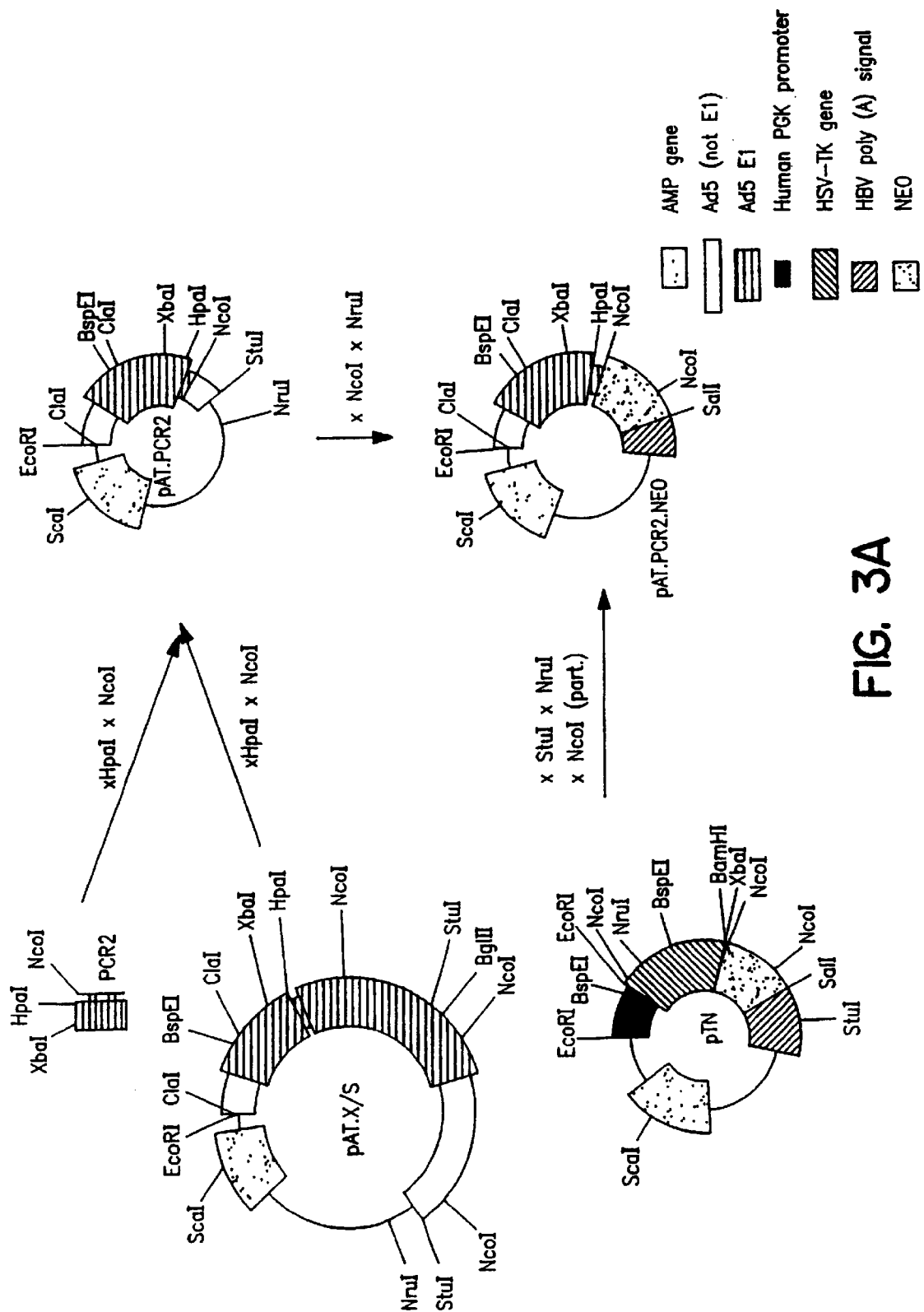
FIGS. 3A and 3B illustrate the construction of pIG.E1A.NEO.

Vector pTN was digested with restriction enzymes EcoRI (partially) and ScaI. and the DNA fragment containing the PGK promoter sequences was ligated into PBS.PCRI digested with ScaI and EcoRI. The resulting construct PBS.PGK.PCRI contains the human PGK promoter operatively linked to Ad5 E1 sequences from nt.459 to nt. 916.
Construction of pIG.E1A.E1B.X As shown in FIG. 2, pIG.E1A.E1B.X was made by replacing the ScaI-BspEI fragment of pAT-X/S by the corresponding fragment from PBS.PGK.PCRI (containing the PGK promoter linked to E1A sequences). pIG.E1A.E1B.X contains the E1A and E1B coding sequences under the direction of the PGK promoter. As Ad5 sequences from nt.459 to nt. 5788 are present in this construct, also pIX protein of adenovirus is encoded by this plasmid.
Construction of pIG.E1A.NEO As shown in FIG. 3A, in order to introduce the complete E1B promoter and to fuse this promoter in such a way that the AUG codon of E1B 21 kD exactly functions as the AUG codon of NEO$^R$, we amplified the E1B promoter using primers Ea-3 (SEQ ID NO: 3) and Ep-2 (SEQ ID NO: 5), where primer Ep-2 introduces an NcoI site in the PCR fragment. The resulting PCR fragment, named PCRII, was digested with HpaI and NcoI and ligated into pAT-X/S, which was predigested with HpaI and with NcoI. The resulting plasmid was designated pAT-X/S-PCR2. The NcoI-StuI fragment of pTN, containing the NEO gene and part of the HBV poly-adenylation signal, was cloned into pAT-X/S-PCR2 (digested with NcoI and NruI). The resulting construct: pAT-PCR2-NEO.

Figure 3B:
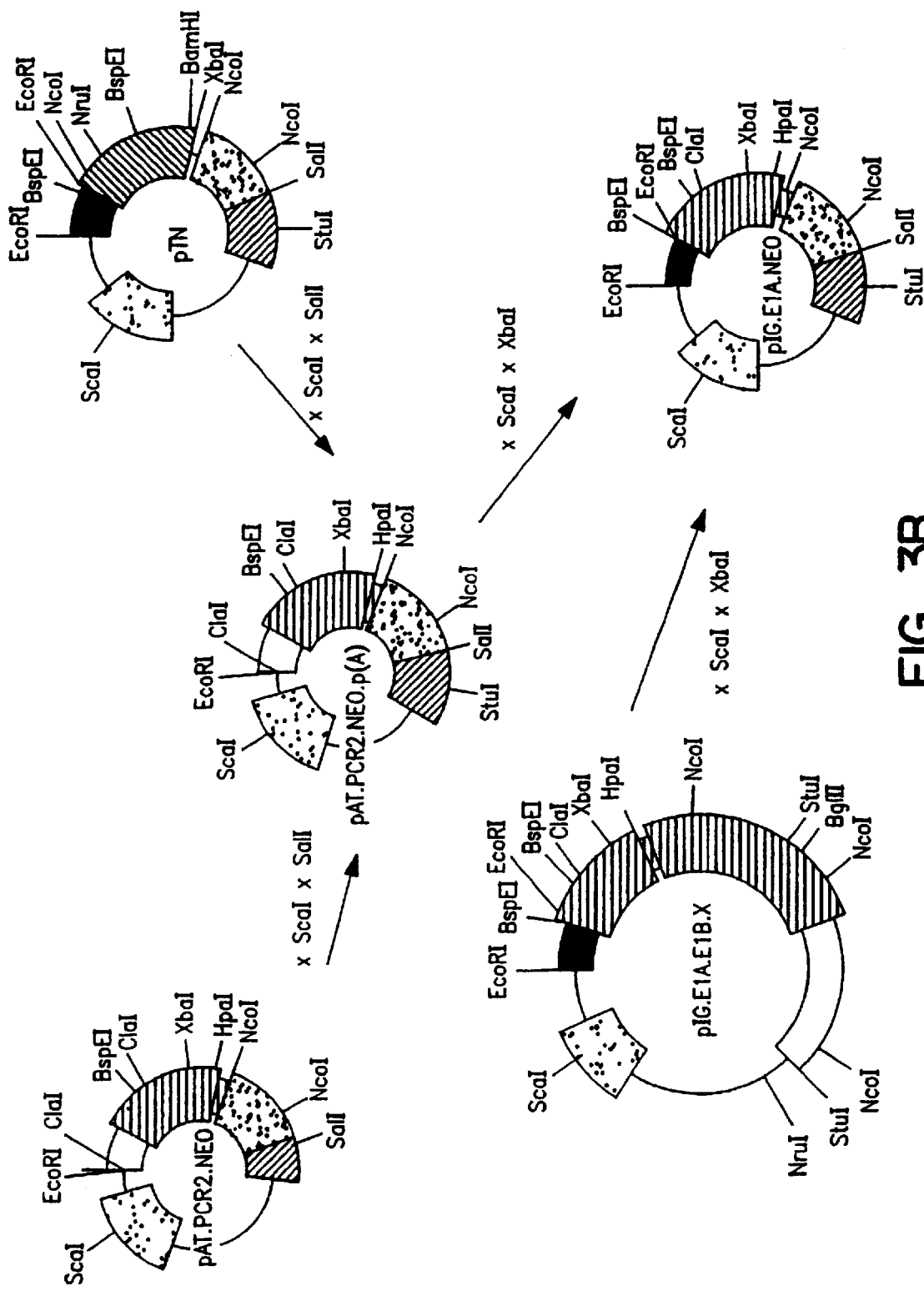
Figure 4A:
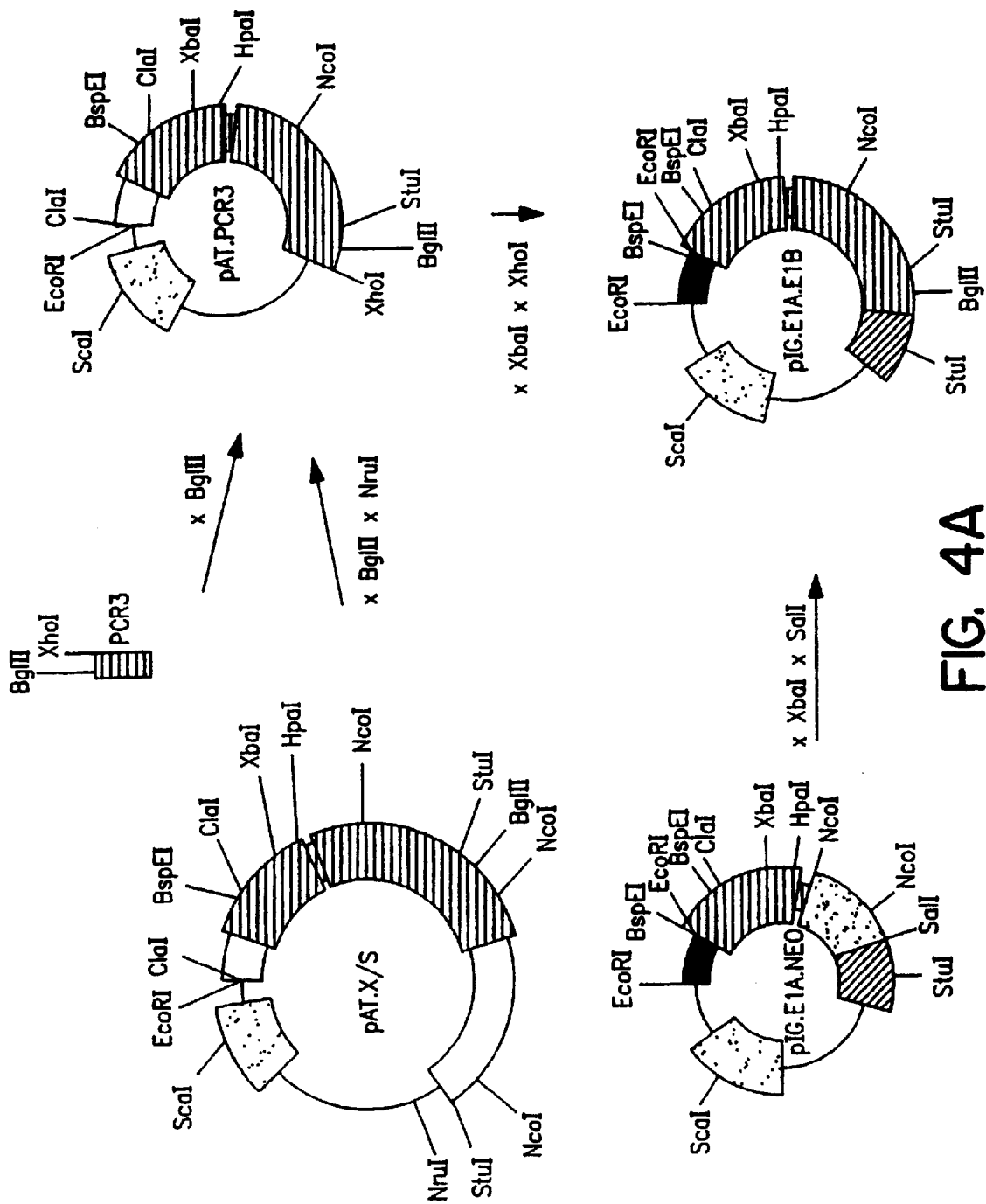
FIGS. 4A and 4B illustrate the construction of pIG.E1A.E1B.
Figure 4B:
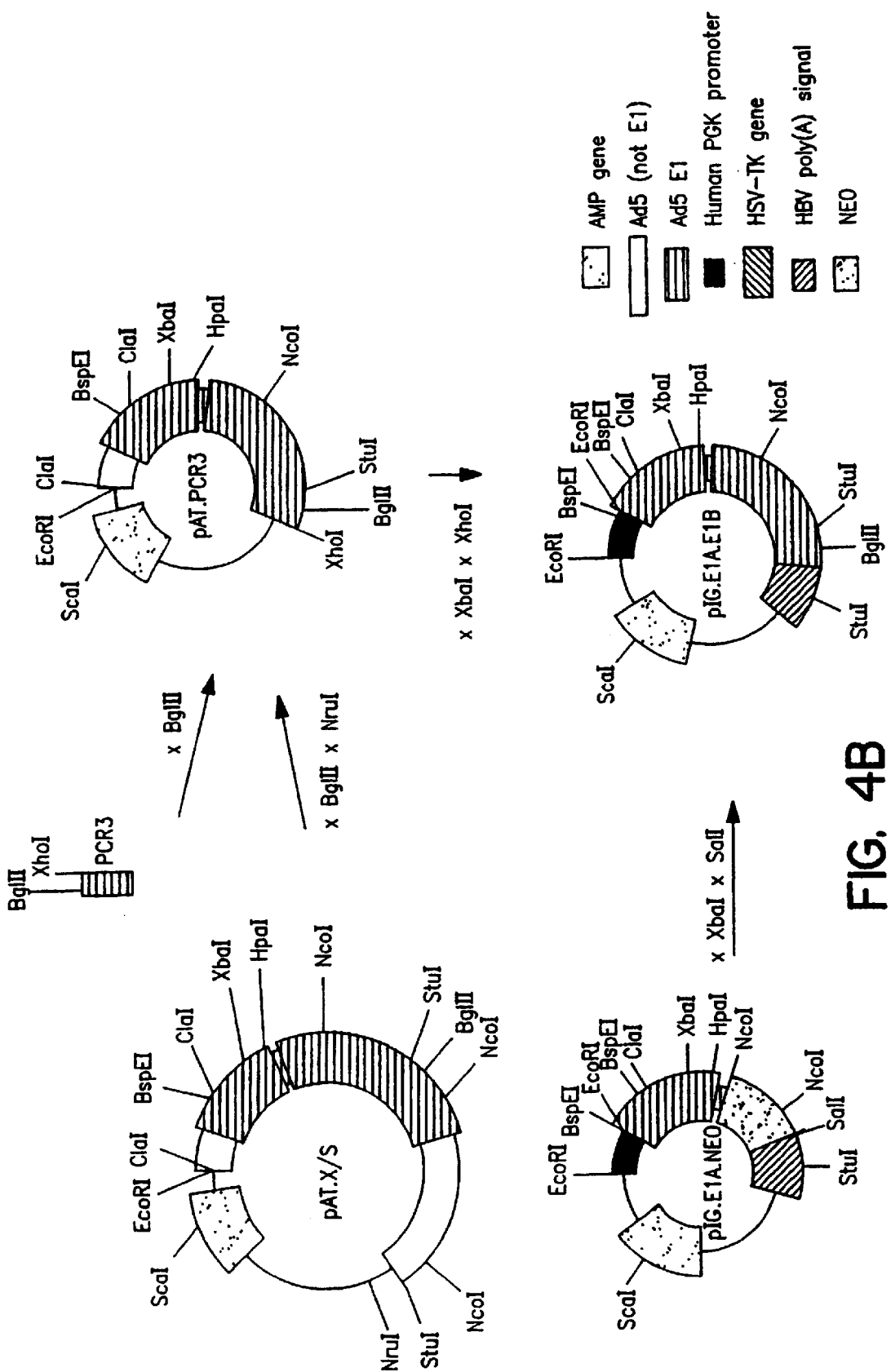

As shown in FIG. 3B, the poly-adenylation signal was completed by replacing the ScaI-SalI fragment of pAT-PCR2-NEO by the corresponding fragment of pTN (resulting in pAT.PCR2.NEO.p(A)). The ScaI-XbaI of pAT.PCR2.NEO.p (A) was replaced by the corresponding fragment of pIG.E1A.E1B-X, containing the PGK promoter linked to E1A genes. The resulting construct was named pIG.E1A.NEO, and thus contains Ad5 E1 sequences (nt.459 to nt 1713) under the control of the human PGK promoter.
Construction of pIG.E1A.E1B As shown in FIG. 4, pIG.E1A.E1B was made by amplifying the sequences encoding the N-terminal amino acids of E1B 55 kd using primers Eb-1 (SEQ ID NO: 6) and Eb-2 (SEQ ID NO: 7) (introduces a XhoI site). The resulting PCR fragment was digested with BglII and cloned into BglII/NruI of pAT-X/S, thereby obtaining pAT-PCR3.

pIG.E1A.E1B was constructed by introducing the HBV poly(A) sequences of pIG.E1A.NEO downstream of E1B sequences of pAT-PCR3 by exchange of XbaI-SalI fragment of pIg.E1A.NEO and the XbaI XhoI fragment of pAT.PCR3.

pIG.E1A.E1B contains nt. 459 to nt. 3510 of Ad5, that encode the E1A and E1B proteins. The E1B sequences are terminated at the splice acceptor at nt.3511. No pIX sequences are present in this construct.

Construction of pIG.NEO

Figure 5:
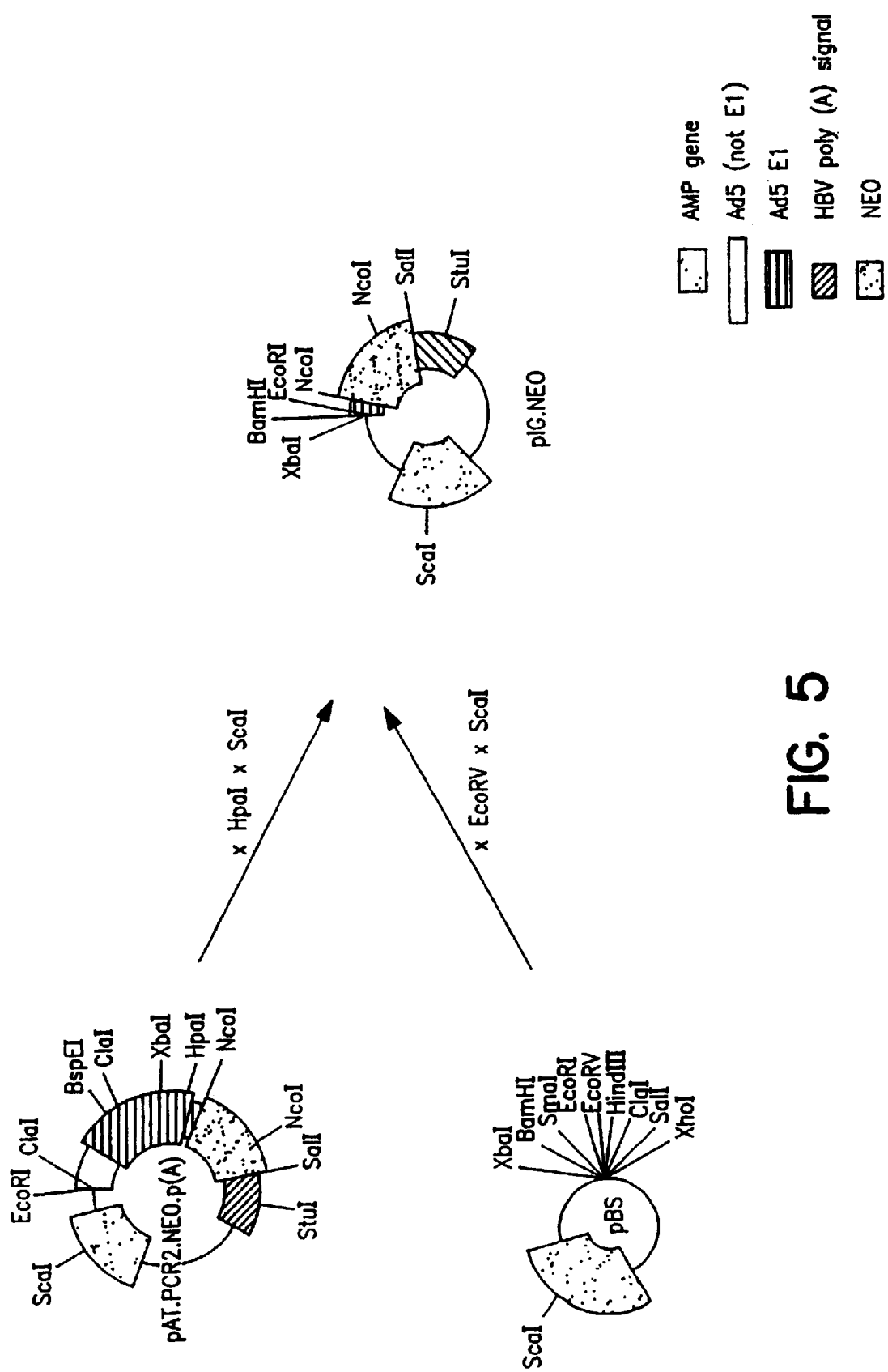
FIG. 5 illustrates the construction of pIG.NEO.

As shown in FIG. 5, pIG.NEO was generated by cloning the HpaI-ScaI fragment of pIG.E1A.NEO, containing the NEO gene under the control of the Ad.5 E1B promoter, into pBS digested with EcoRV and ScaI.

This construct is of use when established cells are transfected with E1A.E1B constructs and NEO selection is required. Because NEO expression is directed by the E1B promoter, NEO resistant cells are expected to co-express E1A, which also is advantageous for maintaining high levels of expression of E1A during long-term culture of the cells.

Testing of constructs.

The integrity of the constructs pIG.E1A.NEO, pIG.E1A.E1B.X and pIG.E1A.E1B was assessed by restriction enzyme mapping; furthermore, parts of the constructs that were obtained by PCR analysis were confirmed by sequence analysis. No changes in the nucleotide sequence were found.

The constructs were transfected into primary Baby Rat Kidney ("BRK") cells and tested for their ability to immortalize (pIG.E1A.NEC) or fully transform (pAd5.XhoIC, pIG.E1A.E1B.X and pIG.E1A.E1B) these cells.

Kidneys of 6-day old WAG-Rij rats were isolated, homogenized and trypsinized. Subconfluent dishes (diameter 5 cm) of the BRK cell cultures were transfected with 1 or 5 µg of pIG.NEO, pIG.E1A.NEO, pIG.E1A.E1B, pIG.E1A.E1B.X, pAd5XhoIC, or with pIG.E1A.NEO together with PDC26 (Van der Elsen et al., 1983), carrying the Ad5.E1B gene under control of the SV4O early promoter. Three weeks post-transfection, when foci were visible, the dishes were fixed, Giemsa stained and the foci counted.

Figure 6:
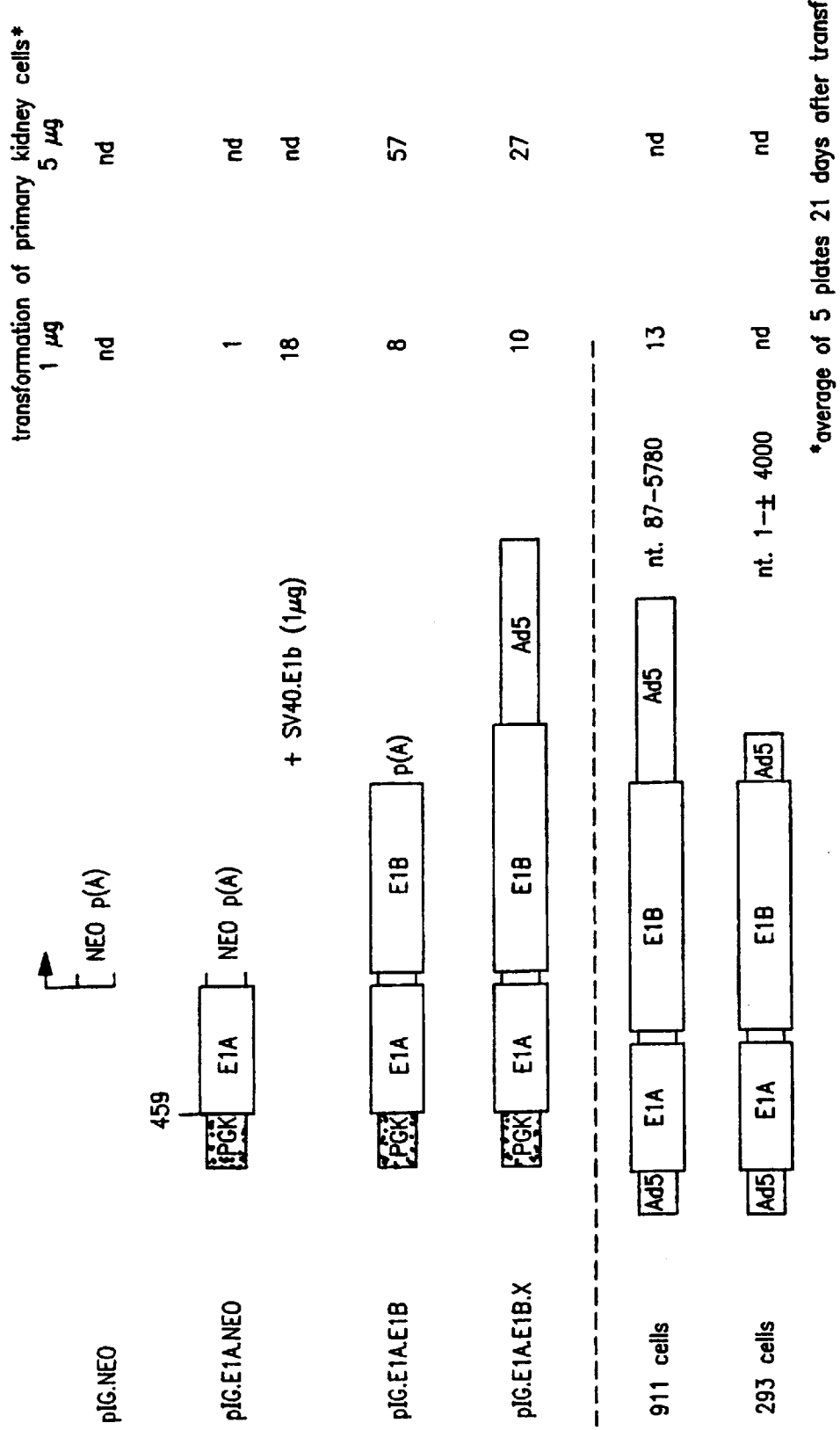
FIG. 6 illustrates the transformation of primary baby rat kidney ("BRK") cells by adenovirus packaging constructs.

An overview of the generated adenovirus packaging constructs, and their ability to transform BRK, is presented in FIG. 6. The results indicate that the constructs pIG.E1A.E1B and pIG.E1A.E1B.X are able to transform BRK cells in a dose-dependent manner. The efficiency of transformation is similar for both constructs and is comparable to what was found with the construct that was used to make 911 cells, namely pAd5. XhoIC.

As expected, pIG.E1A.NEO was hardly able to immortalize BRK. However, co-transfection of an E1B expression construct (PDC26) did result in a significant increase of the number of transformants (18 versus 1), indicating that E1A encoded by pIG.E1A.NEO is functional. We conclude, therefore, that the newly generated packaging constructs are suited for the generation of new adenovirus packaging lines.

Generation of cell lines with new packaging constructs Cell lines and cell culture Human A549 bronchial carcinoma cells (Shapiro et al., 1978), human embryonic retinoblasts ("HER"), Ad5-E1-transformed human embryonic kidney ("HEK") cells (293; Graham et al., 1977) cells and Ad5-transformed HER cells (911; Fallaux et al., 1996)) and PER cells were grown in Dulbecco's Modified Eagle Medium ("DMEM") supplemented with 10% Fetal Calf Serum ("FCS") and antibiotics in a 5% CO2 atmosphere at 37° C. Cell culture media, reagents and sera were purchased from Gibco Laboratories (Grand Island, N.Y.). Culture plastics were purchased from Greiner (Nürtingen, Germany) and Corning (Corning, N.Y.).

Viruses and virus techniques

The construction of adenoviral vectors IG.Ad.MLP.nls.lacZ, IG.Ad.MLP.luc, IG.Ad.MLP.TK and IG.Ad.CMV.TK is described in detail in patent application EP 95202213. The recombinant adenoviral vector IG.Ad-.MLP.nls.lacZ contains the E. coli lacZ gene, encoding β-galactosidase, under control of the Ad2 major late promoter ("MLP"). IG.Ad.MLP.luc contains the firefly luciferase gene driven by the Ad2 MLP. Adenoviral vectors IG.Ad.MLP.TK and IG.Ad.CMV.TR contain the Herpes Simplex Virus thymidine kinase ("TK") gene under the control of the Ad2 MLP and the Cytomegalovirus ("CMV") enhancer/promoter, respectively.

Transfections

All transfections were performed by calcium-phosphate precipitation DNA (Graham and Van der Eb, 1973) with the GIBCO Calcium Phosphate Transfection System (GIBCO BRL Life Technologies Inc., Gaithersburg, Md., USA), according to the manufacturers protocol.

Western blotting

Subconfluent cultures of exponentially growing 293,911 and Ad5-E1-transformed A549 and PER cells were washed with PBS and scraped in Fos-RIPA buffer (10 mM Tris (pH 7.5), 150 mM NaCl, 1% NP4O,01% sodium dodecyl sulphate ("SDS"), 1% NA-DOC, 0.5 mM phenyl methyl sulphonyl fluoride ("PMSF"), 0.5 mM trypsin inhibitor, 50 mM NaF and 1 mM sodium vanadate). After 10 minutes at room temperature, lysates were cleared by centrifugation. Protein concentrations were measured with the Biorad protein assay kit, and 25 µg total cellular protein was loaded on a 12.5% SDS-PAA gel. After electrophoresis, proteins were transferred to nitrocellulose (1 hour at 300 mA). Prestained standards (Sigma, USA) were run in parallel. Filters were blocked with 1% bovine serum albumin ("BSA") in TBST (10 mM Tris, pH 8.15 mM NaCl, and 0.05% TWEEN™-20) for 1 hour. First antibodies were the mouse monoclonal anti-Ad5-E1B-55-kDA antibody AlC6 (Zantema et al., unpublished), the rat monoclonal anti-Ad5-E1B-221-kDa antibody ClGll (Zantema et al., 1985). The second antibody was a horseradish peroxidase-labeled goat anti-mouse antibody (Promega). Signals were visualized by enhanced chemoluminescence (Amersham Corp, UK).

Southern blot analysis

High molecular weight DNA was isolated and 10 µg was digested to completion and fractionated on a 0.7% agarose gel. Southern blot transfer to Hybond N+ (Amersham, UK) was performed with a 0.4 M NAOH, 0.6 M NaCl transfer solution (Church and Gilbert, 1984). Hybridization was performed with a 2463-nt SspI-HindIII fragment from pAd5.Sa1B (Bernards et al., 1983). This fragment consists of Ad5 bp. 342–2805. The fragment was radiolabeled with α-$^{32}$P-dCTP with the use of random hexanucleotide primers and Klenow DNA polymerase. The southern blots were exposed to a Kodak XAR-5 film at −80° C. and to a Phospho-Imager screen which was analyzed by B&L systems Molecular Dynamics software.

A549

Ad5-E1-transformed A549 human bronchial carcinoma cell lines were generated by transfection with pIG.E1A.NEO and selection for G418 resistance. Thirty-one G418 resistant clones were established. Co-transfection of pIG.E1A.E1B with pIG.NEO yielded seven G418 resistant cell lines.

PER

Ad5-E1-transformed HER cells were generated by transfection of primary HER cells with plasmid pIG.E1A.E1B. Transformed cell lines were established from well-separated foci. We were able to establish seven clonal cell lines which we called PER.C1, PER.C3, PER.C4, PER.C5, PER.C6, PER.C8 and PER.C9. One of the PER clones, namely PER.C6, has been deposited under the Budapest Treaty under number ECACC 96022940. In addition, PER.C6 is commercially available from IntroGene, B.V., Leiden, NL.
Expression of Ad5 E1A and E1B genes in transformed A549 and PER cells Expression of the Ad5 E1A and the 55-kDa and 21 kDa E1B proteins in the established A549 and PER cells was studied by means of Western blotting, with the use of monoclonal antibodies ("Mab"). Mab M73 recognizes the E1A products, whereas Mabs AIC6 and ClGll are directed against the 55-kDa and 21 kDa E1B proteins, respectively.

Figure 7:
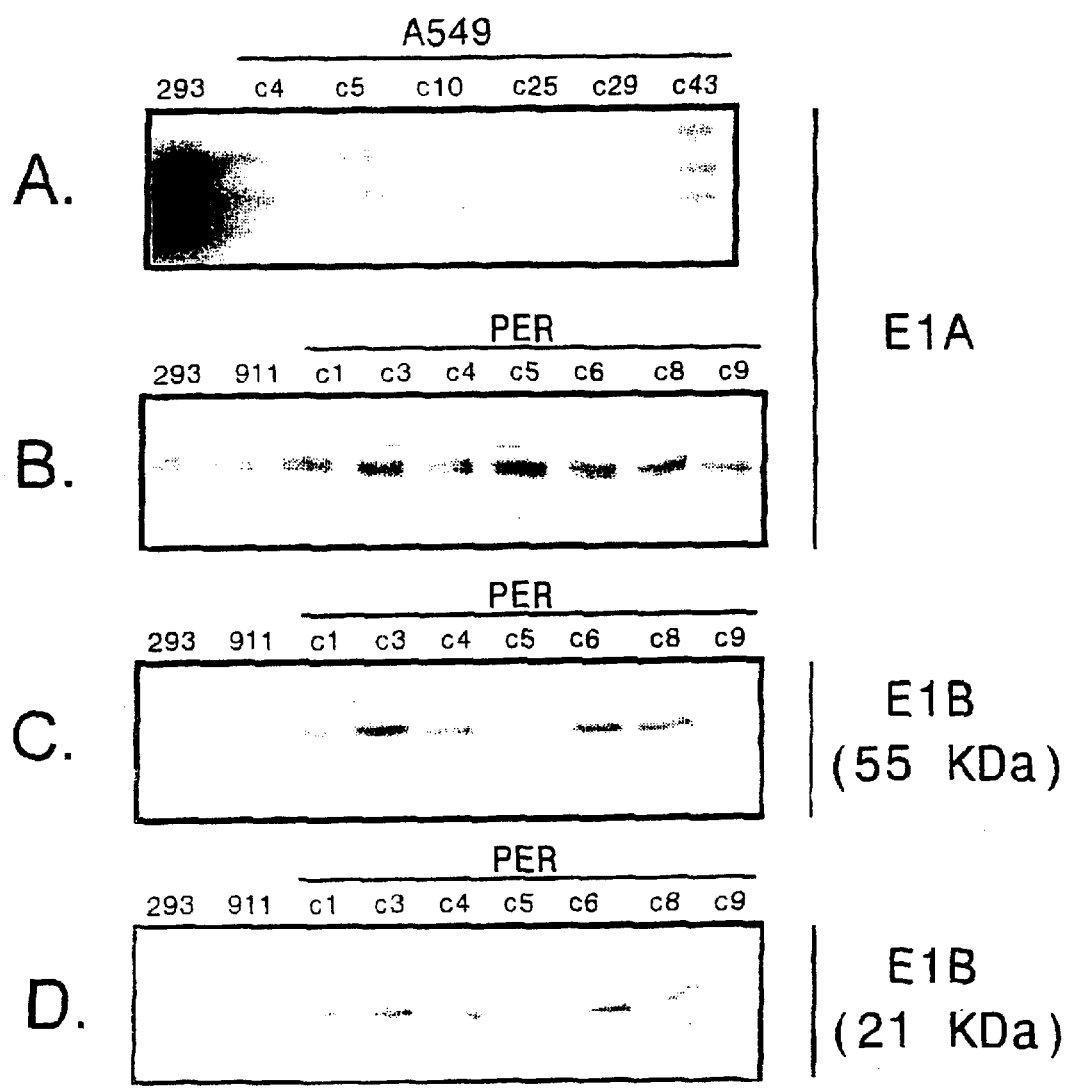
FIGS. 7A through 7D illustrate a Western blot analysis of A549 clones transfected with pIG.E1A.NEO and HER cells transfected with pIG.E1A.E1B (PER clones).

The antibodies did not recognize proteins in extracts from the parental A549 or the primary HER cells (data not shown). None of the A549 clones that were generated by co-transfection of pIG.NEO and pIG.E1A.E1B expressed detectable levels of E1A or E1B proteins (not shown). Some of the A549 clones that were generated by transfection with pIG.E1A.NEO expressed the Ad5 E1A proteins (FIG. 7), but the levels were much lower than those detected in protein lysates from 293 cells. The steady state E1A levels detected in protein extracts from PER cells were much higher than those detected in extracts from A549-derived cells. All PER cell lines expressed similar levels of E1A proteins (FIG. 7). The expression of the E1B proteins, particularly in the case of E1B 55 kDa, was more variable. Compared to 911 and 293, the majority of the PER clones express high levels of E1B 55 kDa and 21 kDa. The steady state level of E1B 21 kDa was the highest in PER.C3. None of the PER clones lost expression of the Ad5 E1 genes upon serial passage of the cells (not shown). We found that the level of E1 expression in PER cells remained stable for at least 100 population doublings. We decided to characterize the PER clones in more detail.

Southern analysis of PER clones

Figure 8:
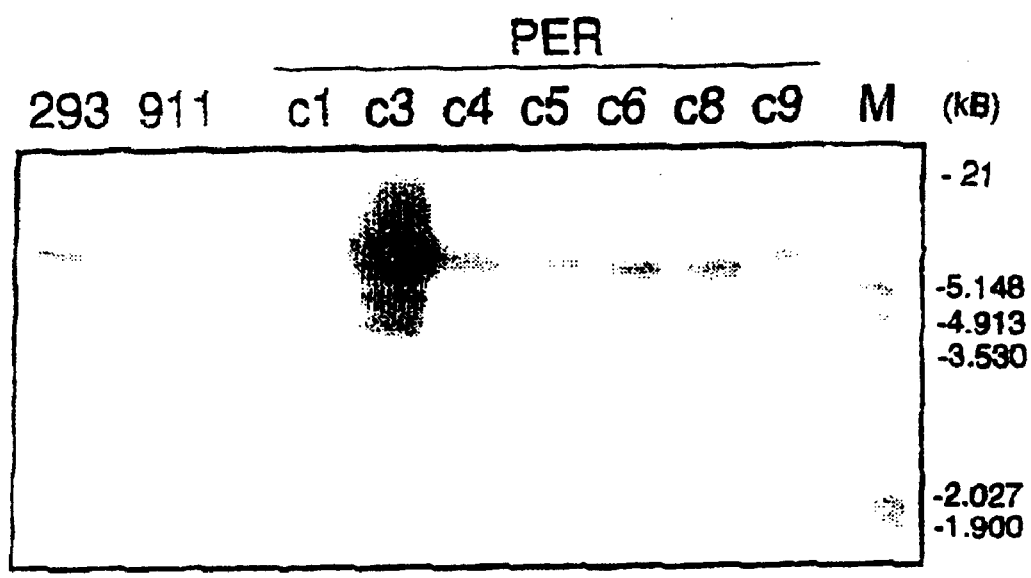
FIG. 8 illustrates a Southern blot analysis of 293, 911 and PER cell lines. Cellular DNA was extracted, Hind III digested, electrophoresed and transferred to Hybond N+ membranes (Amersham).

To study the arrangement of the Ad5-E1 encoding sequences in the PER clones we performed Southern analyses. Cellular DNA was extracted from all PER clones, and from 293 and 911 cells. The DNA was digested with HindIII, which cuts once in the Ad5 E1 region. Southern hybridization on HindIII-digested DNA, using a radiolabeled Ad5-E1-specific probe revealed the presence of several integrated copies of pIG.E1A.E1B in the genome of the PER clones. FIG. 8 shows the distribution pattern of E1 sequences in the high molecular weight DNA of the different PER cell lines. The copies are concentrated in a single band, which suggests that they are integrated as tandem repeats. In the case of PER.C3, C5, C6 and C9 we found additional hybridizing bands of low molecular weight that indicate the presence of truncated copies of pIG.E1A.E1B. The number of copies was determined with the use of a Phospho-Imager. We estimated that PER.C1, C3, C4, C5, C6, C8 and C9 contain 2, 88, 5,4, 5, 5 and 3 copies of the Ad5 E1 coding region, respectively, and that 911 and 293 cells contain 1 and 4 copies of the Ad5 E1 sequences, respectively.

Transfection efficiency

Figure 9:
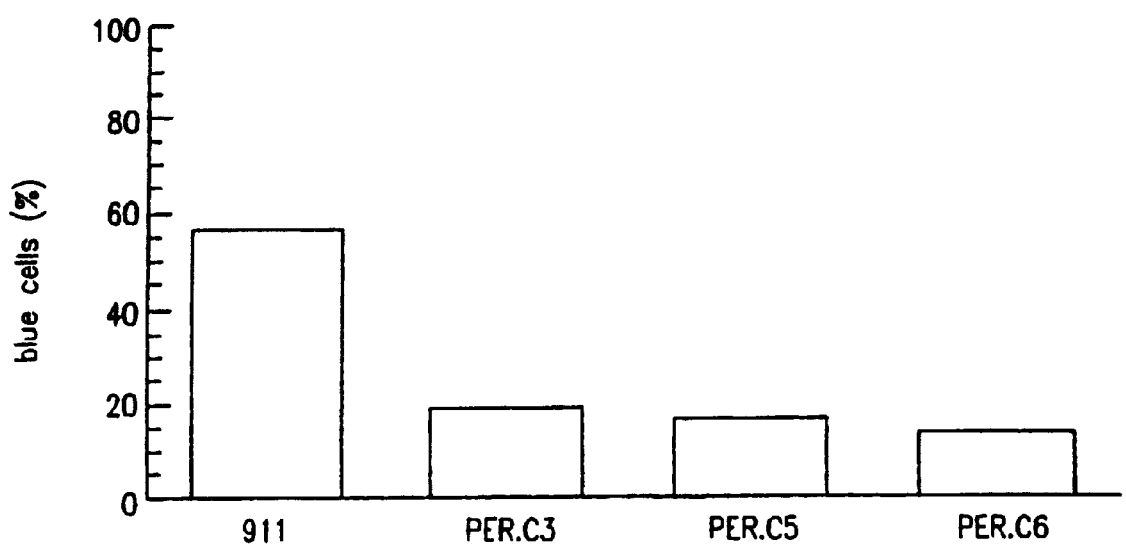
FIG. 9 illustrates the transfection efficiency of PER.C3, PER.C5, PER.C6™ and 911 cells.

Recombinant adenovectors are generated by co-transfection of adaptor plasmids and the large ClaI fragment of Ad5 into 293 cells (see European Patent Office ("EPO") application EP 95202213). The recombinant virus DNA is formed by homologous recombination between the homologous viral sequences that are present in the plasmid and the adenovirus DNA. The efficacy of this method, as well as that of alternative strategies, is highly dependent on the transfectability of the helper cells. Therefore, we compared the transfection efficiencies of some of the PER clones with 911 cells, using the $E.\ coli$ β-galactosidase-encoding lacZ gene as a reporter (FIG. 9).

Production of recombinant adenovirus

Yields of recombinant adenovirus obtained after inoculation of 293, 911, PER-C3, PER.C5 and PER.C6 with different adenovirus vectors are presented in Table II. The results indicate that the yields obtained on PER cells are at least as high as those obtained on the existing cell lines. In addition, the yields of the novel adenovirus vector IG.Ad.MLPI.TK are similar or higher than the yields obtained for the other viral vectors on all cell lines tested.

TABLE II

| Cell | Passage number | IG.Ad. CMV.lacZ | IG.Ad. CMV.TK | IG.Ad. MLPI.TK | d1313 | Producer Mean |
|---|---|---|---|---|---|---|
| 293 |  | 6.0 | 5.8 | 24 | 34 | 17.5 |
| 911 |  | 8 | 14 | 34 | 180 | 59.5 |
| PER.C3 | 17 | 8 | 11 | 44 | 40 | 25.8 |
| PER.C5 | 15 | 6 | 17 | 36 | 200 | 64.7 |
| PER.C6 | 36 | 10 | 22 | 58 | 320 | 102 |

Yields × $10^{-8}$ pfu/T175 flask.

Table II. Yields of different recombinant adenoviruses obtained after inoculation of adenovirus E1 packaging cell lines 293, 911, PER.C3, PER.C5 and PER.C6. The yields are the mean of two different experiments. IG.Ad.CMV.lacZ and IG.Ad.CMV.TK are described in patent application EP 95 20 2213. The construction of IG.Ad.MLPI.TK is described in this patent application. Yields of virus per T80 flask were determined by plaque assay on 911 cells, as described [Fallaux, 1996 #1493]

Generation of new adenovirus vectors

The used recombinant adenovirus vectors (see EPO patent application no. EP 95202213) are deleted for E1 sequences from 459 to nt. 3328.

Figure 10:
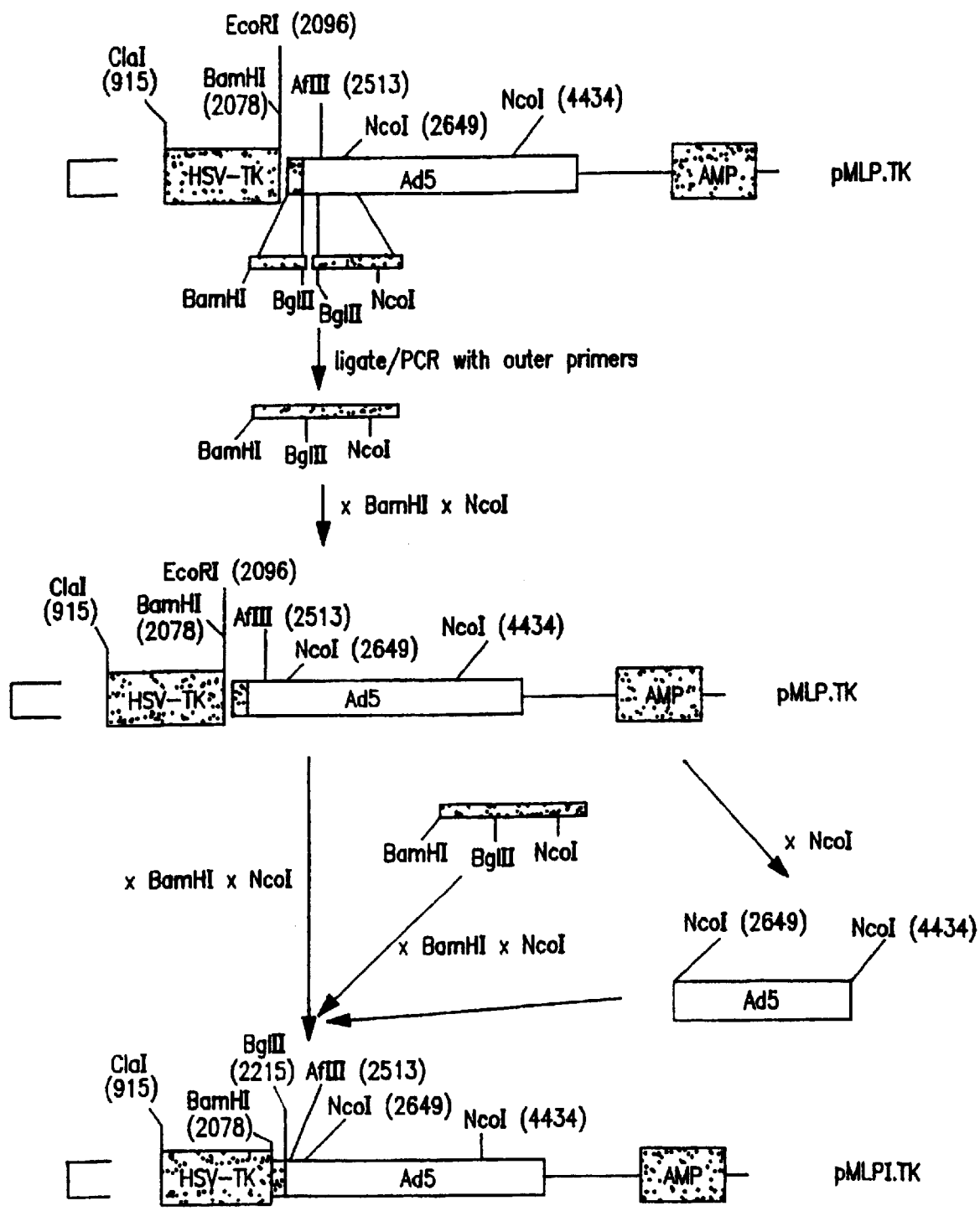
FIG. 10 illustrates construction of adenovirus vector, pMLPI.TK. pMLPI.TK designed to have no sequence overlap with the packaging construct pIG.E1A.E1B.

As construct pE1A.E1B contains Ad5 sequences 459 to not 3510 there is a sequence overlap of 183 nt. between E1B sequences in the packaging construct pIG.E1A.E1B and recombinant adenoviruses, such as, for example, IG.Ad.M-LP.TK. The overlapping sequences were deleted from the new adenovirus vectors. In addition, non-coding sequences derived from lacZ, that are present in the original constructs, were deleted as well. This was achieved (see FIG. 10) by PCR amplification of the SV4O poly(A) sequences from pMLP.TK using primers SV40-1 (SEQ ID NO: 8) (introduces a BamHI site) and SV40-2 (SEQ ID NO: 9) (introduces a BglII site). In addition, Ad5 sequences present in this construct were amplified from nt 2496 (Ad5-1 (SEQ ID NO: 10), introduces a BglII site) to nt. 2779 (Ad5-2 (SEQ ID NO: 11)). Both PCR fragments were digested with BglII and were ligated. The ligation product was PCR amplified using primers SV40-1 and Ad5-2. The PCR product obtained was cut with BamHI and AflII and was ligated into pMLP.TK predigested with the same enzymes. The resulting construct, named pMLPI.TK, contains a deletion in adenovirus E1 sequences from nt 459 to nt. 3510.

Packaging system

The combination of the new packaging construct pIG.E1A.E1B and the recombinant adenovirus pMLPI.TK, which do not have any sequence overlap, are presented in FIGS. 11A and 11B. In these figures, the original situation is also presented, with the sequence overlap indicated.

The absence of overlapping sequences between pIG.E1A.E1B and pMLPI.TK (FIG. 11A) excludes the possibility of homologous recombination between packaging construct and recombinant virus, and is therefore a significant improvement for production of recombinant adenovirus as compared to the original situation.

In FIG. 11B the situation is depicted for pIG.E1A.NEO and IG.Ad.MLPI.TK. pIG.E1A.NEO, when transfected into established cells, is expected to be sufficient to support propagation of E1-deleted recombinant adenovirus. This combination does not have any sequence overlap, preventing generation of RCA by homologous recombination. In addition, this convenient packaging system allows the propagation of recombinant adenoviruses that are deleted just for E1A sequences and not for E1B sequences. Recombinant adenoviruses expressing E1B in the absence of E1A are attractive, as the E1B protein, in particular E1B 19 kD, is able to prevent infected human cells from lysis by Tumor Necrosis Factor ("TNF") (Gooding et al., 1991).

Generation of recombinant adenovirus derived from pMLPI.TK.

Figure 12:
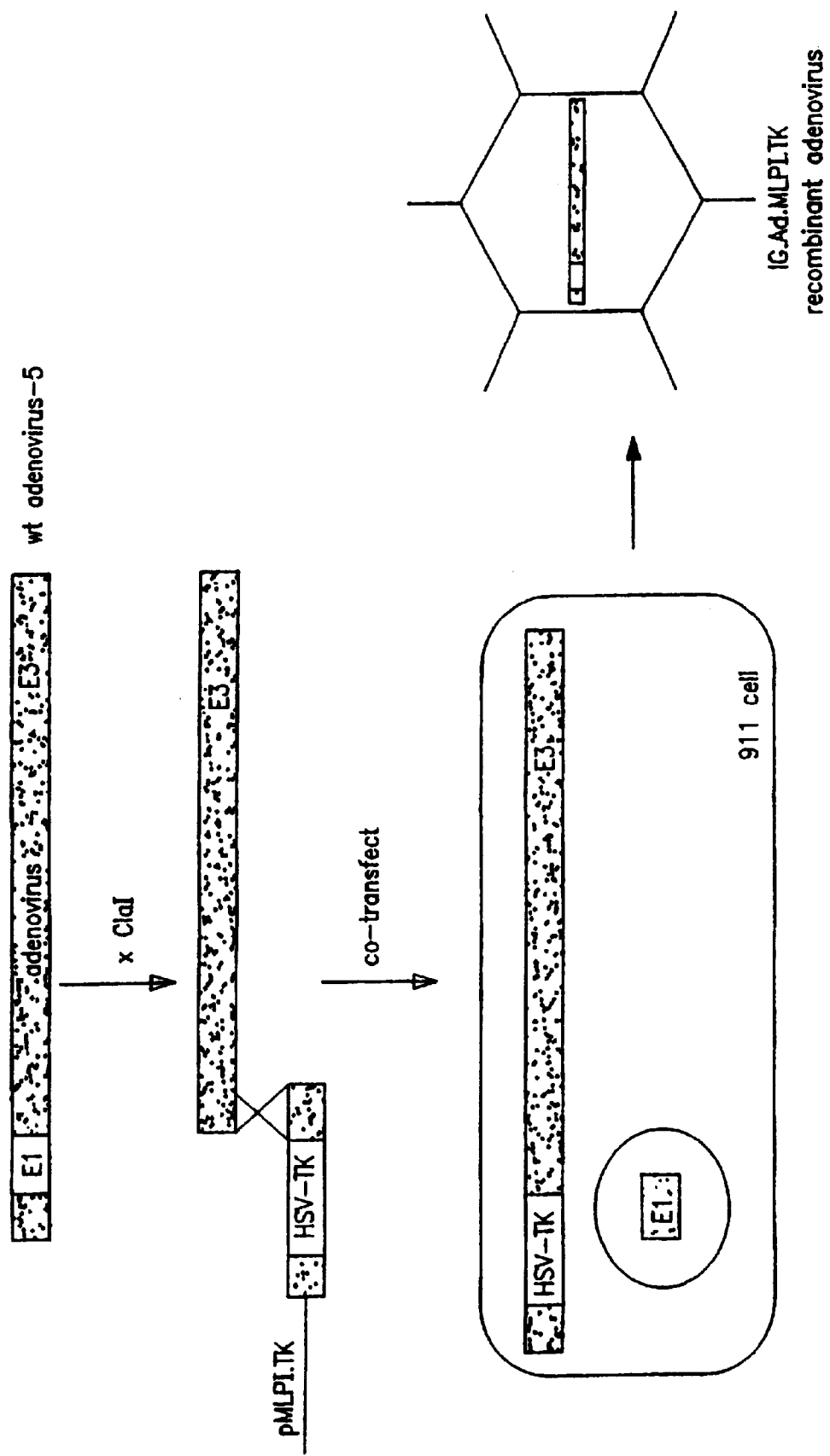
FIG. 12 illustrate the generation of recombinant adenovirus, IG.Ad.MLPI.TK.

Recombinant adenovirus was generated by co-transfection of 293 cells with SalI linearized pMLPI.TK DNA and ClaI linearized Ad5 wt DNA. The procedure is schematically represented in FIG. 12.

Outline of the strategy to generate packaging systems for minimal adenovirus vector Name convention of the plasmids used:

p plasmid

I ITR (Adenovirus Inverted Terminal Repeat)

C CMV Enhancer/Promoter Combination

L Firefly Luciferase Coding Sequence hac,haw Potential hairpin that can be formed after digestion with restriction endonuclease Asp718 in its correct and in the reverse orientation, respectively (FIG. 15 (SEQ ID NO: 22)).

For example, pICLhaw is a plasmid that contains the adenovirus ITR followed by the CMV-driven luciferase gene and the Asp718 hairpin in the reverse (non-functional) orientation.

Experiment Series 1

The following demonstrates the competence of a synthetic DNA sequence that is capable of forming a hairpin-structure to serve as a primer for reverse strand synthesis for the generation of double-stranded DNA molecules in cells that contain and express adenovirus genes.

Plasmids pICLhac, pICLhaw, pICLI and pICL were generated using standard techniques. The schematic representation of these plasmids is shown in FIGS. 16–19.

Plasmid pICL is derived from the following plasmids:

nt.1–457 pMLP10 (Levrero et al., 1991)

nt.458–1218 pCMVβ (Clontech, EMBL Bank No. U02451)

nt.1219–3016 pMLP.luc (IntroGene, Leiden, NL, unpublished)

nt3017–5620 pBLCAT5 (Stein and Whelan, 1989)

Figure 19:
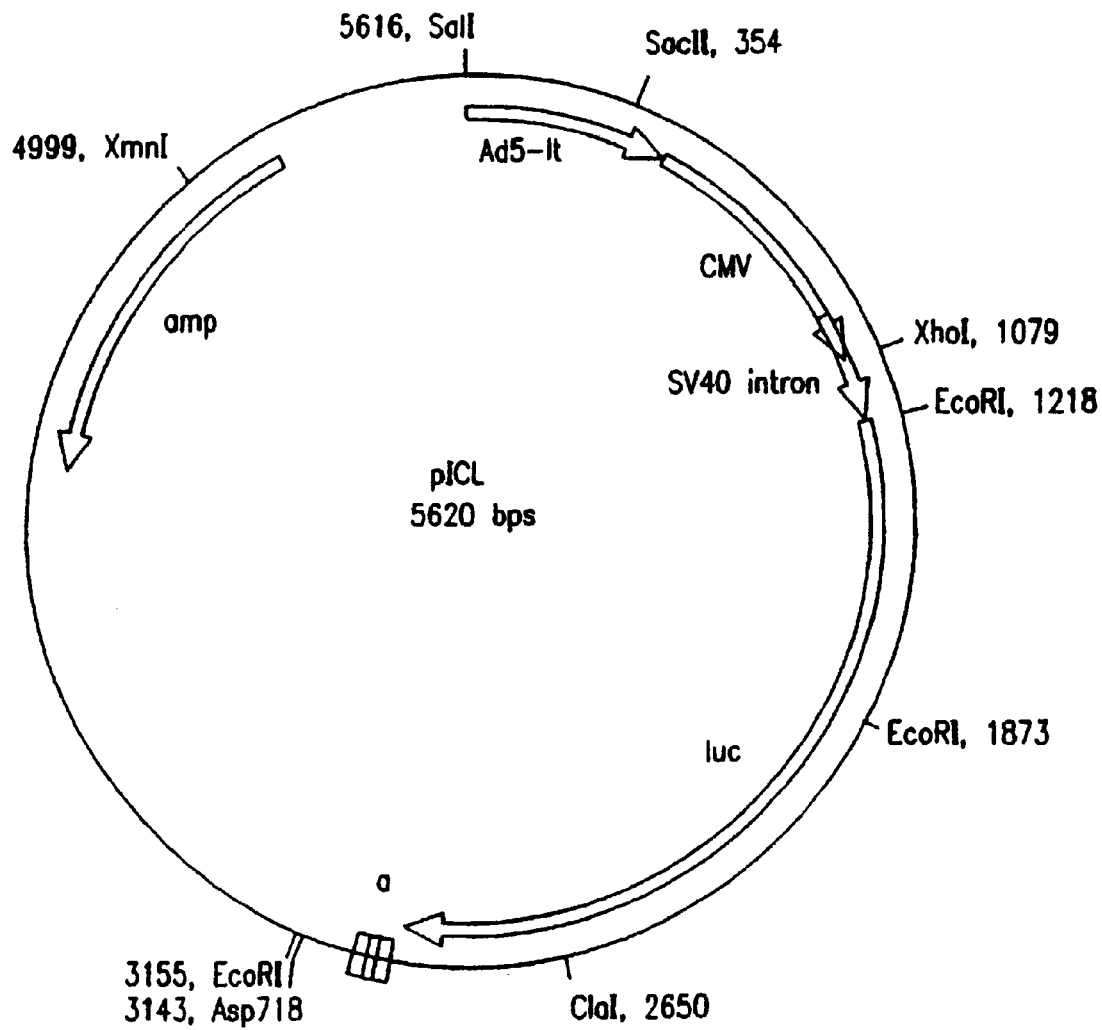
FIG. 19 is a diagram of pICL.

The plasmid has been constructed as follows:

The tet gene of plasmid pMLP10 has been inactivated by deletion of the BamHI-SalI fragment, to generate pMLP10ΔSB. Using primer set PCR/MLP1 (SEQ ID NO: 14) and PCR/MLP3 (SEQ ID NO: 16) a 210 bp fragment containing the Ad5-ITR, flanked by a synthetic SalI restriction site was amplified using pMLP10 DNA as the template. The PCR product was digested with the enzymes EcoRI and SgrAI to generate a 196 bp. fragment. Plasmid pMLP10ΔSB was digested with EcoRI and SgrAI to remove the ITR. This fragment was replaced by the EcoRI-SgrAI-treated PCR fragment to generate pMLP/SAL. Plasmid pCMV-Luc was digested with PvuII to completion and recirculated to remove the SV40-derived poly-adenylation signal and Ad5 sequences with exception of the Ad5 left-terminus. In the resulting plasmid, pCMV-lucΔAd, the Ad5 ITR was replaced by the Sal-site-flanked ITR from plasmid pMLP/SAL by exchanging the XmnI-SacII fragments. The resulting plasmid, pCMV-lucΔAd/SAL, the Ad5 left terminus and the CMV-driven luciferase gene were isolated as an SalI-SmaI fragment and inserted in the SalI and HpaI digested plasmid pBLCATS, to form plasmid pICL. Plasmid pICL is represented in FIG. 19; its sequence is presented in FIGS. 20A–20F (SEQ ID NO: 21).

The plasmid pICL contains the following features:

| | |
|---|---|
| nt. 1–457 | Ad5 left terminus (Sequence 1–457 of human adenovirus type 5) |
| nt. 458–969 early promoter | Human cytomegalovirus enhancer and immediate (see Boshart et al., A Very Strong Enhancer is Located Upstream of an Immediate Early Gene of Human Cytomegalovirus", Cell 41, pp. 521–530 (1985), hereby incorporated herein by reference) (from plasmid pCMVβ, Clontech, Palo Alto, USA) |
| nt. 970–1204 | SV40 19S exon and truncated 16/19S intron (from plasmid pCMVβ) |
| nt. 1218–2987 | Firefly luciferase gene (from pMLP.luc) |
| nt. 3018–3131 | SV40 tandem poly-adenylation signals from late transcript, derived from plasmid pBLCAT5) |
| nt. 3132–5620 | pUC12 backbone (derived from plasmid pBLCAT5) |
| nt. 4337–5191 | β-lactamase gene (Amp-resistance gene, reverse orientation) |

Plasmid pICLhac and pICLhaw

Plasmids pICLhac and pICLhaw were derived from plasmid pICL by digestion of the latter plasmid with the restriction enzyme Asp718. The linearized plasmid was treated with Calf-Intestine Alkaline Phosphatase to remove the 51 phoshate groups. The partially complementary synthetic single-stranded oligonucleotide Hp/asp1 (SEQ ID NO: 17) and Hp/asp2 (SEQ ID NO: 18) were annealed and phosphorylated on their 5' ends using T4-polynucleotide kinase.

Figure 16:
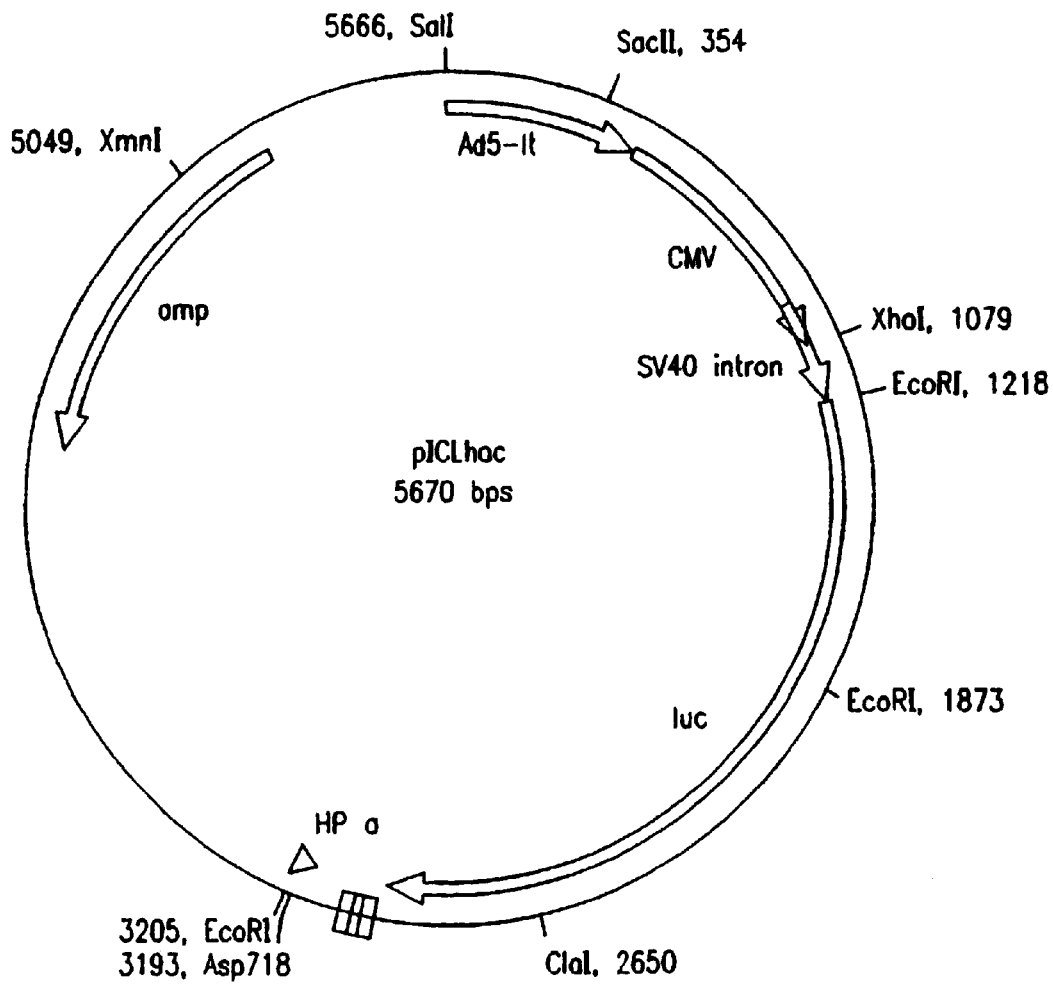
FIG. 16 illustrates a diagram of pICLhac.
Figure 17:
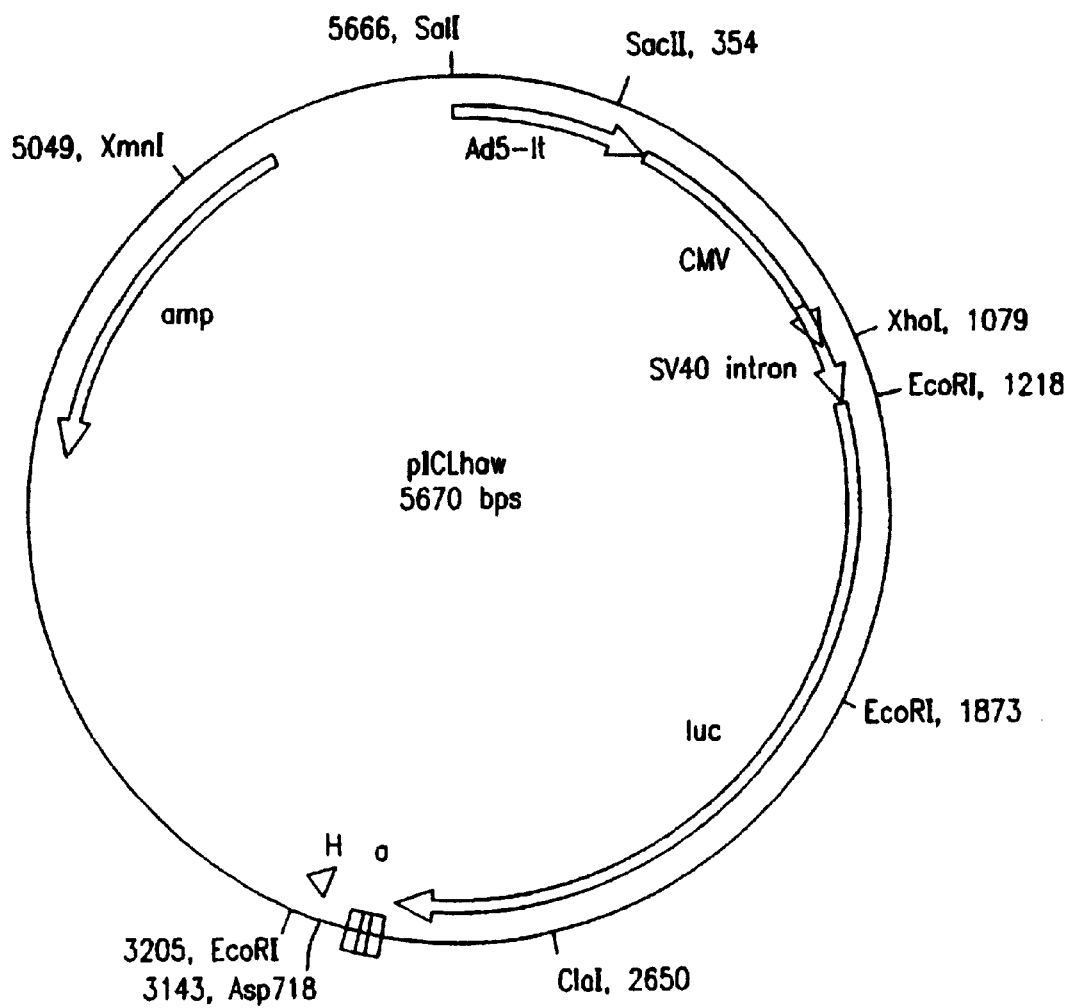
FIG. 17 illustrates a diagram of pICLhaw.

The phosporylated double-stranded oligomers were mixed with the dephosporylated pICL fragment and ligated. Clones containing a single copy of the synthetic oligonucleotide inserted into the plasmid were isolated and characterized using restriction enzyme digests. Insertion of the oligonucleotide into the Asp718 site will at one junction recreate an Asp718 recognition site, whereas at the other junction the recognition site will be disrupted. The orientation and the integrity of the inserted oligonucleotide was verified in selected clones by sequence analyses. A clone containing the oligonucleotide in the correct orientation (the Asp718 site close to the 3205 EcoRI site) was denoted pICLhac. A clone with the oligonucleotide in the reverse orientation (the Asp718 site close to the SV40 derived poly signal) was designated pICLhaw. Plasmids pICLhac and pICLhaw are represented in FIGS. 16 and 17.

Figure 18:
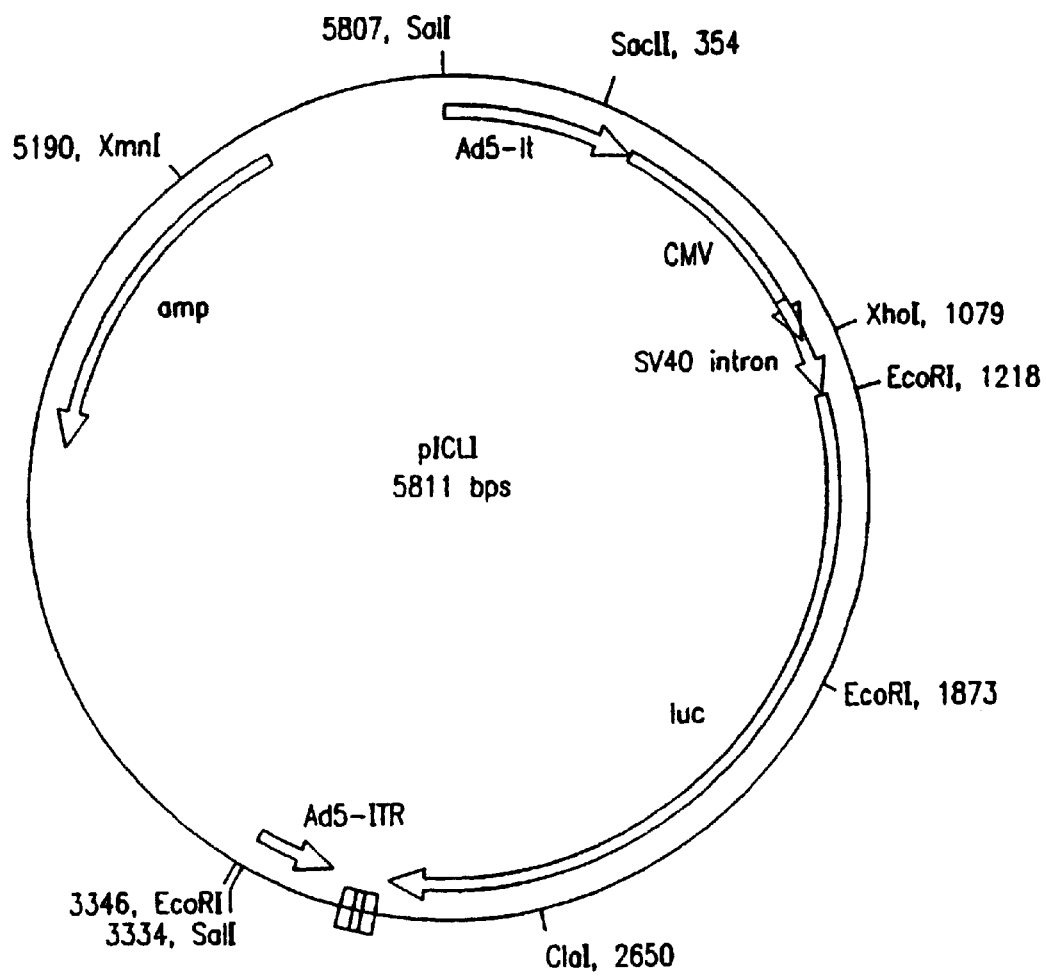
FIG. 18 illustrates a schematic representation of pICLI.

Plasmid pICLI was created from plasmid pICL by insertion of the SalI-SgrAI fragment from pICL, containing the Ad5-ITR into the Asp718 site of pICL. The 194 bp SalI-SgrAI fragment was isolated from pICL, and the cohesive ends were converted to blunt ends using E. coli DNA polymerase I (Klenow fragment) and dNTP's. The Asp718 cohesive ends were converted to blunt ends by treatment with mungbean nuclease. By ligation clones were generated that contain the ITR in the Asp718 site of plasmid pICL. A clone that contained the ITR fragment in the correct orientation was designated pICLI (FIG. 18). Generation of adenovirus Ad-CMV-hcTK. Recombinant adenovirus was constructed according to the method described in EPO Patent application 95202213. Two components are required to generate a recombinant adenovirus. First an adaptor-plasmid containing the left terminus of the adenovirus genome containing the ITR and the packaging signal, an expression cassette with the gene of interest, and a portion of the adenovirus genome which can be used for homologous recombination. In addition, adenovirus DNA is needed for recombination with the aforementioned adaptor plasmid. In the case of Ad-CMV-hcTK, the plasmid PCMV.TK was used as a basis. This plasmid contains nt. 1–455 of the adenovirus type 5 genome, nt. 456–1204 derived from pCMVβ (Clontech, the PstI-StuI fragment that contains the CMV enhancer promoter and the 16S/19S intron from Simian Virus 40), the HSV TK gene (described in EPO Patent application 95202213), the SV40-derived polyadenylation signal (nt 2533–2668 of the SV40 sequence), followed by the BglII-ScaI fragment of Ad5 (nt. 3328–6092 of the Ad5 sequence). These fragments are present in a pMLP10-derived (Levrero et al., 1991) backbone. To generate plasmid pAD-CMVhc-TK, plasmid pCMV.TK was digested with ClaI (the unique ClaI-site is located just upstream of the TK open readingframe) and dephosphorylated with Calf-Intestine Alkaline Phosphate. To generate a hairpin-structure, the synthetic oligonucleotides HP/cla1 (SEQ ID NO: 19) and HP/cla2 (SEQ ID NO: 20) were annealed and phosphorylated on their 5-OH groups with T4-polynucleotide kinase and ATP. The double-stranded oligonucleotide was ligated with the linearized vector fragment and used to transform E. coli strain "Sure". In section of the oligonucleotide into the ClaI site will disrupt the ClaI recognition sites. The oligonucleotide contains a new ClaI site near one of its termini. In selected clones, the orientation and the integrity of the inserted oligonucleotide was verified by sequence analyses. A clone containing the oligonucleotide in the correct orientation (the ClaI site at the ITR side) was denoted pAd-CMV-hcTK. This plasmid was co-transfected with ClaI digested wild-type Adenovirus-type5 DNA into 911 cells. A recombinant adenovirus in which the CMV-hcTK expression cassette replaces the E1 sequences was isolated and propagated using standard procedures.

To study whether the hairpin can be used as a primer for reverse strand synthesis on the displaced strand after replication had started at the ITR, the plasmid pICLhac is introduced into 911 cells (human embryonic retinoblasts transformed with the adenovirus E1 region). The plasmid pICLhaw serves as a control, which contains the oligonucleotide pair HP/asp1 (SEQ ID NO: 17) and 2 (SEQ ID NO: 18) in the reverse orientation but is further completely identical to plasmid pICLhac. Also included in these studies are plasmids pICLI and pICL. In the plasmid pICLI the hairpin is replaced by an adenovirus ITR. Plasmid pICL contains neither a hairpin nor an ITR sequence. These plasmids serve as controls to determine the efficiency of replication by virtue of the terminal-hairpin structure. To provide the viral products other than the E1 proteins (these are produced by the 911 cells) required for DNA replication the cultures are infected with the virus IG.Ad.MLPI.TK after transfection. Several parameters are being studied to demonstrate proper replication of the transfected DNA molecules. First, DNA extracted from the cell cultures transfected with aforementioned plasmids and infected with IG.Ad.MLPI.TK virus is being analyzed by Southern blotting for the presence of the expected replication intermediates, as well as for the presence of the duplicated genomes. Furthermore, virus is isolated from the transfected and IG.Ad.MLPI.TK infected cell populations, that is capable of transferring and expressing a luciferase marker gene into luciferase negative cells.

Plasmid DNA of plasmids pICLhac, pICLhaw, pICLI and pICL have been digested with restriction endonuclease SalI and treated with mungbean nuclease to remove the 4 nucleotide single-stranded extension of the resulting DNA fragment. In this manner, a natural adenovirus 5'ITR terminus on the DNA fragment is created. Subsequently, both the pICLhac and pICLhaw plasmids were digested with restriction endonuclease Asp718 to generate the terminus capable of forming a hairpin structure. The digested plasmids are introduced into 911 cells, using the standard calcium phosphate co-precipitation technique, four dishes for each plasmid. During the transfection, for each plasmid two of the cultures are infected with the IG.Ad.MLPI.TK virus using 5 infectious IG.Ad.MLPI.TK particles per cell. At twenty-hours post-transfection and forty hours post-transfection one Ad.tk-virus-infected and one uninfected culture are used to isolate small molecular-weight DNA using the procedure devised by Hirt. Aliquots of isolated DNA are used for Southern analysis. After digestion of the samples with restriction endonuclease EcoRI using the luciferase gene as a probe a hybridizing fragment of approx. 2.6 kb is detected only in the samples from the adenovirus infected cells transfected with plasmid pICLhac. The size of this fragment is consistent with the anticipated duplication of the luciferase marker gene. This supports the conclusions that the inserted hairpin is capable to serve as a primer for reverse strand synthesis. The hybridizing fragment is absent if the IG.Ad.MLPI.TK virus is omitted, or if the hairpin oligonucleotide has been inserted in the reverse orientation.

The restriction endonuclease DpnI recognizes the tetra-nucleotide sequence 5'-GATC-3', but cleaves only methylated DNA, (that is, only plasmid DNA propagated in, and derived, from E. coli, not DNA that has been replicated in mammalian cells). The restriction endonuclease MboI recognizes the same sequences, but cleaves only unmethylated DNA (viz. DNA propagated in mammalian cells). DNA samples isolated from the transfected cells are incubated with MboI and DpnI and analyzed with Southern blots. These results demonstrate that only in the cells transfected with the pICLhac and the pICLI plasmids large DpnI-resistant fragments are present, that are absent in the MboI treated samples. These data demonstrate that only after transfection of plasmids pICLI and pICLhac replication and duplication of the fragments occur.

These data demonstrate that in adenovirus-infected cells linear DNA fragments that have on one terminus an adenovirus-derived ITR and at the other terminus a nucleotide sequence that can anneal to sequences on the same strand, when present in single-stranded form thereby generate a hairpin structure, and will be converted to structures that have inverted terminal repeat sequences on both ends. The resulting DNA molecules will replicate by the same mechanism as the wild type adenovirus genomes.

Experiment Series 2

The following demonstrates that the DNA molecules that contain a luciferase marker gene, a single copy of the ITR, the encapsidation signal and a synthetic DNA sequence, that is capable of forming a hairpin structure, are sufficient to generate DNA molecules that can be encapsidated into virions.

To demonstrate that the above DNA molecules containing two copies of the CMV-luc marker gene can be encapsidated into virions, virus is harvested from the remaining two cultures via three cycles of freeze-thaw crushing and is used to infect murine fibroblasts. Forty-eight hours after infection, the infected cells are assayed for luciferase activity. To exclude the possibility that the luciferase activity has been induced by transfer of free DNA, rather than via virus particles, virus stocks are treated with DNaseI to remove DNA contaminants. Furthermore, as an additional control, aliquots of the virus stocks are incubated for 60 minutes at 56° C. The heat treatment will not affect the contaminating DNA, but will inactivate the viruses. Significant luciferase activity is only found in the cells after infection with the virus stocks derived from IG.Ad.MLPI.TK-infected cells transfected with the pICLhc and pICLI plasmids. In neither the non-infected cells nor the infected cells transfected with the pICLhw and pICL can significant luciferase activity be demonstrated. Heat inactivation, but not DNaseI treatment, completely eliminates luciferase expression, demonstrating that adenovirus particles, and not free (contaminating) DNA fragments are responsible for transfer of the luciferase reporter gene.

These results demonstrate that these small viral genomes can be encapsidated into adenovirus particles and suggest that the ITR and the encapsidation signal are sufficient for encapsidation of linear DNA fragments into adenovirus particles. These adenovirus particles can be used for efficient gene transfer. When introduced into cells that contain and express at least part of the adenovirus genes (viz. E1, E2, E4, and L, and VA), recombinant DNA molecules that consist of at least one ITR, at least part of the encapsidation signal as well as a synthetic DNA sequence, that is capable of forming a hairpin structure, have the intrinsic capacity to autonomously generate recombinant genomes which can be encapsidated into virions. Such genomes and vector system can be used for gene transfer.

Experiment Series 3

The following demonstrates that DNA molecules which contain nucleotides 3510–35953 (viz. 9.7–100 map units) of the adenovirus type 5 genome (thus lack the E1 protein-coding regions, the right-hand ITR and the encapsidation sequences) and a terminal DNA sequence that is complementary to a portion of the same strand of the DNA molecule when present in single-stranded form other than the ITR, and as a result is capable of forming a hairpin structure, can replicate in 911 cells.

In order to develop a replicating DNA molecule that can provide the adenovirus products required to allow the above mentioned ICLhac vector genome and alike minimal adenovectors to be encapsidated into adenovirus particles by helper cells, the Ad-CMV-hcTK adenoviral vector has been developed. Between the CMV enhancer/promoter region and the thymidine kinase gene the annealed oligonucleotide pair HP/cla1 (SEQ ID NO: 19) and 2 (SEQ ID NO: 20) is inserted. The vector Ad-CMV-hcTK can be propagated and produced in 911 cell using standard procedures. This vector is grown and propagated exclusively as a source of DNA used for transfection. DNA of the adenovirus Ad-CMV-hcTK is isolated from virus particles that had been purified using CsCl density-gradient centrifugation by standard techniques. The virus DNA has been digested with restriction endonuclease ClaI. The digested DNA is size-fractionated on an 0.7% agarose gel and the large fragment is isolated and used for further experiments. Cultures of 911 cells are transfected large ClaI-fragment of the Ad-CMV-hcTK DNA using the standard calcium phosphate co-precipitation technique. Much like in the previous experiments with plasmid pICLhac, the AD-CMV-hc will replicate starting at the right-hand ITR. Once the 1-strand is displaced, a hairpin can be formed at the left-hand terminus of the fragment. This facilitates the DNA polymerase to elongate the chain towards the right-hand-side. The process will proceed until the displaced strand is completely converted to its double-stranded form. Finally, the right-hand ITR will be recreated, and in this location the normal adenovirus replication-initiation and elongation will occur. Note that the polymerase will read through the hairpin, thereby duplicating the molecule. The input DNA molecule of 33250 bp, that had on one side an adenovirus ITR sequence and at the other side a DNA sequence that had the capacity to form a hairpin structure, has now been duplicated, in a way that both ends contain an ITR sequence. The resulting DNA molecule will consist of a palindromic structure of approximately 66500 bp.

This structure can be detected in low-molecular weight DNA extracted from the transfected cells using Southern analysis. The palindromic nature of the DNA fragment can be demonstrated by digestion of the low-molecular weight DNA with suitable restriction endonucleases and Southern blotting with the HSV-TK gene as the probe. This molecule can replicate itself in the transfected cells by virtue of the adenovirus gene products that are present in the cells. In part, the adenovirus genes are expressed from templates that are integrated in the genome of the target cells (viz. the E1 gene products), the other genes reside in the replicating DNA fragment itself. Note however, that this linear DNA fragment cannot be encapsidated into virions. Not only does it lack all the DNA sequences required for encapsidation, but also is its size much too large to be encapsidated.

Experiment Series 4

The following demonstrates that DNA molecules which contain nucleotides 3503–35953 (viz. 9.7–100 map units) of the adenovirus type 5 genome (thus lack the E1 protein-coding regions, the right-hand ITR and the encapsidation sequences) and a terminal DNA sequence that is complementary to a portion the same strand of the DNA molecule other than the ITR, and as a result is capable of forming a hairpin structure, can replicate in 911 cells and can provide the helper functions required to encapsidate the pICLI and pICLhac derived DNA fragments.

The following series of experiments aims to demonstrate that the DNA molecule described in Experiment Series 3 could be used to encapsidate the minimal adenovectors described in Experiment Series 1 and 2.

In the experiments the large fragment isolated after endonuclease ClaI-digestion of Ad-CMV-hcTK DNA is introduced into 911 cells (conform the experiments described in part 1.3) together with endonuclease SalI, mungbean nuclease, endonuclease Asp718-treated plasmid pICLhac, or as a control similarly treated plasmid pICLhaw. After 48 hours virus is isolated by freeze-thaw crushing of the transfected cell population. The virus-preparation is treated with DNaseI to remove contaminating free DNA. The virus is used subsequently to infect Rat2 fibroblasts. Forty-eight hours post infection, the cells are assayed for luciferase activity. Significant luciferase activity can be demonstrated only in the cells infected with virus isolated from the cells transfected with the pICLhac plasmid, and not with the pICLhaw plasmid. Heat inactivation of the virus prior to infection completely abolishes the luciferase activity, indicating that the luciferase gene is transferred by a viral particle. Infection of 911 cell with the virus stock did not result in any cytopathological effects, demonstrating that the pICLhac is produced without any infectious helper virus that can be propagated on 911 cells. These results demonstrate that the proposed method can be used to produce stocks of minimal-adenoviral vectors, that are completely devoid of infectious helper viruses that are able to replicate autonomously on adenovirus-transformed human cells or on non-adenovirus transformed human cells.

Besides the system described in this application, another approach for the generation of minimal adenovirus vectors has been disclosed in PCT International Application WO 94/12649. The method described in WO 94/12649 exploits the function of the protein IX for the packaging of minimal adenovirus vectors (Pseudo Adenoviral Vectors ("PAV") in the terminology of WO 94/12649). PAVs are produced by cloning an expression plasmid with the gene of interest between the left-hand (including the sequences required for encapsidation) and the right-hand adenoviral ITRs. The PAV is propagated in the presence of a helper virus. Encapsidation of the PAV is preferred compared the helper virus because the helper virus is partially defective for packaging. (Either by virtue of mutations in the packaging signal or by virtue of its size (virus genomes greater than 37.5 kb package inefficiently). In addition, the authors propose that in the absence of the protein IX gene the PAV will be preferentially packaged. However, neither of these mechanisms appear to be sufficiently restrictive to allow packaging of only PAVs/minimal vectors. The mutations proposed in the packaging signal diminish packaging, but do not provide an absolute block as the same packaging-activity is required to propagate the helper virus. Also neither an increase in the size of the helper virus nor the mutation of the protein IX gene will ensure that PAV is packaged exclusively. Thus, the method described in WO 94/12649 is unlikely to be useful for the production of helper-free stocks of minimal adenovirus vectors/PAVs.

Although the application has been described with reference to certain preferred embodiments and illustrative examples, the scope of the invention is to be determined by reference to the appended claims.

References

Berk, A. J. (1986): *Ann. Rev. genet.* 20, 45–79.

Bernards, R., Schrier, P. I., Bos, J. L., and Eb, A. J. v. d. (1983): Role of adenovirus types 5 and 12 early region 1b tumor antigens in oncogenic transformation. Virology 127, 45–53.

Bett, A. J, Prevec, L., and Graham, F. L. (1993): Packaging Capacity and Stability of Human Adenovirus Type-5 Vectors. *J Virol* 67, 5911–5921.

Blaese, M., Blankenstein, T., Brenner, M., Cohen-Hageenauer, O., Gansbacher, B., Russell, S., Sorrentino, B., and Velu, T. (1995). Vectors in cancer therapy: how will they deliver? *Cancer Gene Ther.* 2, 291–297.

Boshart, M., Weber, F., Jahn, G., Dorsch-Häler, K., Fleckenstein, B., and Scaffner, W. (1985): A very strong enhancer is located upstream of an immediate early gene of human Cytomegalovirus. Cell 41, 521–530.

Bout, A., Imler, J. L., Schulz, H., Perricaudet, M., Zurcher, C., Herbrink, P., Valerio, D., and Pavirani, A. (1994a): In vivo adenovirus-mediated transfer of human CFTR cDNA to Rhesus monkey airway epithelium: efficacy, toxicity and safety. *Gene Therapy* 1, 385–394.

Bout, A., Perricaudet, M., Baskin, G., Imler, J. L., Scholte. B. J., Pavirani, A., and Valerio, D. (1994b): Lung gene therapy: in vivo adenovirus mediated gene transfer to rhesus monkey airway epithelium. *Human Gene Therapy* 5, 3–10.

Brody, S. L., and Crystal, R. G. (1994): Adenovirus-mediated in vivo gene transfer. *Ann N Y Acad Scl* 716, 90–101.

Brough, D. E., Cleghon, V., and Klessig, D. F. (1992). Construction, characterization, and utilization of cell lines which inducibly express the adenovirus DNA-binding protein. *Virology* 190(2), 624–34.

Brough, D. E., Rice, S. A., Sell, S., and Klessig, D. F. (1985): Restricted changes in the adenovirus DNA-binding protein that lead to extended host range or temperature-sensitive phenotypes. *J. Virol.* 55, 206–212.

Daniell, E. (1976): Genome structure of incomplete particles of adenovirus. *J. Virol.* 19, 685–708.

Elsen, P. J. V. d., Houweling, A., and Eb, A. J. V. d. (1983). Expression of region E1B of human adenoviruses in the absence of region E1A is not sufficient for complete transformation. *Virology* 128, 377–390.

Engelhardt, J. F., Litzky, L., and Wilson. J. M. (1994a): Prolonged transgene expression in cotton rat lung with recombinant adenoviruses defective in E2A. *Hum. Gene Ther.* 5. 1217–1229.

Engelhardt, J. F., Simon, R. H., Yang, Y., Zepeda, M., Weber-Pendleton, S., Doranz, B., Grossman, M., and Wilson, J. M. (1993): Adenovirus-mediated transfer of the CFTR gene to lung or nonhuman primates: biological efficacy study. *Human Gene Therapy* 4, 759–769.

Engelhardt, J. F., Ye, X., Doranz, B., and Wilson, J. M. (1994b): Ablation of E2A in recombinant adenoviruses improves transgene persistence and decreases inflammatory response in mouse liver. *Proc Natl Acad Scl USA* 91, 6196–200.

Fang, B., Wang, H., Gordon, G., Bellinger, D. A., Read, M. S., Brinkhous, K. M., Woo, S. L. C., and Eisensmith, R. C. (1996). Lack of persistence of E1-recombinant adenoviral vectors containing a temperature sensitive E2A mutation in immunocompetent mice and hemophilia dogs. *Gene Ther.* 3, 217–222.

Fallaux, F. J., Kranenburg, O., Cramer. S. J., Houweling, A., Ormondt, H. v., Hoeben. R. C., and Eb, A. J. v.d. (1996). Characterization of 911: a new helper cell line for the titration and propagation of early-region- 1-deleted adenoviral vectors. *Hum. Gene Ther.* 7, 215–222.

Gooding, L. R., Aquino, L., Duerksen-Hughes, P. J., Day, D., Horton, T. M., Yei, S., and Wold, W. S. M. (1991): The E1B 19,000-molecular-weight protein of group C adenoviruses prevents tumor necrosis factor cytolysis of human cells but not of mouse cells. *J Virol.* 65, 3083–3094.

Gräble, M., and Hearing, P. (1990): Adenovirus type 5 packaging domain is composed of a repeated element that is functionally redundant. *J. Virol.* 64, 2047–2056.

Gräble, M., and Hearing, P. (1992): cis and trans Requirements for the Selective Packaging of Adenovirus Type-5 DNA. *J. Virol* 66, 723–731.

Graham, F. L., and van der Eb, A. J. (1973). A new technique for the assay of infectivity of human adenovirus 5 DNA. *Virology* 52, 456–467.

Graham, F. L., Smiley, J., Russell, W. C., and Naira, R. (1977): Characteristics of a human cell line transformed by DNA from adenovirus type 5. *J. Gen. Virol.* 36, 59–72.

Haddada, H., Ragot, T., Cordier, L., Duffour, M. T., and Perricaudet, M. (1993): Adenoviral interleukin-2 gene transfer into P815 tumor cells abrogates tumorigenicity and induces antitumoral immunity in mice. *Hum Gene Ther* 4, 703–11.

Hay, R. T., Stow, N. D., and McDougall, I. M. (1984): Replication of adenovirus minichromosomes. *J. Mol. Biol.* 174, 493–510.

Hearing, P., Samulski, R. J., Wishart, W. L., and Shenk, T. (1987): Identification of a repeated sequence element required for efficient encapsidation of the adenovirus type 5 chromosome. *J. Virol.* 61, 2555–2558.

Horwitz, M. S. (1990): Adenoviridae and their replication, pp. 1679–1740. In B. N. Fields, and D. M. Knipe (Eds): *Virology*, Raven Press, Ltd, New York.

Hu, C. H., Xu, F. Y., Wang, K.; Pearson, A. N., and Pearson, G. D. (1992): Symmetrical Adenovirus Minichromosomes Have Hairpin Replication Intermediates. Gene 110, 145–150.

Imler, J. L., Chartier, C., Dreyer, D., Dieterle, A., Sainte-Marie, M., Faure, T., Pavirani, A., and Mehtali, M. (1996). Novel complementation cell lines derived from human lung tarcinoma A549 cells support the growth of E1-deleted adenovirus vectors. *Gene Ther.* 3, 75–84.

Jochemsen. A. G., Peltenburg, L. T. C., Pas, M. F. W. T., Wit, C. M. d., Bos, J. L., and Eb. A. J. v.d. (1987): *EMBO J.* 6, 3399–3405.

Klessig, D. F., and Grodzicker, T. (1979): Mutations that allow human Ad2 and Ad5 to express late genes in monkey cells maps in the viral gene encoding the 72K DNA-binding protein. Cell 17, 957–566.

Klessig, D. F. Grodzicker, T., and Cleghon, V. (1984): Construction of human cell lines which contain and express the adenovirus DNA binding protein gene by cotransformation with the HSV-1 tk gene. *Virus Res.* 1, 169–188.

Kruijer, W., Nicolas, J. C., Schaik. F. M. v., and Sussenbach, J. S. (1983): Structure and function of DNA binding proteins from revertants of adenovirus type 5 mutants with a temperature-sensitive DNA replication. *Virology* 124, 425–433.

Lechner, R. L., and Kelly Jr., T. J. (1977): The structure of replicating adenovirus 2 DNA molecules. *J. Mol. Biol.* 174, 493–510.

Leij, L. de, Postmus, P. E., Buys, C. H. C. M., Elema, J. D., Ramaekers, F., Poppema, S., Brouwer, M., Veen, A. Y. v.d., Mesander, G., and The, T. H. (1985): Characterization of three new variant type cell lines derived from small cell carcinoma of the lung. *Cancer Res.* 45, 6024–6033.

Levrero, M., Barban, V., Manteca, S., Ballay, A., Balsamo, C., Avantaggiati, M. L., Natoli, G., Skellekens, H., Tiollais, P., and Perricaudet, M. (1991): Defective and nondefective adenovirus vectors for expressing foreign genes in vitro and in vivo. Gene 101, 195–202.

Lochmüller, H., Jani, A., Huard, J., Prescott, S., Simoneau, M., Massie, B., Karpati, G., and Acasdi, G. (1994): Emergence of early region 1-containing replication-competent adenovirus in stocks of replication-defective adenovirus recombinants (ΔE1–ΔE3) during multiple passages in 293 cells. *Hum. Gene Ther.* 5, 1485–1492.

Matsui, T., Murayama, M., and Mita, T. (1986): Adenovirus 2 peptide IX is expressed only on replicated DNA molecules. *Mol. Cell Biol.* 6, 4149–4154.

Michelson, A. M., Markham, A. F., and Orkin, S. H. (1983): Isolation and DNA sequence of a full-length cDNA clone for human X-chromosome encoded phosphoglycerate kinase. *Proc. Natl. Acad. Sci. USA* 80, 472–476.

Morin, J. E., Lubeck, M. D., Barton. J. E., Conley, A. J., Davis, A. R., and Hung, P. P. (1987): Recombinant adenovirus induces antibody response to hepatitis B virus surface antigens. *Proc. Natl. Acad Sci. USA*, 84, 4626–4630.

Nicolas, J. C., Suarez, F., Levine, A. J., and Girard, M. (1981): Temperature-independent revertants of adenovirus H5ts125 and H5ts107 mutants in the DNA binding protein: isolation of a new class of host range temperature conditional revertants. *Virology* 108, 521–524.

Ostrove, J. M. (1994): Safety testing programs for gene therapy viral vectors. *Cancer Gene Ther.* 1, 125–131.

Pacini, D. L., Dubovi, E. J., and Clyde, W. A. (1984): *J. Infect. Dis.* 150, 92–97.

Postmus, P. E., Ley, L. d., Veen, A. Y. v.d., Mesander, G., Buys, C. H. C. M., and Elema, J. D. (1988): Two small cell lung cancer cell lines established from rigid bronchoscope biopsies. *Eur. J. Clin. Oncol.* 24, 753–763.

Rice, S. A., and Klessig, D. F. (1985): Isolation and analysis of adenovirus type 5 mutants containing deletions in the gene encoding the DNA-binding protein. *J. Virol.* 56, 767–778.

Roberts, B. E., Miller, J. S., Kimelman, D., Cepko, C. L., Lemischka, I. R., and Mulligan, R. C. (1985): *J. Virol.* 56, 404–413.

Shapiro, D. L., Nardone, L. L., Rooney, S. A., Motoyama, E. K., and Munoz, J. L. (1978). Phospholipid biosynthesis and secretion by a cell line (A549) which resembles type II alveolar epithelial cells. *Biochim. Biophys. Acta* 530, 197–207.

Simon, R. H., Engelhardt, J. F., Yang, Y., Zepeda., M., Weber-Pendleton, S., Grossman, M., and Wilson, J. M. (1993): Adenovirus-mediated transfer of the CFTR gene to lung of nonhuman primates: toxicity study. *Human Gene Therapy* 4, 771–780.

Singer-Sam, J., Keith, D. H., Tani, K., Simmer, R. L., Shively, L., Lindsay, S., Yoshida, A., and Riggs, A. D. (1984): Sequence of the promoter region of the gene for X-linked 3-phosphoglycerate kinase. Gene 32, 409–417.

Stein, R. W., and Whelan, J. (1989): Insulin gene enhancer activity is inhibited by adenovirus 5 E1A gene products. *Mol Cell Biol* 9, 4531–4.

Stratford-Perricaudet, L. D., and Perricaudet, M. (1991): Gene transfer into animals: the promise of adenovirus, pp. 51–61. In O. Cohen-Adenauer, and M. Boiron (Eds): *Human Gene Transfer*, John Libbey Eurotext.

Telling, G. C., Perera, S., Szatkowski, O. M., and Williams, J. (1994): Absence of an essential regulatory influence of the adenovirus E1B 19-kilodalton protein on viral growth and early gene expression in human diploid WI38, HeLa, and A549 cells. *J. Virol* 68, 541–7.

Tooze, J. (1981): *DNA Tumor Viruses* (revised). Cold Spring Harbor Laboratory. Cold Spring Harbor, N.Y.

Vieira, J., and Messing, J. (1987): Production of single stranded plasmid DNA, pp. 3–11: *Methods in Enzymology*, Acad. Press Inc.

Vincent, A. J. P. E., Esandi, M. d. C., Someren, G. D. v., Noteboom, J. L., C. J. J, A., Vecht, C., Smitt, P. A. E. S., Bekkum, D. W. v., Valerio, D., Hoogerbrugge, P. M., and Bout, A. (1996a). Treatment of Lepto-meningeal metastasis in a rat model using a recombinant adenovirus containing the HSV-tk gene. *J. Neurosurg.* in press.

Vincent, A. J. P. E., Vogels, R., Someren, G. v, Esandi, M. d. C., Noteboom, J. L., Avezaat, C. J. J., Vecht, C., Bekkum, D. W. v., Valerio, D., Bout, A., and Hoogerbrugge, P. M. (1996b). Herpes Simplex Virus Thymidine Kinase gene therapy for rat malignant brain tumors. *Hum. Gene Ther.* 7, 197–205.

Wang, K., and Pearson, G. D. (1985): Adenovirus sequences required for replication in vivo. *Nucl. Acids Res.* 13, 5173–5187.

White, E., Denton, A., and Stillman, B. (1988): *J. Virol.* 62, 3445–3454.

Yang, Y., Li, Q., Ertl, H. C. J., and Wilson, J. M. (1995): Cellular and humoral immune responses viral antigens create barriers to lung-directed gene therapy with recombinant adenoviruses. *J. Virol.* 69, 2004–2015.

Yang, Y., Nunes, F. A., Berencsi, K., Furth, E. E., Gonczol, E., and Wilson, J. M. (1994a): Cellular immunity to viral antigens limits E1-deleted adenoviruses for gene therapy. *Proc Natl Acad Sci USA* 91, 4407–11.

Yang, Y., Nunes, F. A., Berencsi, K., Gonczol, E., Engelhardt, J. F., and Wilson, J. M. (1994b): Inactivation of E2A in recombinant adenoviruses improves the prospect for gene therapy in cystic fibrosis. *Nat Genet* 7, 362–9.

Zantema, A., Fransen, J. A. M., Davis-Olivier, A., Ramaekers, F. C. S., Vooijs, G. P., Deleys, B., and Eb, A. J. v.d. (1985). Localization of the E1B proteins of adenovirus 5 in transformed cells, as revealed by interaction with monoclonal antibodies. *Virology* 142, 44–58.

What is claimed is:

1. A method for intracellular amplification of DNA comprising:

providing a mammalian cell with a first nucleic acid sequence encoding functional adenoviral E2A and E2B gene products, further providing said mammalian cell with a second nucleic acid sequence encoding a linear DNA fragment to be amplified, said second nucleic acid sequence having two functional adenoviral Inverted Terminal Repeats on the termini thereof, allowing said linear DNA fragment to be acted upon by said adenoviral E2A and E2B gene products, thus intracellularly amplifying said linear DNA fragment, and extracting the thus amplified linear DNA fragment.

2. The method of claim 1, wherein at least one of said functional Inverted Terminal Repeats is a nucleotide sequence comprising a part or a derivative of an adenovirus Inverted Terminal Repeat which functions as an Inverted Terminal Repeat.

3. A method for intracellular amplification of DNA comprising:

providing mammalian cells with a first nucleic acid sequence encoding functional adenoviral E2A and E2B gene products, further providing said mammalian cells with a second nucleic acid sequence encoding a linear DNA fragment to be amplified, said second nucleic acid sequence having two functional adenoviral Inverted Terminal Repeats on the termini thereof, allowing said linear DNA fragment to be acted upon by said adenoviral E2A and E2B gene products, thus intracellularly amplifying said linear DNA fragment, and enriching for amplified DNA by selecting the mammalian cells with a desired phenotype.

4. A method for intracellular amplification of DNA comprising:

providing a mammalian cell with a first nucleic acid sequence encoding functional adenoviral E2A and E2B gene products, further providing said mammalian cell with a second nucleic acid sequence encoding a linear DNA fragment to be amplified, said second nucleic acid sequence having a functional adenoviral Inverted Terminal Repeat and a hairpin-like structure on opposite termini thereof, allowing said linear DNA fragment to be acted upon by said adenoviral E2A and E2B gene products, thus intracellularly amplifying said linear DNA fragment, and extracting the thus amplified linear DNA fragment.

* * * * *

UNITED STATES PATENT AND TRADEMARK OFFICE
CERTIFICATE OF CORRECTION

PATENT NO. : 6,238,893 B1
DATED : May 29, 2001
INVENTOR(S) : Robert Cornelius Hoeben and Abraham Bout It is certified that error appears in the above-identified patent and that said Letters Patent is hereby corrected as shown below:

Title page,
Item [56], References Cited, in "Imier et al.," change "Imier" to -- Imler --; in "Bernards, et al.", change "*Trahsformation*" to -- *Transformation* --; in "Lochmuller, H., et al." change "=" to -- + --

Column 20,
Line 9, change "PER-C3" to -- PER.C3 --

Signed and Sealed this

First Day of July, 2003

JAMES E. ROGAN
*Director of the United States Patent and Trademark Office*

SEQUENCE LISTING

```
<160> NUMBER OF SEQ ID NOS:  22

<210> SEQ ID NO 1
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer Ea-1

<400> SEQUENCE: 1
cgtgtagtgt atttataccc g                                              21

<210> SEQ ID NO 2
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: Description of Artifical Sequence: Primer Ea-2

<400> SEQUENCE: 2
tcgtcactgg gtggaaagcc a                                              21

<210> SEQ ID NO 3
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer Ea-3

<400> SEQUENCE: 3
tacccgccgt cctaaaatgg c                                              21

<210> SEQ ID NO 4
<211> LENGTH: 20
<212> TYPE: DNA
<213> ORGANISM: Artificial Sequence
<220> FEATURE:
<221> NAME/KEY:
<222> LOCATION:
<223> OTHER INFORMATION: Description of Artificial Sequence:  Primer
      Ea-5

<400> SEQUENCE: 4
tggacttgag ctgtaaacgc                                                20

<210> SEQ ID NO 5
<211> LENGTH: 21
<212> TYPE: DNA
```

```
<213> ORGANISM: Artificial Sequence
<220> FEATURE:
<221> NAME/KEY:
<222> LOCATION:
<223> OTHER INFORMATION: Description of Artificial Sequence: Primer Ep-2

<400> SEQUENCE: 5
gcctccatgg aggtcagatg t                                              21

<210> SEQ ID NO 6
<211> LENGTH: 20
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer Eb-1

<400> SEQUENCE: 6
gcttgagccc gagacatgtc                                                20

<210> SEQ ID NO 7
<211> LENGTH: 24
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer Eb-2

<400> SEQUENCE: 7
cccctcgagc tcaatctgta tctt                                           24

<210> SEQ ID NO 8
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Description of Artificial Sequence:  Primer
      SV40-1

<400> SEQUENCE: 8
gggggatccg aacttgttta ttgcagc                                        27

<210> SEQ ID NO 9
<211> LENGTH: 25
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer
      SV40-2

<400> SEQUENCE: 9
gggagatcta gacatgataa gatac                                          25

<210> SEQ ID NO 10
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer
      Ad5-1
```

```
<400> SEQUENCE: 10
gggagatctg tactgaaatg tgtgggc                                      27

<210> SEQ ID NO 11
<211> LENGTH: 24
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer
      Ad5-2

<400> SEQUENCE: 11
ggaggctgca gtctccaacg gcgt                                         24

<210> SEQ ID NO 12
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer ITR1

<400> SEQUENCE: 12
gggggatcct caaatcgtca cttccgt                                      27

<210> SEQ ID NO 13
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer ITR2

<400> SEQUENCE: 13
ggggtctaga catcatcaat aatatac                                      27

<210> SEQ ID NO 14
<211> LENGTH: 32
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: PCR primer
      PCR/MLP1

<400> SEQUENCE: 14
ggcgaattcg tcgacatcat caataatata cc                                32

<210> SEQ ID NO 15
<211> LENGTH: 32
<212> TYPE: DNA
<213> ORGANISM: Artificial Sequence
<220> FEATURE:
<221> NAME/KEY:
<222> LOCATION:
<223> OTHER INFORMATION: Description of Artificial Sequence:  PCT primer
      PCR/MLP2

<400> SEQUENCE: 15
ggcgaattcg gtaccatcat caataatata cc                                32

<210> SEQ ID NO 16
```

```
<211> LENGTH: 17
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: PCT primer
      PCR/MLP3

<400> SEQUENCE: 16
ctgtgtacac cggcgca                                                       17

<210> SEQ ID NO 17
<211> LENGTH: 50
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: PCT primer
      HP/asp1

<400> SEQUENCE: 17
gtacactgac ctagtgccgc ccgggcaaag cccgggcggc actaggtcag                   50

<210> SEQ ID NO 18
<211> LENGTH: 50
<212> TYPE: DNA
<213> ORGANISM: Artificial Sequence
<220> FEATURE:
<221> NAME/KEY:
<222> LOCATION:
<223> OTHER INFORMATION: Description of Artificial Sequence:  PCT primer
      HP/asp2

<400> SEQUENCE: 18
gtacctgacc tagtgccgcc cgggctttgc ccgggcggca ctaggtcagt                   50

<210> SEQ ID NO 19
<211> LENGTH: 55
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: PCT primer
      HP/cla1

<400> SEQUENCE: 19
gtacattgac ctagtgccgc ccgggcaaag cccgggcggc actaggtcaa tcgat             55

<210> SEQ ID NO 20
<211> LENGTH: 55
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: primer
      HP/cla2

<400> SEQUENCE: 20
gtacatcgat tgacctagtg ccgcccgggc tttgcccggg cggcactagg tcaat             55

<210> SEQ ID NO 21
<211> LENGTH: 5620
<212> TYPE: DNA
<213> ORGANISM: Artificial Sequence
<220> FEATURE:
```

<221> NAME/KEY: Ad5 left terminus
<222> LOCATION: 1..457
<221> NAME/KEY: enhancer
<222> LOCATION: 458..969
<221> NAME/KEY: exon
<222> LOCATION: 970..1204
<221> NAME/KEY: gene
<222> LOCATION: 1218..2987
<221> NAME/KEY: polyA_signal
<222> LOCATION: 3018..3131
<221> NAME/KEY: pUC12 backbone
<222> LOCATION: 3132..5620
<221> NAME/KEY: gene
<222> LOCATION: 4337..5191
<223> OTHER INFORMATION: Description of Artificial Sequence: Plasmid pICL

<400> SEQUENCE: 21

```
catcatcaat aatataccttt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tatttgtcta gggccgcggg     360
gactttgacc gtttacgtgg agactcgccc aggtgttttt ctcaggtgtt tccgcgttc      420
cgggtcaaag ttggcgtttt attattatag tcaggggctg caggtcgtta cataacttac     480
ggtaaatggc ccgcctggct gaccgcccaa cgacccccgc ccattgacgt caataatgac     540
gtatgttccc atagtaacgc caatagggac tttccattga cgtcaatggg tggagtattt     600
acggtaaact gcccacttgg cagtacatca agtgtatcat atgccaagta cgccccctat     660
tgacgtcaat gacggtaaat ggcccgcctg gcattatgcc cagtacatga ccttatggga     720
cttcctact tggcagtaca tctacgtatt agtcatcgct attaccatgg tgatgcggtt      780
ttggcagtac atcaatgggc gtggatagcg gtttgactca cggggatttc caagtctcca     840
ccccattgac gtcaatggga gtttgttttg gcaccaaaat caacgggact ttccaaaatg     900
tcgtaacaac tccgccccat tgacgcaaat gggcggtagg cgtgtacggt gggaggtcta     960
tataagcaga gctcgtttag tgaaccgtca gatcgcctgg agacgccatc cacgctgttt    1020
tgacctccat agaagacacc gggaccgatc cagcctccgg actctagagg atccggtact    1080
cgaggaactg aaaaaccaga aagttaactg gtaagtttag tcttttgtc ttttatttca    1140
ggtcccggat ccggtggtgg tgcaaatcaa agaactgctc ctcagtggat gttgcctta    1200
cttctagtat caagcttgaa ttcctttgtg ttacattctt gaatgtcgct cgcagtgaca    1260
ttagcattcc ggtactgttg gtaaaatgga agacgccaaa aacataaaga aaggcccggc    1320
gccattctat cctctagagg atggaaccgc tggagagcaa ctgcataagg ctatgaagaa    1380
atacgccctg gttcctggaa caattgcttt tacagatgca catatcgagg tgaacatcac    1440
gtacgcggaa tacttcgaaa tgtccgttcg gttggcagaa gctatgaaac gatatgggct    1500
gaatacaaat cacagaatcg tcgtatgcag tgaaaactct cttcaattct ttatgccggt    1560
gttgggcgcg ttatttatcg gagttgcagt tgcgcccgcg aacgacattt ataatgaacg    1620
tgaattgctc aacagtatga acatttcgca gcctaccgta gtgtttgttt ccaaaaaggg    1680
gttgcaaaaa attttgaacg tgcaaaaaaa attaccaata atccagaaaa ttattatcat    1740
ggattctaaa acggattacc agggatttca gtcgatgtac acgttcgtca catctcatct    1800
```

-continued

| | | | | |
|---|---|---|---|---|
| acctcccggt | tttaatgaat | acgattttgt | accagagtcc | tttgatcgtg acaaacaat | 1860 |
| tgcactgata | atgaattcct | ctggatctac | tgggttacct | aagggtgtgg cccttccgca | 1920 |
| tagaactgcc | tgcgtcagat | tctcgcatgc | cagagatcct | attttggca atcaaatcat | 1980 |
| tccggatact | gcgattttaa | gtgttgttcc | attccatcac | ggttttggaa tgtttactac | 2040 |
| actcggatat | tgatatgtg | gatttcgagt | cgtcttaatg | tatagatttg aagaagagct | 2100 |
| gttttttacga | tcccttcagg | attacaaaat | tcaaagtgcg | ttgctagtac caaccctatt | 2160 |
| ttcattcttc | gccaaaagca | ctctgattga | caaatacgat | ttatctaatt tacacgaaat | 2220 |
| tgcttctggg | ggcgcacctc | tttcgaaaga | agtcgggaa | gcggttgcaa acgcttcca | 2280 |
| tcttccaggg | atacgacaag | gatatgggct | cactgagact | acatcagcta ttctgattac | 2340 |
| acccgagggg | gatgataaac | cgggcgcggt | cggtaaagtt | gttccatttt ttgaagcgaa | 2400 |
| ggttgtggat | ctggataccg | ggaaaacgct | gggcgttaat | cagagaggcg aattatgtgt | 2460 |
| cagaggacct | atgattatgt | ccggttatgt | aaacaatccg | gaagcgacca acgccttgat | 2520 |
| tgacaaggat | ggatggctac | attctggaga | catagcttac | tgggacgaag acgaacactt | 2580 |
| cttcatagtt | gaccgcttga | agtctttaat | taaatacaaa | ggatatcagg tggcccccgc | 2640 |
| tgaattggaa | tcgatattgt | tacaacaccc | caacatcttc | gacgcgggcg tggcaggtct | 2700 |
| tcccgacgat | gacgccggtg | aacttcccgc | cgccgttgtt | gttttggagc acggaaagac | 2760 |
| gatgacggaa | aaagagatcg | tggattacgt | cgccagtcaa | gtaacaaccg cgaaaaagtt | 2820 |
| gcgcggagga | gttgtgtttg | tggacgaagt | accgaaaggt | cttaccggaa aactcgacgc | 2880 |
| aagaaaaatc | agagagatcc | tcataaaggc | caagaagggc | ggaaagtcca aattgtaaaa | 2940 |
| tgtaactgta | ttcagcgatg | acgaaattct | tagctattgt | aatgggggat ccccaacttg | 3000 |
| tttattgcag | cttataatgg | ttacaaataa | agcaatagca | tcacaaattt cacaaataaa | 3060 |
| gcattttttt | cactgcattc | tagttgtggt | ttgtccaaac | tcatcaatgt atcttatcat | 3120 |
| gtctggatcg | gatcgatccc | cgggtaccga | gctcgaattc | gtaatcatgg tcatagctgt | 3180 |
| ttcctgtgtg | aaattgttat | ccgctcacaa | ttccacacaa | catacgagcc ggaagcataa | 3240 |
| agtgtaaagc | ctggggtgcc | taatgagtga | gctaactcac | attaattgcg ttgcgctcac | 3300 |
| tgcccgcttt | ccagtcggga | aacctgtcgt | gccagctgca | ttaatgaatc ggccaacgcg | 3360 |
| cggggagagg | cggtttgcgt | attgggcgct | cttccgcttc | ctcgctcact gactcgctgc | 3420 |
| gctcggtcgt | tcggctgcgg | cgagcggtat | cagctcactc | aaaggcggta atacggttat | 3480 |
| ccacagaatc | aggggataac | gcaggaaaga | acatgtgagc | aaaaggccag caaaaggcca | 3540 |
| ggaaccgtaa | aaaggccgcg | ttgctggcgt | ttttccatag | gctccgcccc cctgacgagc | 3600 |
| atcacaaaaa | tcgacgctca | agtcagaggt | ggcgaaaccc | gacaggacta taaagatacc | 3660 |
| aggcgtttcc | ccctggaagc | tccctcgtgc | gctctcctgt | tccgaccctg ccgcttaccg | 3720 |
| gatacctgtc | cgcctttctc | ccttcgggaa | gcgtggcgct | ttctcatagc tcacgctgta | 3780 |
| ggtatctcag | ttcggtgtag | gtcgttcgct | ccaagctggg | ctgtgtgcac gaaccccccg | 3840 |
| ttcagcccga | ccgctgcgcc | ttatccggta | actatcgtct | tgagtccaac ccggtaagac | 3900 |
| acgacttatc | gccactggca | gcagccactg | gtaacaggat | tagcagagcg aggtatgtag | 3960 |
| gcggtgctac | agagttcttg | aagtggtggc | ctaactacgg | ctacactaga aggacagtat | 4020 |
| ttggtatctg | cgctctgctg | aagccagtta | ccttcggaaa | aagagttggt agctcttgat | 4080 |
| ccggcaaaca | aaccaccgct | ggtagcggtg | gtttttttgt | ttgcaagcag cagattacgc | 4140 |
| gcagaaaaaa | aggatctcaa | gaagatcctt | tgatctttc | tacggggtct gacgctcagt | 4200 |

```
ggaacgaaaa ctcacgttaa gggattttgg tcatgagatt atcaaaaagg atcttcacct      4260 agatccttt  aaattaaaaa tgaagtttta aatcaatcta aagtatatat gagtaaactt      4320
ggtctgacag ttaccaatgc ttaatcagtg aggcacctat ctcagcgatc tgtctatttc      4380
gttcatccat agttgcctga ctccccgtcg tgtagataac tacgatacgg gagggcttac      4440
catctggccc cagtgctgca atgataccgc gagacccacg ctcaccggct ccagatttat      4500
cagcaataaa ccagccagcc ggaagggccg agcgcagaag tggtcctgca actttatccg      4560
cctccatcca gtctattaat tgtttgccgg aagctagagt aagtagttcg ccagttaata      4620
gtttgcgcaa cgttgttgcc attgctacag gcatcgtggt gtcacgctcg tcgtttggta      4680
tggcttcatt cagctccggt tcccaacgat caaggcgagt tacatgatcc cccatgttgt      4740
gcaaaaaagc ggttagctcc ttcggtgctc cgatcgttgt cagaagtaag ttggccgcag      4800
tgttatcact catggttatg gcagcactgc ataattctct tactgtcatg ccatccgtaa      4860
gatgcttttc tgtgactggt gagtactcaa ccaagtcatt ctgagaatag tgtatgcggc      4920
gaccgagttg ctcttgcccg gcgtcaatac gggataatac cgcgccacat agcagaactt      4980
taaaagtgct catcattgga aaacgttctt cggggcgaaa actctcaagg atcttaccgc      5040
tgttgagatc cagttcgatg taacccactc gtgcacccaa ctgatcttca gcatcttta     5100 ctttcaccag cgtttctggg tgagcaaaaa caggaaggca aaatgccgca aaaagggaa      5160 taaggcgac acggaaatgt tgaatactca tactcttcct ttttcaatat tattgaagca      5220
tttatcaggg ttattgtctc atgagcggat acatatttga atgtatttag aaaaataaac      5280 aaatagggt tccgcgcaca tttccccgaa aagtgccacc tgacgtctaa gaaaccatta      5340
ttatcatgac attaacctat aaaaataggc gtatcacgag gcctatgcgg tgtgaaatac      5400
cgcacagatg cgtaaggaga aaataccgca tcaggcgcca ttcgccattc aggctgcgca      5460
actgttggga agggcgatcg gtgcgggcct cttcgctatt acgccagctg gcgaaagggg      5520
gatgtgctgc aaggcgatta agttgggtaa cgccagggtt ttcccagtca cgacgttgta      5580
aaacgacggc cagtgccaag cttgcatgcc tgcaggtcga                            5620
```

<210> SEQ ID NO 22
<211> LENGTH: 45
<212> TYPE: DNA
<213> ORGANISM: Artificial Sequence
<220> FEATURE:
<221> NAME/KEY: stem_loop
<222> LOCATION: 11..45
<223> OTHER INFORMATION: Description of Artificial Sequence: Asp 718
      hairpin

<400> SEQUENCE: 22

```
gtacactgac ctagtgccgc ccgggcaaag cccgggcggc actag                        45
```